United States Patent
Liao et al.

(10) Patent No.: US 9,611,502 B2
(45) Date of Patent: Apr. 4, 2017

(54) METHOD FOR SIMULTANEOUSLY MEASURING ACTIVITY OF VARIOUS ENZYMES BY USING MULTI-WAVELENGTH ABSORPTION SINGLE CHANNEL

(71) Applicant: Chongqing Medical University, Chongqing (CN)

(72) Inventors: Fei Liao, Chongqing (CN); Xiaolan Yang, Chongqing (CN); Hongbo Liu, Chongqing (CN); Jizheng Dang, Chongqing (CN); Gaobo Long, Chongqing (CN); Yuanli Li, Chongqing (CN); Lin Liu, Chongqing (CN)

(73) Assignee: Chongqing Medical University, Chongqing (CN)

( * ) Notice: Subject to any disclaimer, the term of this patent is extended or adjusted under 35 U.S.C. 154(b) by 144 days.

(21) Appl. No.: 14/430,391

(22) PCT Filed: Sep. 24, 2012

(86) PCT No.: PCT/CN2012/081869
§ 371 (c)(1),
(2) Date: Mar. 23, 2015

(87) PCT Pub. No.: WO2014/043923
PCT Pub. Date: Mar. 27, 2014

(65) Prior Publication Data
US 2015/0225764 A1    Aug. 13, 2015

(30) Foreign Application Priority Data
Sep. 21, 2012    (CN) .......................... 2012 1 0355606

(51) Int. Cl.
| | |
|---|---|
| *G01N 21/31* | (2006.01) |
| *C12Q 1/25* | (2006.01) |
| *G01N 21/27* | (2006.01) |
| *C12Q 1/00* | (2006.01) |
| *G01N 21/33* | (2006.01) |

(52) U.S. Cl.
CPC .................. *C12Q 1/25* (2013.01); *C12Q 1/00* (2013.01); *G01N 21/272* (2013.01); *G01N 21/31* (2013.01); *C12Q 2334/00* (2013.01); *G01N 21/33* (2013.01); *G01N 2021/3125* (2013.01); *G01N 2333/904* (2013.01); *G01N 2333/916* (2013.01); *G01N 2333/91074* (2013.01); *G01N 2333/938* (2013.01)

(58) Field of Classification Search
None
See application file for complete search history.

(56) References Cited

FOREIGN PATENT DOCUMENTS

| | | |
|---|---|---|
| CN | 1786185 | 6/2006 |
| CN | 101218354 | 7/2008 |
| CN | 102533937 | 7/2012 |
| CN | 102879343 | 10/2014 |
| WO | 2004/063339 | 7/2004 |

OTHER PUBLICATIONS

Löffler et al. Anal Biochem.,1984,142(2):312-316.*
Choi MJ et al.; Simple enzyme immunoassay for the simultaneous measurement of whole choriogonadotropin molecules and free beta-subunits in sera of women with abnormal pregnancies or tumors of the reproductive system; CLin Chem May 1991;37(5):673-7.
First Office Action of CN 201210355606.8 dated Apr. 2, 2014.
Dean, K.J. et al.; Simultaneous determination of phenytoin and phenobarbital in serum or plasma by substrate-labeled fluorescent immunoassay; Clin Chem Jun. 1983; 29(6): 1051-6.

(Continued)

*Primary Examiner* — Michael Borin
(74) *Attorney, Agent, or Firm* — Rankin, Hill & Clark LLP

(57) ABSTRACT

A method for simultaneously measuring the activities of multiple kinds of enzymes in single channel through concimitantly monitoring multiple wavelength absorbances is claimed; based on linear additivity of absorbances and the isoabsorbance wavelengths of chromogenic substrates and their chromogenic products, both the principles for the combination of chromogenic substrates required for simultaneously measuring the activities of multiple kinds of enzymes in single channel through concimitantly monitoring multiple wavelength absorbances and an approach for data processing to eliminate the interference of the overlapped absorbances are developed, kinetic analysis of reaction curves via numerical integration eliminates the interference of all substrates and products and estimates the maximal reaction rates of the enzymes to be measured, giving the linear ranges and the limits of quantification for simultaneously measuring the activities of multiple kinds of enzymes in single channel comparable to those by separate assays; the present invention is applicable for simultaneously measuring the activities of multiple kinds of enzymes in biological samples, simultaneously measuring multiple components by enzyme-labeled immunoassays, screening simultaneously of inhibitors against multiple targets, for the practice in clinical biochemical analyses, clinical immunoassays, health laboratory analyses, the discovery of inhibitors, and the basical researches which need the present invention.

9 Claims, 10 Drawing Sheets

(56) References Cited

OTHER PUBLICATIONS

Figure 1:
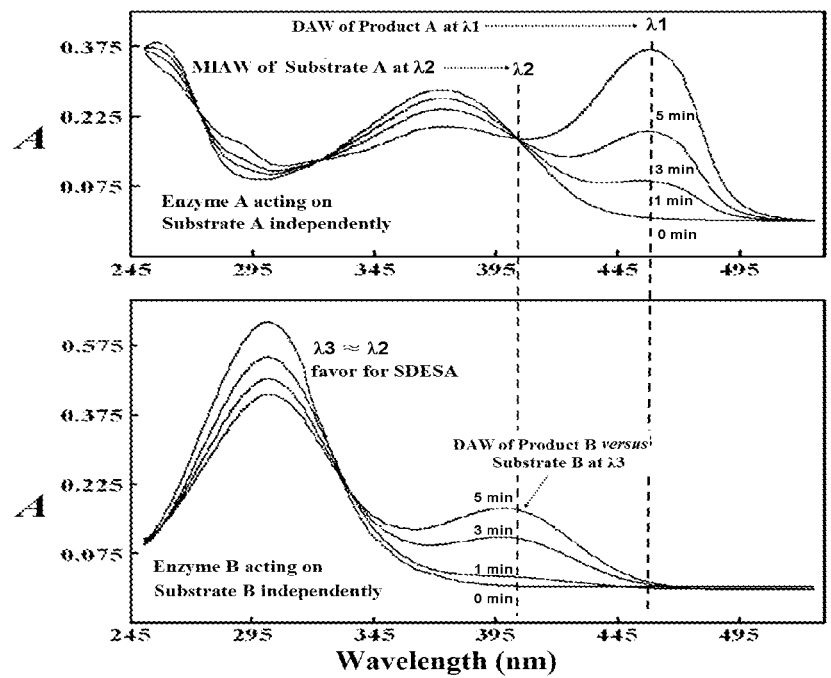

Krambovitis, E. et al.; Estrogen and progesterone receptors in breast cancer microsamples simultaneously quantified by enzyme-ligand immunoassay; Clin Chem Jan. 1995;41(1): 48-53.
Ng ML et al.; Enzyme immunoassay for simultaneous measurement of autoantibodies against thryoglobulin and thyroid microsome in serum; Clin Chem Dec. 1987;33(12): 2286-8.
Osuchowski, MF et al.; The repetitive use of samples to measure multiple cytokines: the sequential ELISA; Methods Apr. 2006;38(4): 304-11.
Porstmann T. et al.; Two-colour combination enzyme-linked immunosorbent assay for the simultaneous detection of HBV and HIV infection; J Immunol Methods Jan. 14, 1993;158(1): 95-106.
Sun J. et al.; Development of enzyme linked immunoassay for the simultaneous detection of carbaryl and metolcarb in different agricultural products; Anal Chim Acta May 7, 2010;666(1-2): 76-82.
Blake C. et al.; Simultaneous enzyme immunoassay of two thyroid hormones; Clin Chem Jul. 1982;28(7): 1469-73.
International Search Report of PCT/CN2012/081869 dated Jan. 3, 2013, 6 pages (w/ English translation).

\* cited by examiner

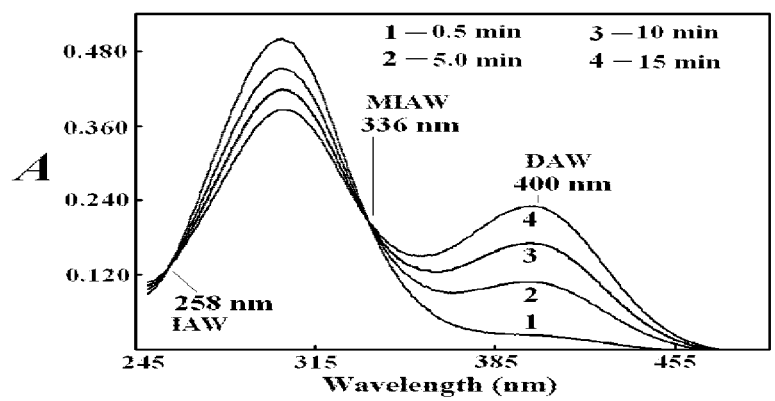
Fig. 3-a.
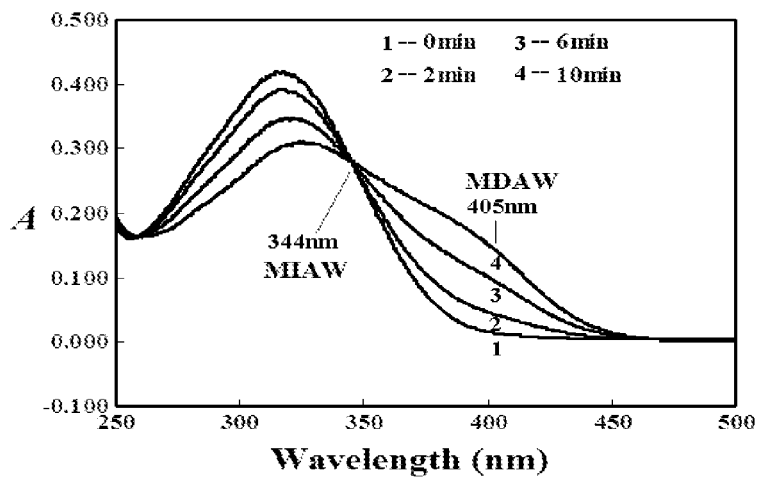
Fig. 3-b.
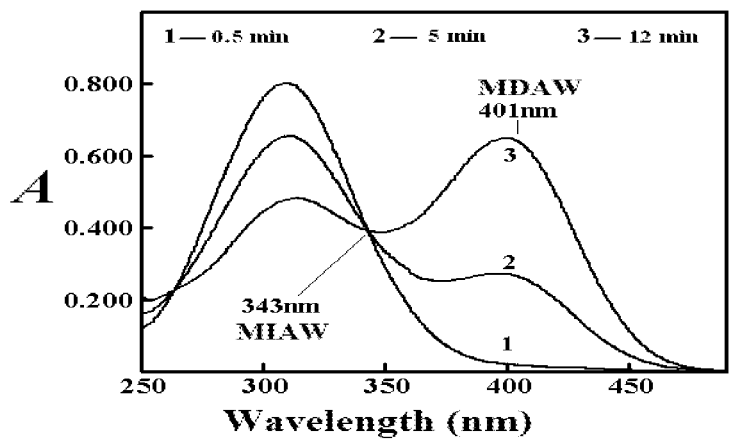
Fig. 3-c.

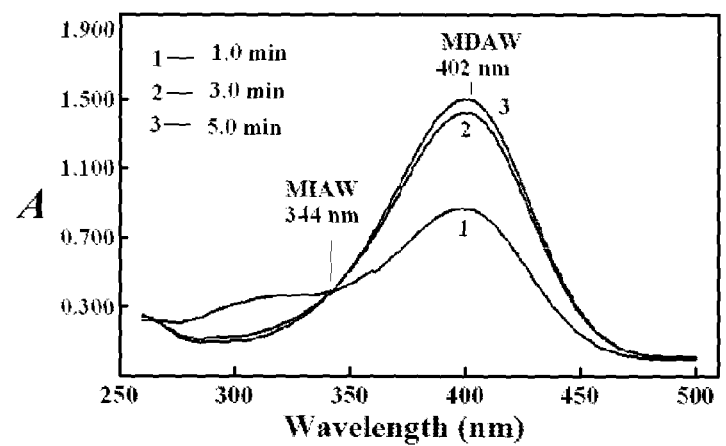
Fig. 3-d.
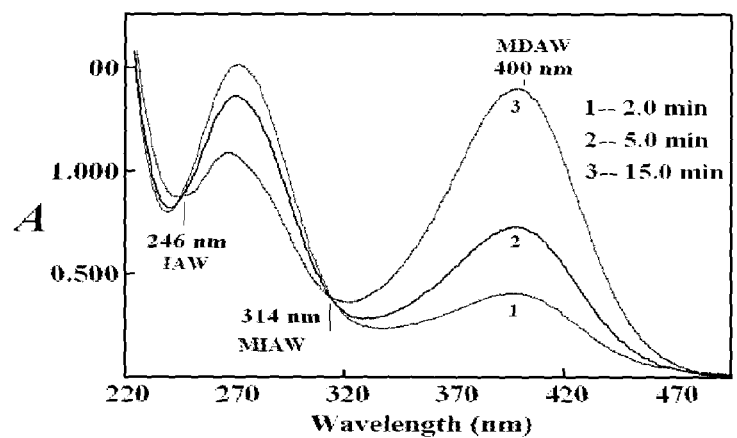
Fig. 3-e.
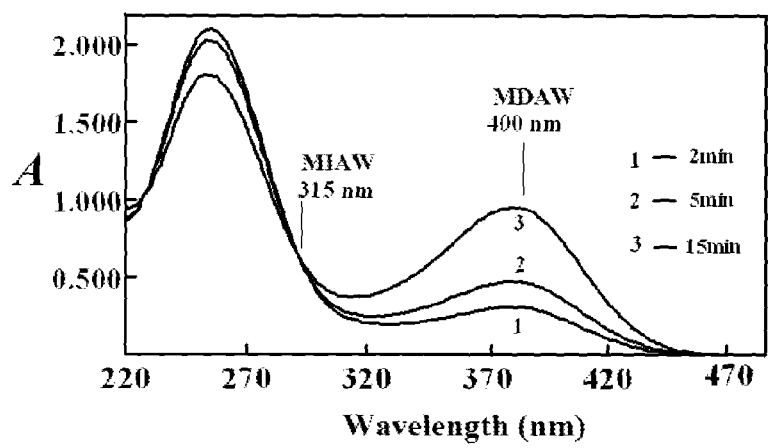
Fig. 3-f.

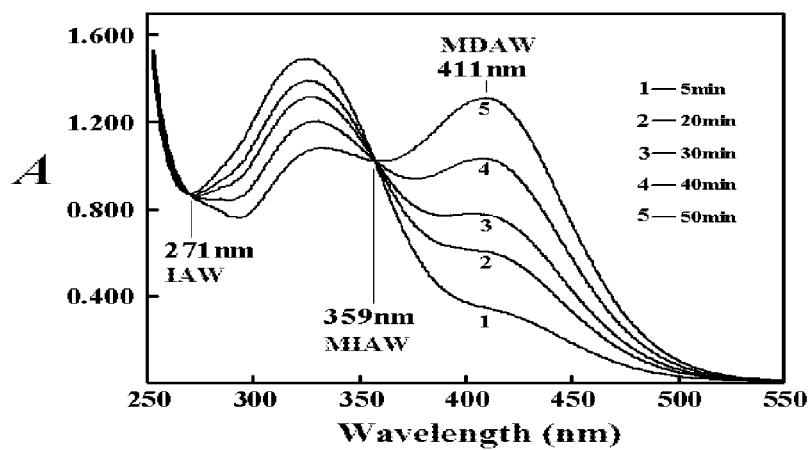
Fig. 3-g.
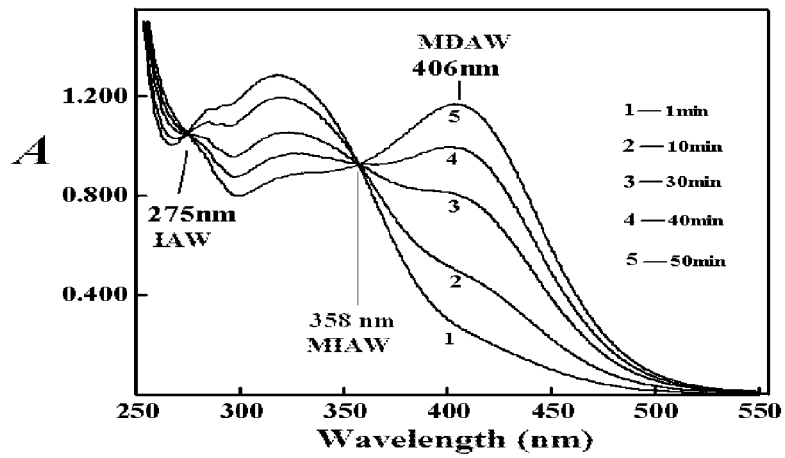
Fig. 3-h.
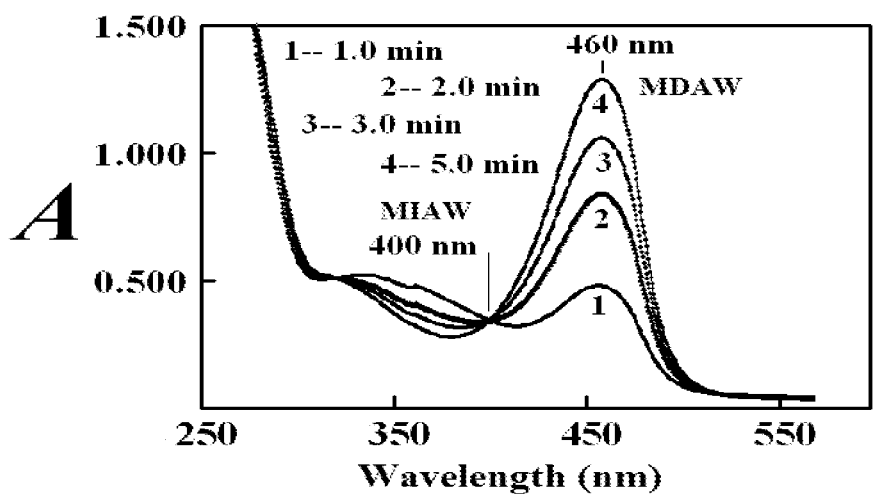
Fig. 4-a.

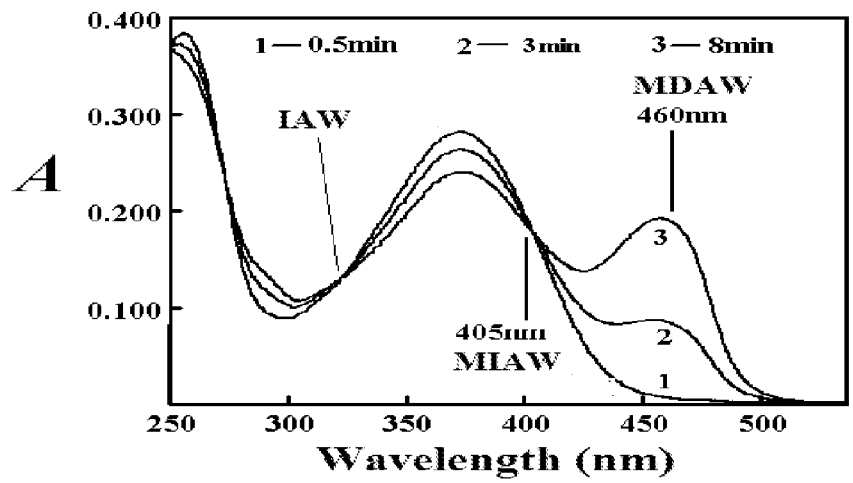
Fig. 4-b.
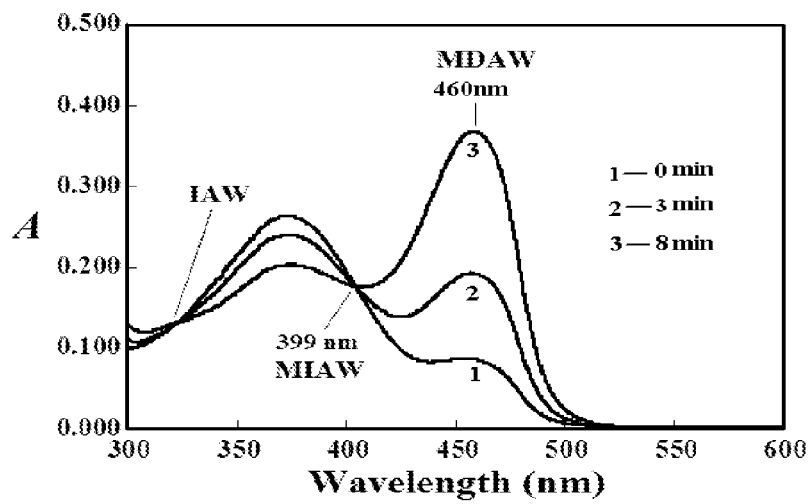
Fig. 4-c.
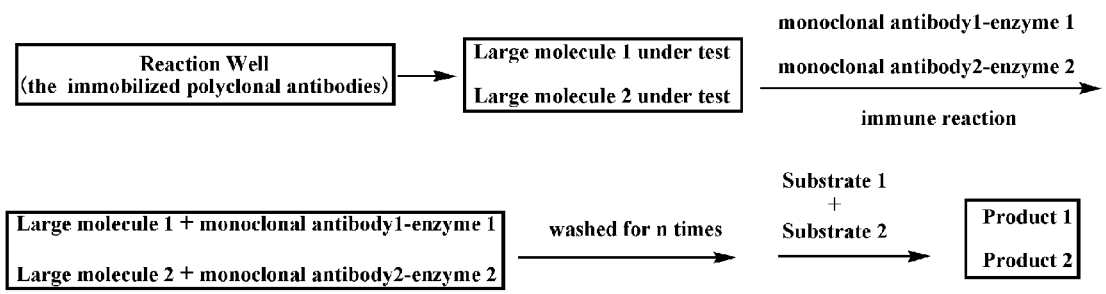
Fig. 5.

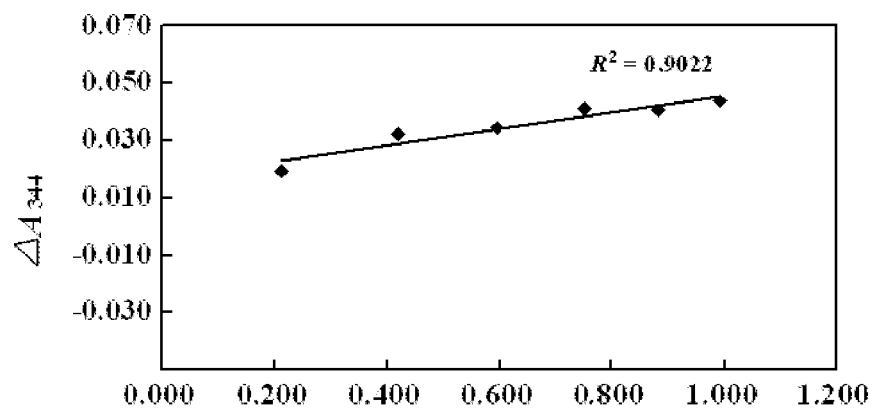
Fig. 6-a.
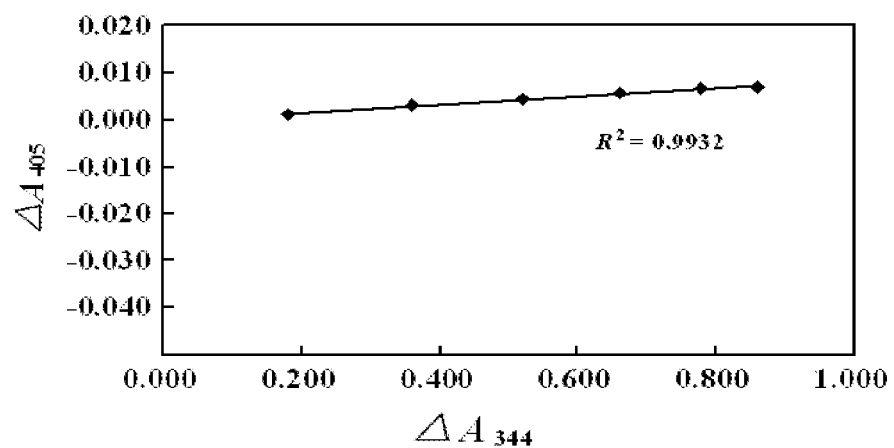
Fig. 6-b.
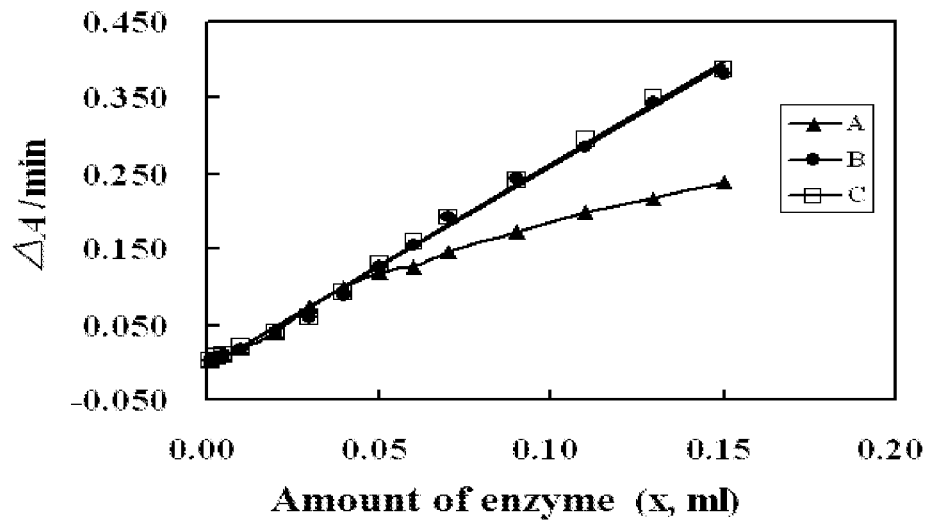
Fig. 6-c.

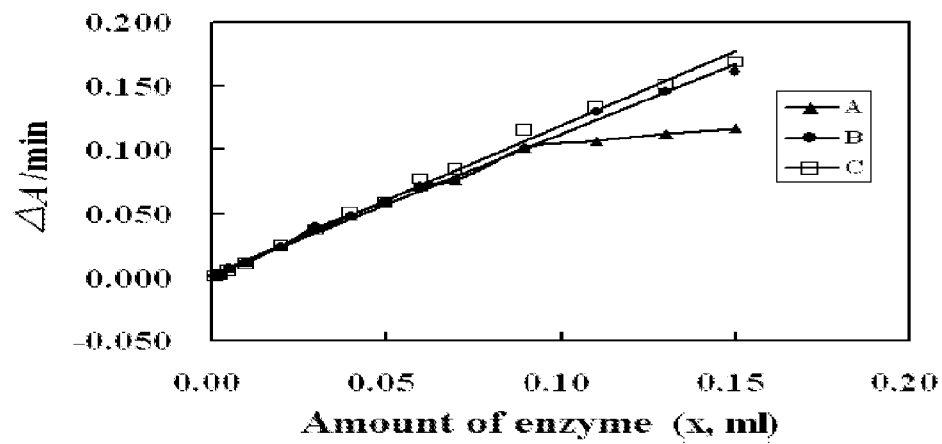
Fig. 6-d.
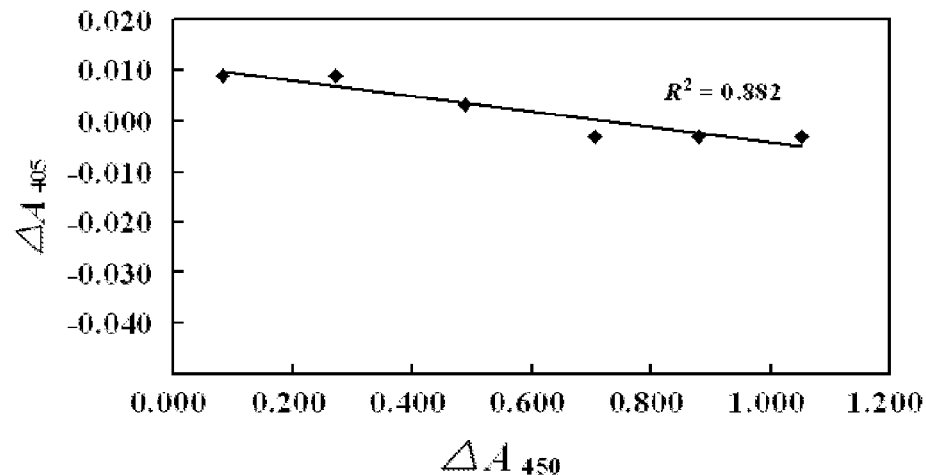
Fig. 7-a.
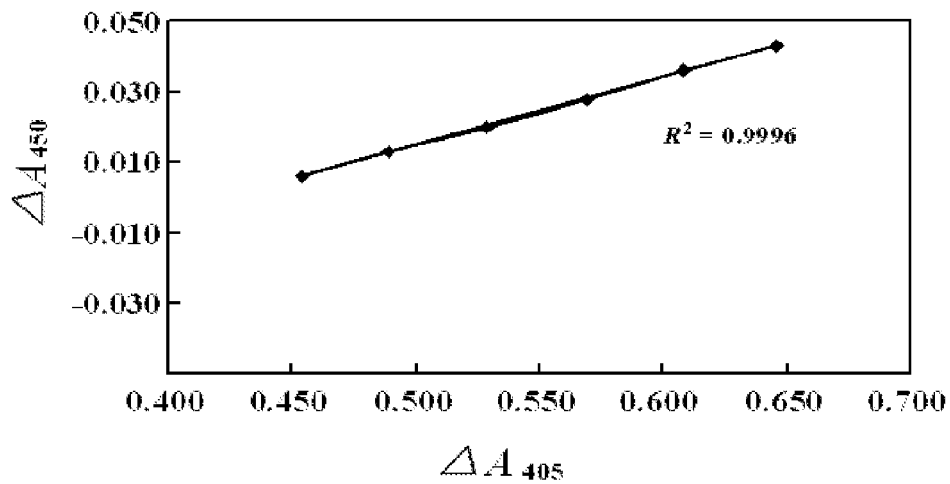
Fig. 7-b.

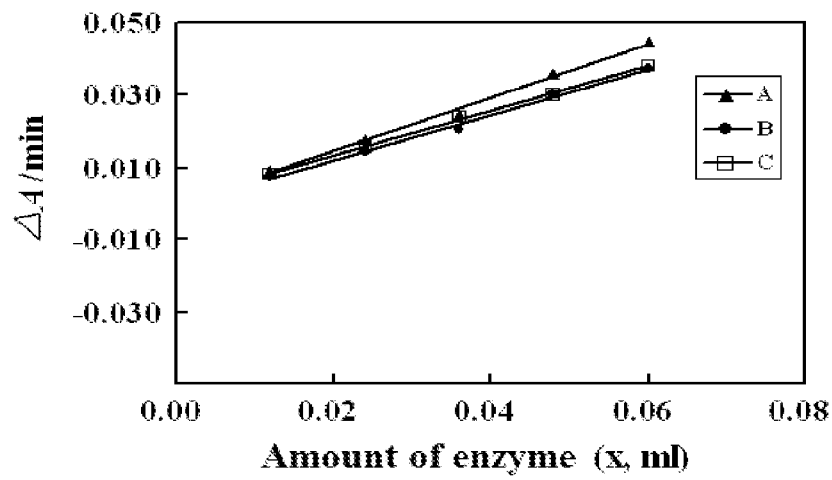
Fig. 7-c.
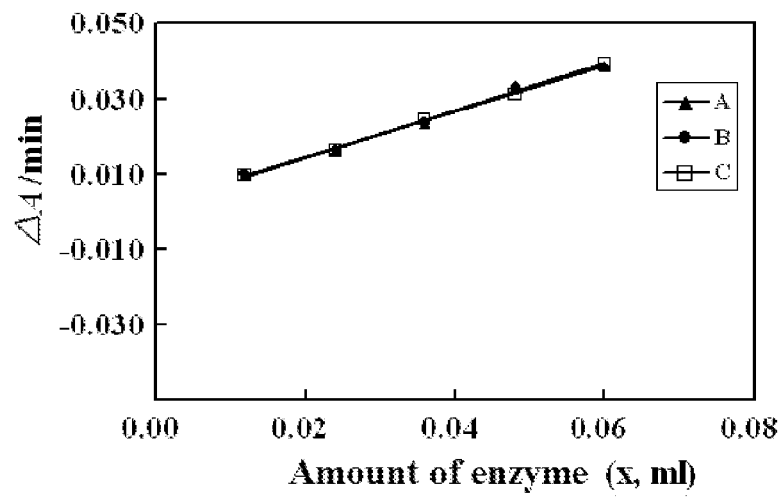
Fig. 7-d.
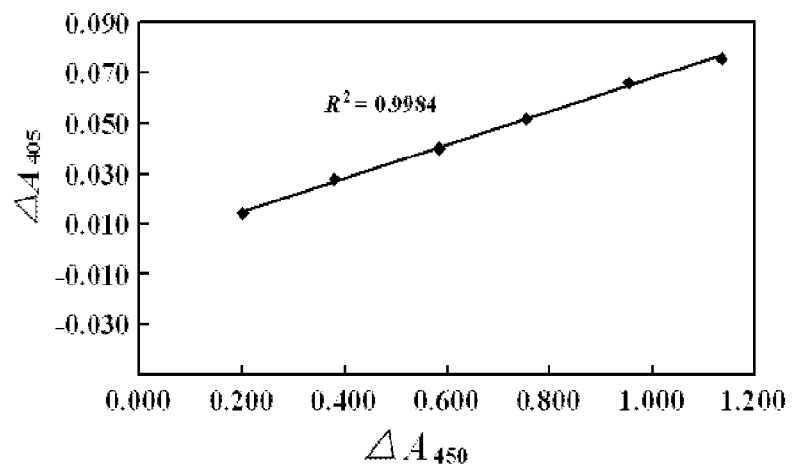
Fig. 8-a.

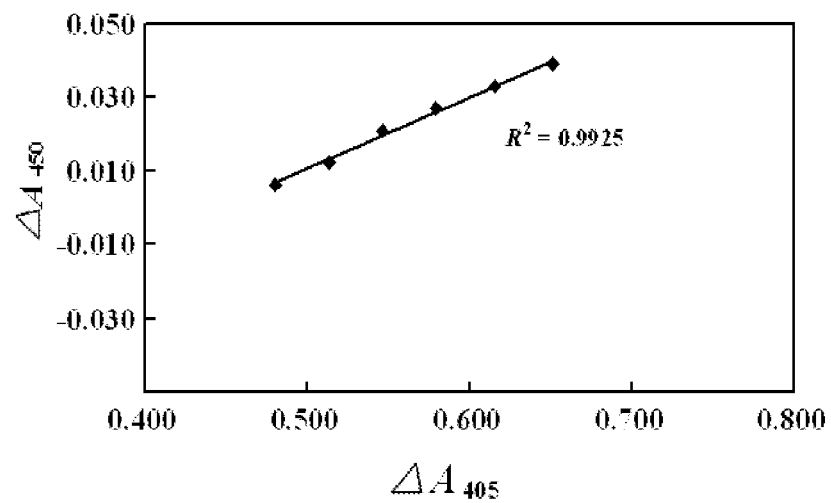
Fig. 8-b.
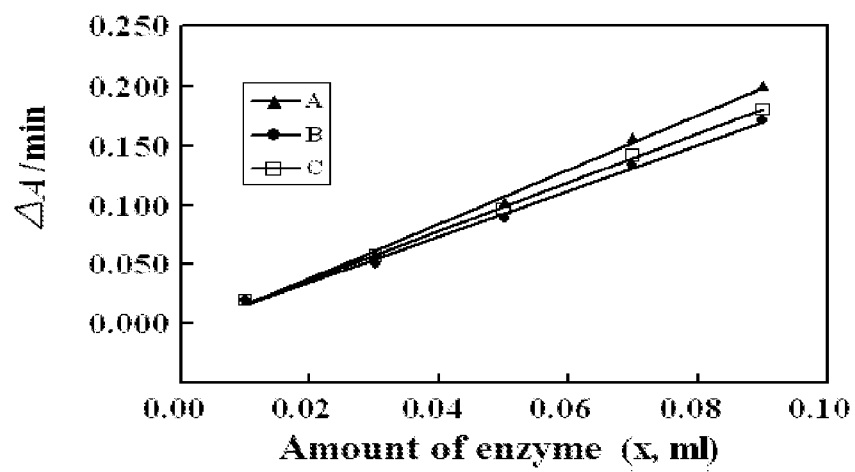
Fig. 8-c.
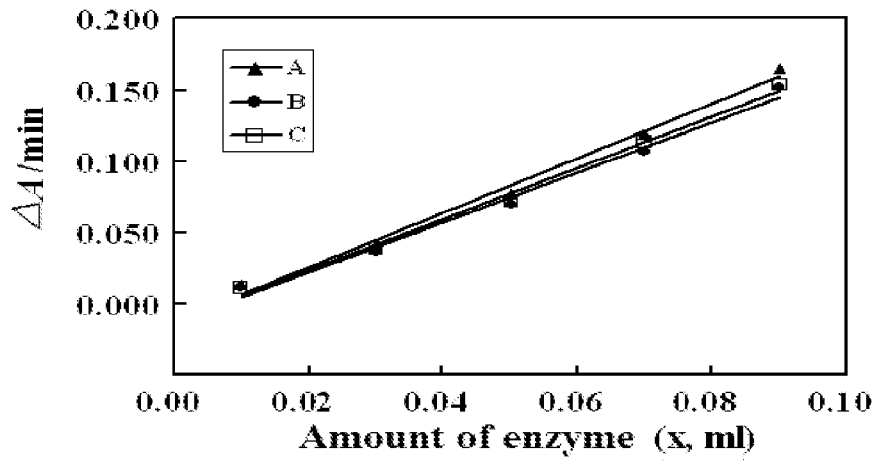
Fig. 8-d.

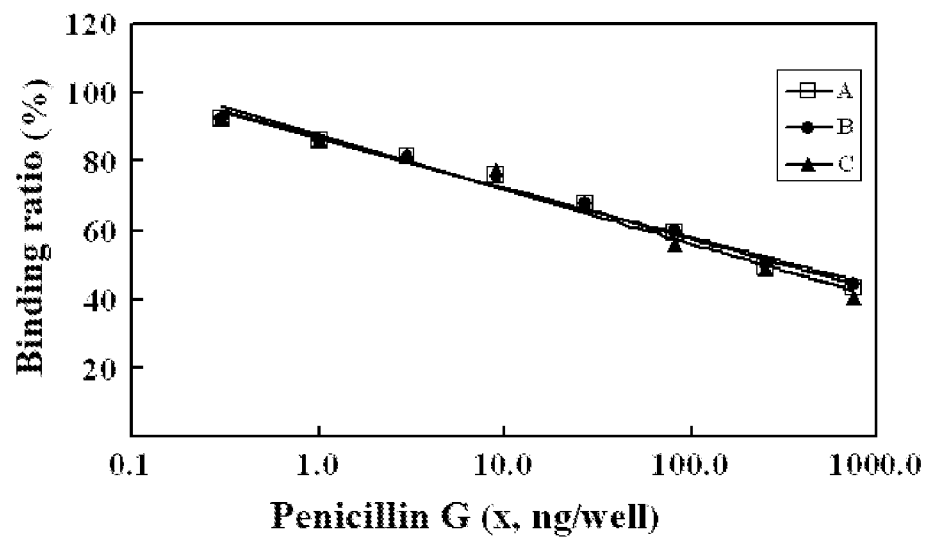
Fig. 8-e.
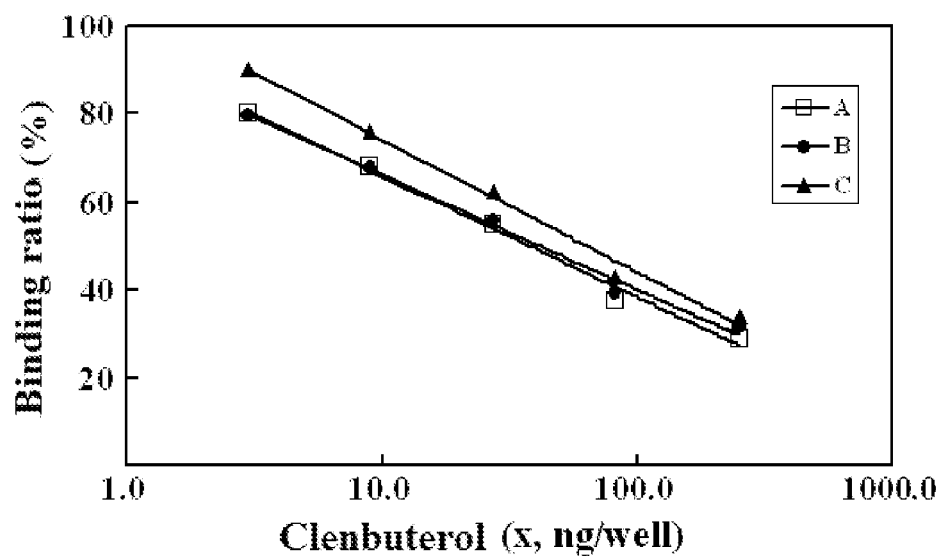
Fig. 8-f.

METHOD FOR SIMULTANEOUSLY MEASURING ACTIVITY OF VARIOUS ENZYMES BY USING MULTI-WAVELENGTH ABSORPTION SINGLE CHANNEL

FIELD OF INVENTION

This invention relates to a simultaneously-measuring method of the activities of multiple kinds of enzymes, specifically a method for simultaneously measuring the activities of multiple kinds of enzymes by concomitantly monitoring multiple wavelength absorbances in single channel.

BACKGROUND OF THE INVENTION

For convenience, it is defined that analysis sensitivity of enzyme activity is the slope for the linear response of absorbance change rates to enzyme quantities, the limit of quantification (LOQ) is the quantity of an enzyme corresponding to the intercept of the linear response plus five times the standard error of estimate for the linear response. The assay of enzyme activity is always required to have an analysis sensitivity as high as possible, a LOQ as low as possible and analysis efficiency as high as possible. The use of specific chromogenic substrate of an enzyme facilitates the conventional and sensitive assay of enzyme activity via the continuous monitoring of reaction curves as absorbance changes; such a process for enzyme activity assay is widely utilized in conventional clinical biochemical analysis, health laboratory analysis to detect food contaminants and environment pollutants as enzyme inhibitors, high-throughput screening of enzyme inhibitor libraries and enzyme-labeled immunoassays. On the other hand, the high specificity and sensitivity for enzyme activity assay makes enzymes suitable labels for immunoassays represented by Enzyme-linked immunoassay (ELISA), which is the fundamental analysis method in clinical laboratory analysis of specific small biochemicals or macromolecules in mixture samples. During ELISA analysis, a component for capturing is immobilized in microplate wells to facilitate the separation of immunocomplexes, and wash process is needed; a single complete analysis process usually spends about 130 min or more, indicating low analysis efficiency. Therefore, the enhancement of the analysis efficiency of enzyme activity assay has great significance.

To date, continuous monitoring of reaction curves for enzyme activity assay always uses one substrate to measure the activity of just one enzyme each time, i.e., one enzyme in one reaction channel (solution). In clinical laboratory analysis, it is common to measure activities of two or even more enzymes in one sample, for instance, the diagnosis of liver function requires the assay of glutamic acid pyruvate aminotransferase, glutamic acid oxaloacetate aminotransferase, gamma-glutaminyltransferase (GGT), alkaline phosphatase, and so on in the same specimen; the diagnosis of acute pancreatitis requires the assay amylase and lipase in the same specimen. On the other hand, ELISA has a definite disadvantage of low efficiency since each analysis process needs a long time. Furthermore, the screening of libraries of enzyme inhibitors always determines the activities of just one target enzyme each time, resulting in high cost and low efficiency, and the consumption of more compounds in the libraries. The development of new techniques for enhancing the analysis efficiency of enzyme activity assay at sensitivity and LOQ comparable to those for separate assay of single component has its own biomedicinal significance.

The direct forward strategy to enhance the efficiency for enzyme activity assay is the real-time or nearly-real-time determination of the activities of multiple enzymes each time in one reaction channel by using multiple chromogenic substrates to continuous monitor absorbance changes of multiple chromogenic products. Spectrophotometers for concomitantly measuring multiple wavelength absorbances are already accessible, for example, Biotek ELX 800 microplate reader can concomitantly measure three wavelength absorbances, MAPADA UV 1600PC spectrophotometer can concomitantly measure seven wavelength absorbances. In fact, there are short enough lagging times between the assays of absorbance at different wavelengths with such instruments. When double monochromators or diode array detectors are used, there can be real-time simultaneous assays of absorbance at multiple wavelengths. Therefore, the development of principles for the combination of chromogenic substrates and techniques for data processing can potentially realize simultaneous measurement of the activities of multiple kinds of enzymes in single channel through the concomitant monitoring of multiple wavelength absorbances to obtain reaction processes of multiple enzymes, which can have sensitivity and LOQ for simultaneous measurement of the activities of multiple kinds of enzymes comparable to those for separate assays, and greatly accelerates ELISA and high-content screening of libraries of enzyme inhibitors.

It had long been reported for the use of two label enzymes for simultaneous ELISAs of two components in one reaction channel, but there were in fact no initiations of the reactions of two enzymes in the same reaction channel and continuous monitoring of the reaction processes of two enzymes. Blake et al in 1982 reported the use of calf intestinal alkaline phosphatase (CIAP) and β-galactosidase (β-gal) to label two haptens for simultaneous competitive assays of two free haptens in single reaction channel (Clin Chem 1982; 28(7): 1469-1473). However, the reactions of such two labelled enzymes were initiated in two different reaction solutions rather than concomitantly in the same reaction solution, and the reaction processes of such two labelled enzymes were not monitored concurrently; this method used phenolphthalein monophosphate as the substrate of CIAP that had specific activity just about 7% of that on p-nitrophenylphosphate.

Too lower sensitivity and high cost on substrate made this improvement seldom practiced in biomedicine. In other ELISA techniques for the assays of two components in single reaction channel, there were no concomitant initiation of the reactions of two enzymes, no simultaneous assays of absorbance of two products and no continuous monitoring of reaction processes of two enzymes (Dean et al., *Clin Chem*, 1983; 29(6):1051-1056. Ng, et al. *Clin Chem*, 1987; 33(12): 2286-2288. Choi, et al. *Clin Chem*, 1991; 37(5): 673-677. Porstmann T, et al. *J Immunol Methods*. 1993; 158:95-106. Krambovitis E, et al. *Clin chem* 1995; 41:48-53. Osuchowski, et al. *Methods* 2006; 38:304-311 and Sun J, et al. *Anal Chim Acta* 2010; 666: 76-82). Therefore, to date, all ELISA techniques have not been improved to concomitantly initiate reactions of multiple label enzymes and concurrently monitor absorbance changes of multiple products as the reaction curves; in the field for enzyme inhibitor screening, there are no reports on simultaneous assay activities of multiple enzymes to detect the actions of one inhibitor on multiple target enzymes.

Clearly, the principles for the combination of chromogenic substrates and the techniques for data processing are required to develop a method for simultaneously measuring the activities of multiple kinds of enzymes through the concomitantly monitoring of multiple wavelength absorbances. It was under the support from "863"-program 2011AA02A108, the inventors developed the as-proposed novel method.

SUMMARY OF THE INVENTION

The aim of this invention is to provide a method for simultaneously measuring of the activities of multiple kinds of enzymes in single channel through concomitantly monitoring multiple wavelength absorbances, which makes use of the linear additivity property of the absorbances of substances bearing negligible interactions, the isoabsorbance wavelength (IAW) of a chromogenic substrate and its corresponding chromogenic product under the action of an enzyme, to develop the new principles for both the desired combination of a group of chromogenic substrates, a new approach of data processing for eliminating the interference of the overlapped absorbances of involved substances and a way to solve interfering actions of involved substrates and products of different enzymes, for simultaneously measuring the activities of multiple kinds of enzymes in single channel through concomitantly monitoring multiple wavelength absorbances.

For simultaneously measuring of the activities of multiple kinds of enzymes in single channel through concomitantly monitoring multiple wavelength absorbances by the present invention, the following steps are needed:

a. determining the combination of chromogenic substrates required for simultaneously measuring the activities of multiple kinds of enzymes:

a1 selecting the combination of chromogenic substrates that meets the following criteria according to the specificity of the enzymes to be measured: the selected chromophores can be respectively used to prepare the chromogenic substrates of the enzyme to be measured; in the obtained combination of chromogenic substrates, the difference absorbance peak maximum wavelengths of the chromogenic products formed under the actions of the respective enzyme to be measured with respect to their chromogenic substrates are arranged from large to small to give a one-dimension array, the distance between any two adjacent difference absorbance peak maximum wavelengths of the chromogenic products in the aforementioned array is greater than 30 nm and preferably as far as possible; in the array of the difference absorbance peak maximum wavelengths of the chromogenic products from large to small, except for the chromogenic substrate whose chromogenic product has the difference absorbance peak maximum wavelength nearest to the infrared end, the difference absorbance peak maximum wavelength of each chromogenic product obtained from its chromogenic substrate under the action of the corresponding enzyme is less than 25 nm and preferably as shorter as possible away from the maximum isoabsorbance wavelength of one of the chromogenic substrates in the aforementioned array;

a2 synthesizing corresponding chromogenic substrates of the enzymes to be measured respectively by the chromophores selected in step a1, and using them in combination;

b. in one reaction mixture or enzyme reaction system, that is a single reaction channel, synchronously initiating the specific catalyzed reactions of the multiple kinds of enzymes to be measured with their corresponding chromogenic substrates combined for use as a mixture;

c. selecting a combination of wavelengths for measuring absorbance: taking the chromogenic substrate whose chromogenic product thereof has the difference absorbance peak maximum wavelength nearest to the infrared end as chromogenic substrate A, determining the absorbance of the chromogenic product at the difference absorbance peak maximum wavelength of the chromogenic product of chromogenic substrate A; determining the absorbance of the chromogenic products or chromogenic substrates of the other enzymes whose activities are to be measured at the isoabsorbance wavelengths of the chromogenic substrate A;

d. realizing simultaneous measurement of multiple wavelength absorbances for concomitantly monitoring the reaction processes of multiple kinds of the enzymes to be measured in a single channel through swift alteration of the wavelengths selected in the combination;

e. developing an approach of data processing for eliminating the interference of the overlapped absorbance of chromogens involved in enzyme reactions based on the linear additivity property of absorbances of non-interacting compounds, to obtain an absorbance change curve of the chromogenic product or substrate of each enzyme to be measured after the elimination of the overlapping interference in absorbance spectra; if the action of an enzyme of interest for activity assay is not subject to the interference by the products and substrates of the other enzymes in the reaction system, and the substrate concentration is over three times of a Michaelis constant of the corresponding enzyme, the classical initial rate method is used to analyze the absorbance change curve of the chromogenic product or substrate with no disturbing absorbance to determine the initial rate; if the action of an enzyme to be measured is not disturbed by the products and substrates of the other enzymes in the reaction system, however, the concentration of the used chromogenic substrate is over 5% of a Michaelis constant of the corresponding enzyme but less than three times of the Michaelis constant, the classical initial rate method is integrated with kinetic analysis of reaction process to analyze the reaction curve as the absorbance change of the chromogenic product or substrate thereof with no disturbing absorbance to determine the initial rate; when the action of an enzyme to be measured is disturbed by substrates and/or products of itself and/or other enzymes in the reaction system, a group of the differential rate equations that describe the kinetics of the reaction system is numerically integrated for fitting to the reaction curve as the absorbance change of the chromogenic product or substrate of the enzyme to be measured with no disturbing absorbance of chromogenic products and chromogenic substrates in the reaction system, to estimate the maximum reaction rate thereof, which is used directly as an index of the activity of the enzyme to be measured, or is further converted according to the differential rate equations into an initial rate at the substrate concentration of 93% of the initial one for reflecting the activity of the enzyme to be measured;

Further, for the practice of this invention, the difference absorbance peak maximum wavelengths of chromogenic products versus their chromogenic substrates are greater than 300 nm, and the maximal absorbance peak wavelengths of the chromogenic substrates thereof are less than the maximal absorbance peak wavelength of the corresponding chromogenic products, otherwise the rates for the enzymes catalyzing the reversed reaction are determined to reflect the activities of these enzymes; for any two chromogenic substrates whose chromogenic products formed thereof under the actions of the enzymes whose activities are to be measured have the difference absorbance peak maximum wavelengths adjacent to each other in the aforementioned array of the difference absorbance peak maximum wavelengths, when the difference absorbance peak maximum wavelength of the chromogenic product is both closer to the UV end and is equal to or less than 5 nm distance away from the maximal isoabsorbance wavelength of the chromogenic substrate whose chromogenic product has the difference absorbance peak maximum wavelength closer to the infrared end, this two are the preferred combination of chromogenic substrates; in the used combination of all chromogenic substrates, each chromogenic substrate is only converted by the action of one enzyme whose activity is to be measured into the corresponding chromogenic product(s), without being affected or being affected in a negligible way by the any other enzyme in the sample; the expression "without being affected or being effected in a negligible way by the any other enzyme in the sample" herein means when the concentration of the chromogenic substrate corresponding to enzyme I in the sample differ from the Michaelis constant thereof in less than 50%, the specific activity of the any other enzymes in the sample acting on the chromogenic substrate thereof is less than 1% of the specific activity of enzyme I acting on the same chromogenic substrate; in step b, a buffer medium and reaction conditions suitable for the enzyme to be measured to take effect in simultaneously measuring the activities are selected, that is, the buffer medium has a pH from 5.0 to 9.0, and close to the optimum pH for the enzyme to be measured in the sample whose specific activity is the lowest, the used reaction temperature is between 20 and 40° C.

Further, for the practice of this invention, said chromogenic substrates comprise natural chromogenic substrates and nonnatural chromogenic substrates; wherein the natural chromogenic substrates comprises nicotinamide adenine dinucleotide and nicotinamide adenine dinucleotide phosphate; nonnatural chromogenic substrates consists of a chromophore and a moiety recognized by enzymes for action, the chromophore comprises, but is not limited to, 4-nitrophenol, 4-nitrobenzenethiol, 4-nitroaniline, 4-nitro-1-naphtho 1,4-nitro-1-naphthylthiol, 4-nitro-1-naphthylamine, 2-naphthol, 4-chloro phenol, rosolic acid or the derivatives of these aromatic phenol and/or aromatic amines.

Further, for simultaneously measuring the activities of two kinds of enzymes in single channel through concomitantly monitoring two wavelength absorbances by the present invention, in step a, the two enzymes to be measured are named as enzyme A and enzyme B, the required two chromophores are chromophore A and chromophore B, respectively, the corresponding two chromogenic substrates are chromogenic substrate A and chromogenic substrate B, respectively, two chromogenic products produced by the action of the two enzymes to be measured are chromogenic product A and chromogenic product B, respectively, the combination of these chromogenic substrates and chromogenic products is required to meets the following criteria: (1) the difference absorbance peak maximum wavelength X1 of chromogenic product A is closer to the infrared end, the difference absorbance peak maximum wavelength X2 of chromogenic product B is closer to the UV end, the distance between the difference absorbance peak maximum wavelength X2 of chromogenic product B and the difference absorbance peak maximum wavelength X1 of chromogenic product A is greater than 30 nm, and preferably as far as possible; (2) the maximum isoabsorbance wavelength of chromogenic product A is Y1, and is equal to or less than 25 nm distance away from the difference absorbance peak maximum wavelength X2 of chromogenic product B, and the distance is preferably as short as possible;

In steps b, c and d for simultaneously measuring the activities of two kinds of enzymes through concomitantly monitoring two wavelength absorbances in single channel by the present invention, synchronously initiating the reactions of two kinds of the enzymes from a sample with chromogenic substrate A and chromogenic substrate B in a single reaction channel, to obtain chromogenic product A and chromogenic product B; selecting the difference absorbance peak maximum wavelength X1 of chromogenic product A as λ1 to determine the absorbance of the chromogenic product A, selecting the maximum isoabsorbance wavelength Y1 of chromogenic product A as λ2 to determine the absorbance of chromogenic product B; concomitantly monitoring two wavelength absorbances concurrently records the reaction processes of the two kinds of enzymes to be measured in a single channel by swift alteration of the measuring wavelength;

In step e for simultaneously measuring the activities of two kinds of enzymes through concomitantly monitoring two wavelength absorbances in single channel by the present invention, developing an approach of data processing for eliminating the interference of the overlapped absorbances of chromogens involved in enzyme reactions based on the linear additivity property of absorbances of non-interacting compounds, to obtain an absorbance change curve of the chromogenic product or substrate of each enzyme to be measured after the elimination of the overlapping interference in absorbance spectra; if the action of an enzyme to be measured is not subject to the interference by the products and substrates of the other enzymes in the reaction system, and the substrate concentration is over three times of the Michaelis constant of the corresponding enzyme, the classical initial rate method is used to analyze the absorbance change curve of the chromogenic product or substrate with no disturbing absorbance to determine the initial rate; if the action of an enzyme to be measured is not interfered by the products and substrates of the other enzymes in the reaction system, however, the concentration of the used chromogenic substrate is over 5% of the Michaelis constant of the corresponding enzyme but less than three times of the Michaelis constant, the classical initial rate method is integrated with kinetic analysis of reaction process to analyze the reaction curve as the absorbance change of the chromogenic product or substrate thereof with no disturbing absorbance to determine the initial rate; when the action of an enzyme to be measured is interfered by substrates and/or products of itself and/or other enzymes in the reaction system, a group of the differential rate equations that describe the kinetics of the reaction system is numerically integrated for fitting to the reaction curve as the absorbance change of the chromogenic product or substrate of the enzyme to be measured with no disturbing absorbance of chromogenic products and chromogenic substrates in the reaction system, to estimate the maximum reaction rate thereof, which is used directly as an index of the activity of the enzyme to be measured, or is further converted according to the differential rate equations into an initial rate at the substrate concentration of 93% of the initial one for reflecting the activity of the enzyme to be measured; taking a wavelength that is less than 25 nm away from the difference absorbance peak maximum wavelength of chromogenic product A as λ1, and determining the absorbance at this wavelength as A1, taking a wavelength that is less than 25 nm away from the maximum isoabsorbance wavelength of chromogenic product A as λ2, and determining the absorbance at this wavelength as A2, the calculation of the interference-free absorbance of chromogenic products or substrates is required to solve the following two linear equations in a group based on the linear additivity of absorbances to eliminate the overlapping absorbance of compounds:

$$A_1 = A_{10} + E31 \times P_1 + E34 \times P_2$$

$$A_2 = A_{20} + E32 \times P_1 \pm E35 \times P_2$$

Which is further converted into the following element linear equation group:

$$A_1 = A_{10} + A_{1a} + R33 \times A_{2b}$$

$$A_2 = A_{20} + A_{2b} + R31 \times A_{1a}$$

wherein $$R31 = E32/E31$$

$$R33 = E34/E35$$

in the above equations, $P_1$ is the instantaneous concentration of chromogenic product A; $P_2$ is the instantaneous concentration of chromogenic product B; E31 is the difference molar extinction coefficient of chromogenic product A versus chromogenic substrate A at λ1; E32 is the difference molar extinction coefficient of chromogenic product A versus chromogenic substrate A at λ2; E34 is the difference molar extinction coefficient of chromogenic product B versus chromogenic substrate B at λ1; E35 is the difference molar extinction coefficient of chromogenic product B versus chromogenic substrate B at λ2; $A_1$ is the total instantaneous absorbance at λ1 before correcting overlapped absorbance interference, $A_2$ is the total instantaneous absorbance at λ2 before correcting overlapped absorbance interference; $A_{1a}$ is the net instantaneous absorbance of chromogenic product A at λ1 after correcting overlapped absorbance interference, which equals to the product of $P_1$ times E31, $A_{2b}$ is the net instantaneous absorbance of chromogenic products B at λ2 after correcting overlapped absorbance interference, which equals to the product of $P_2$ times E35; $A_{10}$ is the absorbance of reaction system at λ1 before generating any chromogenic products, which is the background absorbance of the reaction system, equivalent to the sum of the absorbance at λ1 of the reaction system containing all chromogenic substrates at the same concentrations and the absorbance at λ1 of the reaction system containing a sample at the same concentration; $A_{20}$ is the absorbance of reaction system at before generating any chromogenic products, which is the backgrounds absorbance of the reaction system, equivalent to the sum of the absorbance at of the reaction system containing all chromogenic substrates at the same concentrations and the absorbance at of the reaction system containing a sample at the same concentration;

if a substrate or product of some an enzyme in the reaction channel inhibits or activates another enzyme, then the activity of the enzyme being interfered is measured as follows:

Obtaining the interference-free absorbance change curves of two enzymes, and then calculating the concentration change curves of the compounds that causes the interfering effect; differential rate equations containing the interfering effects are numerically integrated to calculate theoretical reaction plots for fitting to the interference-free absorbance change curves of the disturbed enzyme, the maximum reaction rate $V_m$ for the best fitting is the interference-free activity of the enzyme to be measured; according to the differential rate equations of the enzyme bearing interfered, its $V_m$ and 93% of the initial substrate concentration thereof, calculating the initial rate of the enzyme when the reaction is just started and the disturbing compounds do not significantly accumulate yet, to reflect the activity of the enzyme to be measured;

When a chromogenic product of only one enzyme has competitive inhibiting effect on another enzyme, firstly determining the interference-free absorbance change curves $A_{1a}$ and $A_{2b}$ of chromogenic product A and chromogenic product B at λ1 and λ2, respectively; assigning the initial concentration of chromogenic substrate A to C1, and the initial concentration of chromogenic substrate B to C2; for the conversion of $V_{mB}$ into the initial rate, assigning the maximum reaction rate of enzyme B to $V_{mB}$, the presetted concentration of the chromogenic substrate B as 93° A that of $C_2$, the Michaelis constant of enzyme B for chromogenic substrate B to $K_{mB}$; if chromogenic product A competitively inhibits enzyme B with a competitive inhibition constant of $K_{ia}$, then the rate equation of enzyme B is:

$$\frac{dA}{C_2 \times E_{34}} = \frac{V_{mB} \times dt}{K_{mB} \times (1 + A_{1a}/K_{ia}/E_{31}) + C_2}$$

The above equation is integrated on time from 0 to t to obtain $$\frac{1}{C_2 \times E_{34}} \times \int_0^t dA_{2b} = V_{mB} \times \int_0^t \frac{1}{K_{mB} \times (1 + A_{1a}/K_{ia}/E_{31}) + C_2} \times dt$$

the integration term on the left side is the net absorbance change of chromogenic product B between reaction time t and reaction time 0; the integration term on the right side of the equation is a numerical integration by taking the concentration of chromogenic product A during dt as a constant, that is to calculate $$x = \frac{1}{K_{mB} \times (1 + A_{1a}/K_{ia}/E_{31}) + C_2}$$

take dt as Δt, calculate the x at each recorded timepoint, sum all of the x and then subtract the x at the starting point and the end point to obtain sumx, $V_{mB}$ is calculated according to the following formula, and the noninterfering initial rate s2 is obtained according to the differential kinetic equations thereof;

$$V_{mB} = \int_0^t dA_{2b}/(C_2 \times E_{34} \times \text{sum}x \times \Delta t)$$

$$s_2 = 0.93 \times C_2 \times V_{mB}/(K_{mB} + 0.93 \times C_2)$$

In the above calculating formula, the stoichiometric relationship for converting chromogenic substrate A into chromogenic product A by enzyme A is 1:1, the stoichiometric relationship for converting chromogenic substrate B into chromogenic product B by enzyme B is also 1:1.

When the product(s) of enzyme A exhibit(s) different inhibition types on enzyme B, a different Michaelis-type rate equation of enzyme B is obtained but the numerical integration process is similar, and 93% A C2 is still used as the preset substrate level for deriving s2;

Further, for simultaneously measuring the activities of two kinds of enzymes in single channel through concomitantly monitoring two wavelength absorbances, the present invention has the following features:

In step a, the combination of chromophore A and chromophore B is selected as follows: the maximum isoabsorbance wavelength Y1 of chromogenic product A equals to or is less than 5 nm away from the difference absorbance peak maximum wavelength X2 of chromogenic product B;

In step c, after selecting the difference absorbance peak maximum wavelength X1 of product A as $\lambda 1$, selecting the measuring wavelength $\lambda 2$ as follows: if the difference of the molar extinction coefficients of chromogenic product B versus chromogenic substrate B at the maximum isoabsorbance wavelength Y1 of chromogenic product A is higher than 30% of that at the difference absorbance peak maximum wavelength X2 of chromogenic product B, selecting the maximum isoabsorbance wavelength Y1 of chromogenic product A as $\lambda 2$, otherwise, taking the difference absorbance peak wavelength of chromogenic product B that is nearest to the maximum isoabsorbance wavelength Y1 of chromogenic product A as $\lambda 2$, or a wavelength that is near to the difference absorbance peak wavelength of chromogenic product B and gives the differences of the molar extinction coefficients of other chromogenic products versus their corresponding chromogenic substrates less than 20% of the difference of the molar extinction coefficients of chromogenic product B versus chromogenic substrate B as $\lambda 2$, to measure the absorbance of chromogenic product B;

In step e, it is required to determine R31 as the correcting coefficient of the absorbance interference of chromogenic product A; when determining R31, only the group of all chromogenic substrates that are required for the action of enzyme A is used without the addition of any chromogenic substrates for the actions of other enzymes to be measured, to make the reaction system have no absorbance at the measuring wavelengths $\lambda 1$ and $\lambda 2$ brought about by chromogenic substrate B and chromogenic product B, the absorbance of the reaction channel at the two selected measuring wavelengths are measured concomitantly, till the absorbance changing at $\lambda 2$ is greater than 0.005 or the absorbance changing at $\lambda 1$ is greater than 0.500; taking the absorbance at $\lambda 1$ as x-coordinate, the absorbance at $\lambda 2$ as y-coordinate for regression analysis gives the slope of the obtained regression line as the correcting coefficient R31;

In step e, it is required to determine the R33 as the correcting coefficient of the absorbance interference of chromogenic product B; when determining R33, only the group of all chromogenic substrates that are required for the action of enzyme B is used without the addition of any chromogenic substrates for the actions of other enzymes to be measured, to make the reaction system have no absorbance at the measuring wavelengths $\lambda 1$ and $\lambda 2$ brought about by chromogenic substrate A or chromogenic product A, the absorbance changing of the reaction channel at the two selected measuring wavelengths are simultaneously measured, till the absorbance changing at $\lambda 2$ is greater than 0.500 or the absorbance changing at $\lambda 1$ is greater than 0.005; taking the absorbance at $\lambda 2$ as x-coordinate, the absorbance at $\lambda 1$ as y-coordinate to do regression analysis gives the slope of the obtained regression line as correcting coefficient R33.

Further, for simultaneously measuring the activities of two kinds of enzymes through concomitantly monitoring two wavelength absorbances in single channel:

the chromogenic substrate corresponding to enzyme A comprises 4-nitrophenyl acetate having the maximum isoabsorbance wavelength between 310 and 330 nm upon hydrolysis, 4-nitrophenylphosphate, 4-nitrophenylsulphate, 4-nitrophenyl-$\beta$-D-galactoside and $\gamma$-glutamyl-4-nitroaniline having the maximum isoabsorbance wavelengths between 330 and 350 nm upon hydrolysis, 5-mercapto-2-nitrophenylacetic acid and 5-mercapto-2-nitrobenzoic acid having the maximum isoabsorbance wavelengths between 350 and 370 nm upon reduction of their disulfide bonds by corresponding sulfhydryl groups released from chromogenic substrates under the action of enzymes; the chromogenic substrate B of enzyme B corresponding to the chromogenic substrate A of this kind of enzyme A are mainly natural chromogenic substrates, including nicotinamide adenine dinucleotide and nicotinamide adenine dinucleotide phosphate;

the enzyme A corresponding to chromogenic substrate A comprises, but is not limited to, arylesterase, phosphatase, sulphatase, $\gamma$-glutamyltransferase, amidase corresponding to natural amino acid $\alpha$-carboxyl and glycosidase; enzyme B corresponding to this kind of enzyme A comprises, but not limited to, lactate dehydrogenase LDH, malate dehydrogenase MDH, LDH coupling alanine aminotransferase and MDH coupling aspartate aminotransferase.

Further, for simultaneously measuring the activities of three kinds of enzymes through concomitantly monitoring three wavelength absorbances in single channel by the present inventions, in step a, the three enzymes to be measured are named as enzyme A, enzyme B, and enzyme C, the required chromogenic substrates are chromogenic substrate A, chromogenic substrate B and chromogenic substrate C, respectively, which generate, under the action of the corresponding enzymes, chromogenic products, which are denoted as chromogenic product A, chromogenic product B and chromogenic product C, respectively; the combinations of these chromogenic substrates with chromogenic products meet the following criteria: (1) the difference absorbance peak maximum wavelength of chromogenic product A is X1 and nearest to the infrared end, the difference absorbance peak maximum wavelength of chromogenic product C is X3 and nearest to the UV end, the difference absorbance peak maximum wavelength of chromogenic product B is X2 and locates between X1 and X3, the distances between any pairs among X2 and X1 and X3 are all greater than 30 nm and preferably as far as possible; (2) the maximum isoabsorbance wavelength of chromogenic product A is Y1 and the second maximum isoabsorbance wavelength is Ys; the maximum isoabsorbance wavelength at which chromogenic substrate B generates chromogenic product B is Y2, and preferably as far as possible away from Y1, but as near as possible to Ys; (3) the distance between Y1 and X2 is less than 25 nm, and preferably as shorter as possible; the distances any pairs among Y2 and Ys and X3 are all less than 25 nm and preferably as short as possible;

For simultaneously measuring the activities of three kinds of enzymes through concomitantly monitoring three wavelength absorbances in single channel by the present inventions by the present invention, in step b, simultaneously initiating a reaction of three kinds of enzymes with chromogenic substrate A, chromogenic substrate B and chromogenic substrate C in a single channel, to obtain the corresponding chromogenic product A, chromogenic product B and chromogenic product C;

For simultaneously measuring the activities of three kinds of enzymes through concomitantly monitoring three wavelength absorbances in single channel by the present inventions by the present invention, in step c, taking the wavelength at the difference absorbance peak maximum wavelength X1 of chromogenic product A or within a distance less than 25 nm to it as λ1 to determine the absorbance of chromogenic product A, selecting a wavelength equal to or within a distance less than 25 nm to the maximum isoabsorbance wavelength Y1 of chromogenic product A as λ2 to determine the absorbance of chromogenic product B, selecting a wavelength equal to or within a distance less than 25 nm to the maximum isoabsorbance wavelength Y2 of chromogenic product B as λ3 to determine the absorbance of chromogenic product C;

For simultaneously measuring the activities of three kinds of enzymes through concomitantly monitoring three wavelength absorbances in single channel by the present inventions by the present invention, in step d, swift alteration of wavelengths realizes the simultaneous measurement of three wavelength absorbances to monitor the reaction processes of the three kinds of enzymes to be measured in a single reaction system or channel;

For simultaneously measuring the activities of three kinds of enzymes through concomitantly monitoring three wavelength absorbances in single channel by the present inventions by the present invention, in step e, the calculation of the interference-free absorbance of chromogenic products or substrates is required to solve the following three-element linear equations in a group based on the linear additivity property of absorbances to eliminate the overlapping absorbance of multiple compounds:

$$A_1 = A_{10} + A_{1a} + R33 \times A_{2b} + R35 \times A_{3c}$$

$$A_2 = A_{20} + A_{2b} + R31 \times A_{1a} + R36 \times A_{3c}$$

$$A_3 = A_{30} + A_{3c} + R32 \times A_{1a} + R34 \times A_{2b}$$

$$R31 = E32/E31$$

$$R32 = E33/E31$$

$$R33 = E34/E35$$

$$R34 = E36/E35$$

$$R35 = E37/E39$$

$$R36 = E38/E39$$

In the above formula, $A_1$ is the instantaneous absorbance at λ1 before correcting absorbance interference, $A_2$ is the instantaneous absorbance at λ2 before correcting absorbance interference $A_3$ is the instantaneous absorbance at λ3 before correcting absorbance interference, $A_{1a}$ is the net instantaneous absorbance of chromogenic product A at λ1 after correcting absorbance interference, $A_{2b}$ is the net instantaneous absorbance of chromogenic product B at λ2 after correcting absorbance interference, $A_{3c}$ is the net instantaneous absorbance of chromogenic product C at λ3 after correcting absorbance interference; $A_{10}$ is the absorbance of reaction system at λ1 before generating any chromogenic products, $A_{20}$ is the absorbance of reaction system at λ2 before generating any chromogenic products, $A_{30}$ is the absorbance of reaction system at λ3 before generating any chromogenic products; E31 is the difference molar extinction coefficient of chromogenic product A versus chromogenic substrate A at λ1, E32 is the difference molar extinction coefficient of chromogenic product A versus chromogenic substrate A at λ2, E33 is the difference molar extinction coefficient of chromogenic product A versus chromogenic substrate A at λ3; E34 is the difference molar extinction coefficient of chromogenic product B versus chromogenic substrate B at λ1, E35 is the difference molar extinction coefficient of chromogenic product B versus chromogenic substrate B at λ2, E36 is the difference molar extinction coefficient of chromogenic product B versus chromogenic substrate B at λ3; E37 is the differential molar extinction coefficient of chromogenic product C versus chromogenic substrate C at the measuring wavelength λ1, E38 is the difference molar extinction coefficient of chromogenic product C versus chromogenic substrate C at the measuring wavelength λ2, E39 is the difference molar extinction coefficient of chromogenic product C versus chromogenic substrate C at the measuring wavelength λ3; in the above formula, the stoichiometric relationship of converting chromogenic substrate A into chromogenic product A is 1:1; the stoichiometric relationship of converting chromogenic substrate B into chromogenic product B is 1:1; the stoichiometric relationship of converting chromogenic substrate C into chromogenic product C is 1:1;

Further, for simultaneously measuring the activities of three kinds of enzymes through concomitantly monitoring three wavelength absorbances in single channel by the present inventions, in step e, it is required to determine R31 and R32 as correcting coefficients of the absorbance disturbing of chromogenic product A; when determining, only all chromogenic substrates of enzyme A is used without using any chromogenic substrates for other enzymes to be measured, make the reaction system has no absorbance at the measuring wavelengths λ1, λ2 and λ3 brought about by chromogenic substrate B, chromogenic product B, chromogenic substrate C or chromogenic product C, simultaneously measuring the absorbance changing in the reaction channel at the three measuring wavelengths, till both the absorbance changings at λ2 and λ3 are greater than 0.005 or the absorbance changing at λ1 is greater than 0.500; take the absorbance at λ1 as x-coordinate, the absorbance at λ2 and λ3 as y-coordinate to do regression analysis, the slope of the obtained regression line of the absorbance changing at λ2 is correcting coefficient R31, the slope of the obtained regression line of the absorbance changing at λ3 is correcting coefficient R32;

For simultaneously measuring the activities of three kinds of enzymes through concomitantly monitoring three wavelength absorbances in single channel by the present inventions, in step e, it is required to determine R33 and R34 as correcting coefficients of the absorbance disturbing of chromogenic product B; when determining, only all chromogenic substrates of enzyme B is used without using any chromogenic substrates for other enzymes to be measured, make the reaction system has no absorbance at the measuring wavelengths λ1, λ2 and λ3 brought about by chromogenic substrate A, chromogenic product A, chromogenic substrate C or chromogenic product C, simultaneously measuring the absorbance changing in the reaction channel at the three measuring wavelengths, till both the absorbance changings at λ2 and λ3 are greater than 0.005 or the absorbance changing at λ1 is greater than 0.500; take the absorbance at λ2 as x-coordinate, the absorbance at λ1 and λ3 as y-coordinate to do regression analysis, the slope of the obtained regression line of the absorbance changing at λ1 is correcting coefficient R33, the slope of the obtained regression line of the absorbance changing at λ1 is correcting coefficient R34;

For simultaneously measuring the activities of three kinds of enzymes through concomitantly monitoring three wavelength absorbances in single channel by the present inventions, in step e, it is required to determine R35 and R36 as correcting coefficients of the absorbance disturbing of chromogenic product C; when determining, only all chromogenic substrates of enzyme C is used without using any chromogenic substrates for other enzymes to be measured, make the reaction system has no absorbance at the measuring wavelengths λ1, λ2 and λ3 brought about by chromogenic substrate A, chromogenic product A, chromogenic substrate B or chromogenic product B, simultaneously measuring the absorbance changing in the reaction channel at the three measuring wavelengths, till both the absorbance changings at λ2 and λ1 are greater than 0.005 or the absorbance changing at λ3 is greater than 0.500; take the absorbance at λ3 as x-coordinate, the absorbance at λ1 and λ2 as y-coordinate to do regression analysis, the slope of the obtained regression line of the absorbance changing at λ1 is correcting coefficient R35, the slope of the obtained regression line of the absorbance changing at λ2 is correcting coefficient R36;

For simultaneously measuring the activities of three kinds of enzymes through concomitantly monitoring three wavelength absorbances in single channel by the present inventions, in step a, the combination of chromogenic substrates is selected according to the following principle: the used chromogenic substrate A, chromogenic substrate B and chromogenic substrate C make the maximum isoabsorbance wavelength Y1 of chromogenic product A equal to or is less than 5 nm away from the difference absorbance peak maximum wavelength X2 of chromogenic product B, the maximum isoabsorbance wavelength Y2 of chromogenic product B and the second maximum isoabsorbance wavelength Ys of chromogenic products A and the difference absorbance peak maximum wavelength X3 of chromogenic product C equal to each other or the distances between or among them are not greater than 5 nm;

For simultaneously measuring the activities of three kinds of enzymes through concomitantly monitoring three wavelength absorbances in single channel by the present inventions, in step c, after selecting the difference absorbance peak maximum wavelength X1 of chromogenic product A as λ1, the other two measuring wavelength λ2 and λ3 are selected according to the following principles: when the difference of the molar extinction coefficients of chromogenic product B versus chromogenic substrate B at the maximum isoabsorbance wavelength Y1 of chromogenic product A is higher than 30% of the difference of the molar extinction coefficients of the chromogenic product B versus chromogenic substrate B at the difference absorbance peak maximum wavelength X2, select Y1 as the measuring wavelength λ2, otherwise, selecting the difference absorbance peak wavelength of chromogenic product B nearest to the maximum isoabsorbance wavelength Y1 of chromogenic product A as λ2, or a wavelength that is near to the difference absorbance peak wavelength of chromogenic product B and gives the differences of the molar extinction coefficients of all the other chromogenic products versus their corresponding chromogenic substrates less than 20% of the difference of the molar extinction coefficients of chromogenic product B versus chromogenic substrate B as 22, to measure the absorbance of chromogenic product B; if the difference of the molar extinction coefficients of chromogenic product C versus chromogenic substrate C at the second maximum isoabsorbance wavelength Ys of chromogenic product A or at the maximum isoabsorbance wavelength Y2 of chromogenic product B and chromogenic substrate B is higher than 30% of the difference of the molar extinction coefficients of chromogenic product C versus chromogenic substrate C at their difference absorbance peak maximum wavelength X3, select Y2 or Ys as λ3 to measure the absorbance of chromogenic product C, otherwise, selecting a wavelength that is nearest to the maximum isoabsorbance wavelength Y2 of chromogenic product B or the second maximum isoabsorbance wavelength Ys of chromogenic product A as λ3, or a wavelength that is near to the difference absorbance peak maximum wavelength of chromogenic product C and gives the differences of the molar extinction coefficients of all of the other chromogenic products versus their corresponding chromogenic substrates less than 20% of the difference of the molar extinction coefficients of chromogenic product C versus chromogenic substrate C as λ3, to measure the absorbance of chromogenic product C;

For simultaneously measuring the activities of three kinds of enzymes through concomitantly monitoring three wavelength absorbances in single channel by the present inventions, chromogenic substrate A corresponding to enzyme A comprises 4-nitro-1-naphthylphosphate which upon hydrolysis has two isoabsorbance wavelengths that locate at 315 to 335 nm and 395 to 415 nm, respectively, 4-nitro-1-naphthylsulphate which upon hydrolysis has two isoabsorbance wavelengths that locate at 315 to 335 nm and 395 to 415 nm, 4-nitro-1-naphthylacetate which upon hydrolysis has two isoabsorbance wavelengths that locate at 310 to 330 nm and 375 to 395 nm, 4-nitro-1-naphthyl-β-D-galactoside which upon hydrolysis has two isoabsorbance wavelengths that locate at 320 to 345 nm and 390 to 410 nm, 4-nitro-1-(N-lysyl) naphthylamide which upon hydrolysis has the maximum isoabsorbance wavelength at 385 to 410 nm, this chromogenic substrate A generates, under the action of enzyme A, 4-nitro-1-naphthol or 4-nitro-1-naphthylamine or derivatives thereof as chromogenic product A; chromogenic substrates B corresponding to this chromogenic substrate A is mainly 4-nitrophenol or 4-nitroaniline derivatives, which generates, under the action of the corresponding enzyme B, chromogenic product B which are 4-nitrophenol or 4-nitroaniline or 4-nitrophenylthiol; chromogenic substrate C corresponding to this chromogenic substrate A and chromogenic substrate B comprises nicotinamide adenine dinucleotide and nicotinamide adenine dinucleotide phosphate;

For simultaneously measuring the activities of three kinds of enzymes through concomitantly monitoring three wavelength absorbances in single channel by the present inventions, enzyme A corresponding to chromogenic substrate A comprises, but is not limited to, arylesterase, phosphatase, sulphatase, γ-glutamyltransferase, amidase and glycosidase corresponding to peptidase acting on amides of α-carboxyl group of natural amino acid; enzyme B corresponding to chromogenic substrate B comprises the other hydrolase other than the selected enzyme A but still belonging to hydrolytic enzymes; enzyme C corresponding to chromogenic substrate C comprises, but is not limited to, lactate dehydrogenase LDH, malate dehydrogenase MDH, LDH coupling alanine aminotransferase and MDH coupling aspartate aminotransferase.

The advantages of the present invention include (a) the use of multiple wavelength absorbances for simultaneously measuring the activities of multiple kinds of enzymes in single reaction channel, (b) the development of the new principles for both the combination and design of a group of required chromogenic substrates, (c) a new data processing approach for eliminating the interference of overlapped absorbance of involved substances, all of which are based on both the linear additivity of absorbances of involved substances bearing negligible interactions and the isoabsorbance wavelengths of chromogenic substrates and their corresponding chromogenic products under the actions of enzymes to be measured, and a way to solve interfering actions of involved the substrates and products of different enzymes to be measured, to realize the simultaneous measurement of the activities of multiple kinds of enzymes in single channel through concomitantly monitoring multiple wavelength absorbances; the present invention is applicable for the simultaneous measurement of the activities of multiple kinds of enzymes from the same biological samples, enzyme-labeled simultaneous measurement of multiple components, the simultaneous screening of inhibitors against multiple enzyme targets; the present invention is applicable in clinical biochemical analyses, clinical laboratory immunoassays, health laboratory analyses, the screening of enzyme inhibitors, and basical research works needing such a special enzymatic analysis method.

There are the following special situations needing considerations with the present invention method for simultaneously measuring the activities of multiple kinds of enzymes in single reaction channel. The classical initial rate method analyzes just absorbance data of chromogenic products for the initial rate reaction at the beginning of the reaction of an enzyme, i.e., those for linear increase in absorbance of a chromogenic product. There is a limited range for the monitoring of the absorbances with any spectrophotometer. The use of the maximal isoabsorbance wavelength of Y1 of chromogenic substrate A as $\lambda 2$ for monitoring the absorbance of chromogenic product B effectively reduces the potential interference from the overlapped absorbances of substrate A and product A of enzyme A, but the absorbance of chromogenic substrate A at Y1 or $\lambda 2$ greatly increases the background absorbance; there should be some limitations on the absorbance of chromogenic substrate A at Y1 or $\lambda 2$ and the concentrations of chromogenic substrate A so that there can be a sufficient range to monitor the absorbance of chromogenic product B. At limited levels of chromogenic substrate A, the upper limit for the measurement of classical initial rates of enzyme A will become small. To increase the upper limit for the assay of classical initial rates of enzyme A, the integration strategy for the measurement of enzyme activities can be utilized, which determines both the calculated initial rates via kinetic analysis of reaction process and the classical initial rates; this new intergration strategy is not the intellectual property of the present invention, but the intellectual property of the issued patent of ZL 200710093081.4 in China; when such an integration strategy is used, it is the crossing section of ZL 200710093081.4 and this invention.

The present invention provides a new methodology for simultaneously measuring the activities of multiple kinds of enzymes in single channel through concomitantly monitoring multiple wavelength absorbances to record reaction processes of multiple enzymes, it relies on the screening of the combination of chromogenic substrates, the selection of the combination of wavelengths for monitoring absorbances, swift alteration of wavelengths to concomitantly monitor the changes of multiple wavelength absorbances, an approach of data processing for the elimination of the interference of the overlapped absorbances, a way to eliminate the interfering effects of substrates and products on the actions of the enzymes to be measured (FIG. 1).

The representative steps for simultaneously measuring the activities of two kinds of enzymes in single channel through concomitantly monitoring two wavelength absorbances include:

(1) Screening for chromogen A and chromogen B to prepare chromogenic substrates of two enzymes to be measured, and there are the following criteria for the two chromogens: (a) X1 as the difference absorbance peak maximum wavelength of chromogenic product A versus chromogenic substrate A is the doer to the infrared end, X2 as the difference absorbance peak maximum wavelength of chromogenic product B versus chromogenic substrate B is closer to the UV end, there should be a distance of longer than 30 nm between X1 and X2 and the longer distance is preferable; (b) Y1 as the maximal isoabsorbance wavelength of chromogenic substrate A and chromogenic product A should be within 25 nm from X2, and the shorter distance between Y1 and X2 is preferred (FIG. 1 and Table 1), (c) an ideal pair of chromogen A and chromogen B should produce Y1 equal to X2 or within 5 nm from X2;

(2) Synthesizing two chromogenic substrates; the process and techniques for the syntheses of those chromogenic substrates may be the properties claimed in other patent applications;

(3) Initiating synchronously the reactions of two enzymes in single reaction channel on the two selected chromogenic substrates, to monitor the absorbance of chromogenic product B at Y1 as $\lambda 2$ while to monitor the absorbance of chromogenic product A at X1 as $\lambda 1$; the reaction processes of two enzymes are recorded through concomitantly monitoring two wavelength absorbances via swift alteration of two selected wavelengths;

(4) Developing an approach of data processing for eliminating the overlapped absorbances of substances to derive an interference-free absorbance change curve of each enzyme;

(5) Developing a way of data processing to eliminate the interfering effects of substrates and products on actions of two enzymes to be measured, by analyzing the interference-free absorbance change curve of the chromogenic substrate or product of each enzyme for deriving the error-free maximal reaction rate;

The aforementioned approach for the elimination of the overlapped absorbance of substrates and products described in the step (4) is independent of both the selection of two wavelengths for concomitantly monitoring two wavelength absorbances and the combination of two chromogenic substrates; however, when the criterion (c) described in the step (1) is not satisfied, the limit of quantification of the activity of enzyme B will be worse than that for separate assay; when both an ideal pair of chromogenic substrates according to the criterion (c) described in the step (1) is used and the two wavelengths for concomitantly monitoring two wavelength absorbances are selected according to the description in step (3), the performance of enzyme activity assay by the present invention is comparable to that by separate assay.

Figure 2:
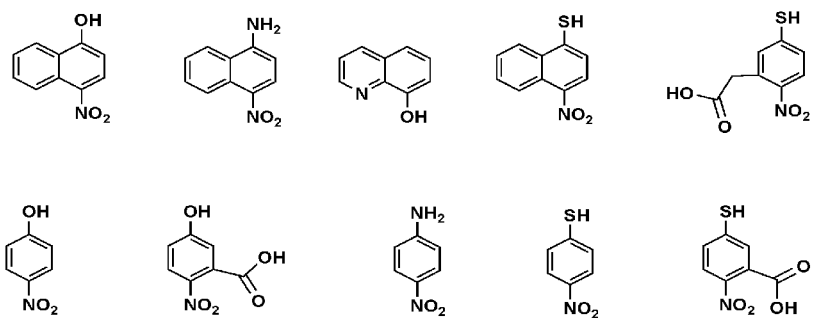

For enzyme activity assay, the principal chromogenic products are 4-nitrophenol, 4-nitroaniline and their derivatives, and NADH plus NADPH (FIG. 2). The wavelengths for monitoring the absorbance of the natural chromogenic products NADH and NADPH vary from 320 to 355 nm. The mammal isoabsorbance wavelengths of 4-nitrophenol, 4-nitroaniline and their derivatives under the actions of proper enzymes vary from 310 nm to 350 nm while the difference absorbance peak maximum wavelength is close to 400 nm; under the actions of proper enzymes, there are usually negligible changes of the absorbances at the maximal isoabsorbance wavelengths of 4-nitrophenol, 4-nitroaniline and their derivatives even their absorbance at 400 nm is over 1.0 (FIG. 3). Therefore, the selection of the derivatives of 4-nitrophenol and 4-nitroaniline as chromogenic substrate A while NADH or NADPH as chromogenic product B, the assay of the absorbance of chromogenic product B by the selection of the maximal isoabsorbance wavelength Y1 as $\lambda 2$ tolerates negligible interference from the changes of concentrations of chromogenic substrate A and chromogenic product A. As a result, chromogenic substrates derived from 4-nitrophenol and 4-nitroaniline can be combined with NADH or NADPH for simultaneously measuring the activities of two enzymes in single channel.

At pH 7.4, the molar absorption coefficient of 4-nitronaphthol at 450 nm is about $2.3 \times 10^4$ $(mol/L)^{-1} \times cm^{-1}$, that of 4-nitrophenol at 405 nm is about $1.1 \times 10^4$ $(mol/L)^{-1} \times cm^{-1}$; calf intestinal alkaline phosphatase (CIAP) is widely used for immunoassays; when 4-nitronaphthylphosphate (4NNPP) is used as the chromogenic substrate, CIAP has a Michaelis constant of about 10 µmol/L; CIAP has a specific activity on 4NNPP accounting for about 40% of that on 4-nitrophenylphosphate; considering the difference in molar absorption coefficients, the limit of quantification for the assays of the activities of CIAP with both 4NNPP and 4-nitrophenylphosphate should be comparable to each other. As a result, 4NNPP can be chromogenic substrate A to measure activity of CIAP (FIG. 4), which in combination with 4-nitrophenyl-β-galactoside for the assay of β-D-galactosidase (β-Gal), or in combination with any of other enzymes acting on its chromogenic substrates to release 4-nitrophenol, can be utilized for immunoassays to realize simultaneously measuring two components in single channel through concomitantly monitoring two wavelength absorbance. Moreover, glycosidases usually exhibit high specificity, compatibility of their optimum reaction pH and buffers, and tolerate no strong interference on actions from their substrates and products; with the use of 4-nitronaphthyl-β-D-galactoside and 4-nitrophenyl-α-D-glucoside as chromogenic substrates, β-galactosidase and α-glucosidase can be combined for simultaneous ELISAs of two components in single channel; however, the optimum combination of the wavelengths should be 400 nm plus 460 or 450 nm, devalued with microplate readers equipped with filters countering on 405 nm.

The methods developed in this invention for both the processing of the overlapped absorbencies and the processing of the interference with enzyme actions of involved substances are universally applicable as long as chromogenic substrates and chromogenic products are stable enough. The critical prerequisites for the practice of this invention are the screening of the combination of chromogenic substrates to provide the limits of quantification, sensitivity and linear range for quantification of the activities of two enzymes comparable to those by separate assays. The representative combination of chromogenic substrates for this invention includes water-soluble derivatives of 4-nitrophenol and 4-nitronaphthol as chromogenic substrates of hydrolytic enzymes, chromogenic substrates derived from 4-nitroaniline plus NADH or NADPH.

FIGURE CAPTIONS AND LEGENDS

For simplicity, the following abbreviations are used as labels in figures.

IAW: an isoabsorbance wavelength; MIAW: the maximal isoabsorbance wavelength;

MDAW: the difference absorbance peak maximum wavelength.

The following sections utilized supporting figures to illustrate the practice of this invention.

FIG. 1 Simultaneous assays of the activities of two enzymes in single reaction channel through the concurrent assays of absorbance at multiple wavelengths FIG. 2 Common chromogens and chromogenic substrates for the assays of enzyme activities FIG. 3 The spectral properties of chromogenic substrates derived from 4-nitrophenol and 4-nitroaniline under the actions of common enzymes 3-a. Changes of the absorbance spectra of 0.50 mmol/L 4-nitrophenyl-β-D-galactoside plus *Escherichia coli* β-D-galactosidase (Sigma G4155) in 0.050 mol/L Tris-HCl at pH 7.4

3-b. Changes of the absorbance spectra of 0.50 mmol/L γ-glutamyl-aniline plus the homogenate of rabbit kidney in 0.050 mol/L Tris-HCl at pH 7.4

3-c. Changes of the absorbance spectra of 0.50 mmol/L 4-nitrophenylphosphate plus CIAP (Sigma P0114) in 0.050 mol/L Tris-HCl at pH 7.4

3-d. Changes of the absorbance spectra of 0.50 mmol/L 4-nitrophenylphosphate plus CIAP (Sigma P0114) in 0.050 mol/L Tris-HCl at pH 8.5

3-e. Changes of the absorbance spectra of 0.50 mmol/L acetylthioncholine and Ellman reagent 5,5'-Dithio-bis-(2-nitrobenzoic acid) (DTNB) plus acetylcholinesterase (Sigma C2888) in 0.050 mol/L Tris-HCl at pH 7.4

3-g. Changes of the absorbance spectra of 0.50 mmol/L acetylthioncholine and 5,5'-dithio-bis-(2-nitropnenylacetic acid) (DTNA) plus acetylcholinesterase (Sigma C2888) in 0.050 mol/L Tris-HCl at pH 7.4

3-h. Changes of the absorbance spectra of 0.50 mmol/L acetylthioncholine and Ellman reagent 5,5'-Dithio-bis-(2-nitrobenzoic acid)) (DTNB) plus acetylcholinesterase (Sigma C2888) in 0.050 mol/L Tris-HCl at pH 8.5

3-f. Changes of the absorbance spectra of 0.50 mmol/L acetylthioncholine and 5,5'-dithio-bis-(2-nitropnenylacetic acid) (DTNA) plus acetylcholinesterase (Sigma C2888) in 0.050 mol/L Tris-HCl at pH 8.5

FIG. 4 The spectral properties of chromogenic substrates derived from 4-nitronaphthol under the actions of common enzymes 4-a. Changes of absorbance spectra of 0.25 mmol/L (4-nitro-1-naphthyl)-β-D-galactoside plus β-D-galactosidase (Sigma G4155) in 0.050 mol/L Tris-HCl at pH 7.4

4-b. Changes of absorbance spectra of 0.50 mmol/L 4-nitro-1-naphthylphosphate plus CIAP (Sigma P0114) in 0.050 mol/L Tris-HCl at pH 7.4

4-c. Changes of absorbance spectra of 0.50 mmol/L 4-nitro-1-naphthylsulfate plus snail arylsulfatase (Sigma S9626) in 0.050 mol/L Tris-HCl at pH 7.4

FIG. 6 simultaneous assays of γ-glutamyltransferase GGT and lactic acid dehydrogenase LDH in rabbit kidney homogenate 6-a. The use of GGT chromogenic substrate alone to estimate the correction factor R31 for the overlapped absorbance of 4-nitroaniline at 344 nm Regression analysis gave $\Delta A_{344} = 0.0289 \times \Delta A_{405} + 0.0167$, $R^2 > 0.902$, $R31 = 0.0289$.

6-b. The use of LDH chromogenic substrate alone to estimate the correction factor R33 for the overlapped absorbance of NADH at 405 nm Regression analysis gave $\Delta A_{405} = 0.0088 \times \Delta A_{344} - 0.0002$, $R^2 > 0.993$, $R31 = 0.0088$.

This overlapped absorbance was too small to be corrected; the comparison of analyses of experimental data after correction to those without correction gave no difference.

6-c. Comparison of the correction effects on GGT activities by simultaneous assays A. before correction, the response of V1 (ΔA/min) to enzyme quantities was nonlinear B. after correction, the response of s1 (ΔA/min) gave $s1 = 2.6565 \times \chi - 0.0061$, $R^2 > 0.996$ C. separate assay of s1(ΔA/min) of GGT, s1=2.6971×χ−0.0059, $R^2$>0.997

6-d. Comparison of the correction effects on LDH by simultaneous assays
- A. before correction, the response of V2 (ΔA/min) to enzyme quantities was nonlinear
- B. after correction, the response of s2 (ΔA/min) gave s2=1.1028×χ+0.0025, $R^2$>0.996
- C. separate assay of s2 (ΔA/min) gave s2=1.1715×χ+0.0016, $R^2$>0.994

FIG. 7 The use of 4-nitro-1-naphthylphosphate and 4-nitrophenyl-β-D-galactoside for simultaneous assays of alkaline phosphatase and β-D-galactosidase 7-a. the use of alkaline phosphate substrate alone to estimate the correction factor of R31 for the overlapped absorbance of 4-nitronaphthol at 405 nm Regression analysis gave $\Delta A_{405}$=−0.015×$\Delta A_{450}$+0.0107, $R^2$>0.88, R31=−0.015.

7-b. the use of β-D-galactosidase substrate alone to estimate the correction factor of R33 for the overlapped absorbance of 4-nitrophenol at 450 nm Regression analysis gave $\Delta A_{450}$=0.1931×$A_{405}$−0.0817, $R^2$>0.999, R33=0.1931.

7-c. Comparison of the correction effects on phosphatase activities by simultaneous assays
- A. before correction, the response of V1 (ΔA/min) to enzyme quantities gave V1=0.7425×χ−0.0003, $R^2$>0.99
- B: after correction, the response of s1 (ΔA/min) gave s1=0.6333×χ−0.0008, $R^2$>0.995
- C: separate assay, the response of S1 (ΔA/min) gave s1=0.6200×χ+0.0009, $R^2$>0.998

7-d. Comparison of the correction effects on β-D-galactosidase activities by simultaneous assays
- A: before correction, the response of V2(ΔA/min) gave V2=0.6267×χ+0.0017, $R^2$>0.993
- B: after correction, the response of s2 (ΔA/min) gave s2=0.6067×χ+0.0023, $R^2$>0.993
- C: separate assay, the response of s2 (ΔA/min) gave s2=0.6133×χ+0.0021, $R^2$>0.998

FIG. 8 Simultaneous competitive ELISAs with penicillin labeled β-D-galactosidase and blenturol label dα-D-glucosidase 8-a. the use of 4-nitro-1-naphthyl-β-D-galactoside alone to estimate the correction factor R31 for the overlapped absorbance of 4-nitro-1-naphthol at 405

Regression analysis gave $\Delta A_{405}$=0.0665×$\Delta A_{450}$+0.0015, $R^2$>0.998, R31=0.0665.

8-b. the use of 4-nitrophenyl-α-D-glucoside alone to estimate the correction factor R33 for the overlapped absorbance of 4-nitro-1-naphthol at 450 nm Regression analysis gave $\Delta A_{450}$=0.1957×$\Delta A_{405}$−0.0874, $R^2$>0.992, R33=0.1957.

8-c. the correction effects on β-D-galactosidase by simultaneous assays
- A. before correction, the response of V1 (ΔA/min) gave V1=2.2871×χ−0.0073, $R^2$>0.997
- B. after correction, the response of s1 (ΔA/min) gave s1=1.9216×χ−0.0034, $R^2$>0.996
- C. separate assay, the response of s1 (ΔA/min) was s1=2.0291×χ−0.0027, $R^2$>0.999

8-d. the correction effects on α-D-glucosidase by simultaneous assays
- A. before correction, the response of V2 (ΔA/min) gave V2=1.9065×χ−0.0123, $R^2$>0.989
- B. after correction, the response of s2(ΔA/min) gave s2=1.7543×χ−0.0124, $R^2$>0.989
- C. separate assay, the response of s2(ΔA/min) was s2=1.7945×χ−0.0118, $R^2$>0.992.

8-e. comparison of binding ratios of the conjugate of penicillin labeled β-D-galactosidase before and after correction by simultaneous ELISA
- A. before correction, binding ratios (%)=−6.4865×Ln(χ)+87.332, $R^2$>0.987
- B. after correction, binding ratios (%)=−6.2685×Ln(χ)+86.886, $R^2$>0.990
- C. separate assay without the use of the substrate of α-D-glucosidase, binding ratios of the conjugate of β-D-galactosidase (%)=−6.8541×Ln(χ)+87.689, $R^2$>0.977

8-f. comparison of binding ratios of the conjugate of clenbuterol labeled α-D-glucosidase before and after the correction by simultaneous ELISA
- A. before correction, binding ratios (%)=−11.3572×Ln(χ)+92.27, $R^2$>0.991
- B. after correction, binding ratios (%)=−12.054×Ln(χ)+93.755, $R^2$>0.955
- C. separate assay without the use of the substrate of β-D-galactosidase, binding ratios of the conjugate of α-D-glucosidase (%)=−13.145×Ln(χ)+104.47, $R^2$>0.990

DETAILED DESCRIPTION OF THE INVENTION

This invention utilizes multiple wavelength absorbances in single channel for simultaneously measuring the activities of multiple kinds of enzymes, which includes the following steps:

a. determining the combination of chromogenic substrates required for simultaneously measuring the activities of multiple kinds of enzymes;

a1 selecting the combination of chromogenic substrates that meets the following criteria according to the specificity of the enzymes to be measured: the selected chromophores can be respectively used to prepare the chromogenic substrates of the enzyme to be measured; in the obtained combination of chromogenic substrates, the difference absorbance peak maximum wavelengths of the chromogenic products formed under the actions of the respective enzyme to be measured with respect to their chromogenic substrates are arranged from large to small to give a one-dimension array, the distance between any two adjacent difference absorbance peak maximum wavelengths of the chromogenic products in the aforementioned array is greater than 30 nm and preferably as far as possible; in the array of the difference absorbance peak maximum wavelengths of the chromogenic products from large to small, except for the chromogenic substrate whose chromogenic product has the difference absorbance peak maximum wavelength nearest to the infrared end, the difference absorbance peak maximum wavelength of each chromogenic product obtained from its chromogenic substrate under the action of the corresponding enzyme is less than 25 nm and preferably as shorter as possible away from the maximum isoabsorbance wavelength of one of the chromogenic substrates in the aforementioned array;

a2 synthesizing corresponding chromogenic substrates of the enzymes to be measured respectively by the chromophores selected in step a1, and using them in combination;

b. in one reaction mixture or enzyme reaction system, that is a single reaction channel, synchronously initiating the specific catalyzed reactions of the multiple kinds of enzymes to be measured with their corresponding chromogenic substrates combined for use as a mixture;

c. selecting a combination of wavelengths for measuring absorbance: taking the chromogenic substrate whose chromogenic product thereof has the difference absorbance peak maximum wavelength nearest to the infrared end as chromogenic substrate A, determining the absorbance of the chromogenic product at the difference absorbance peak maximum wavelength of the chromogenic product of chromogenic substrate A; determining the absorbance of the chromogenic products or chromogenic substrates of the other enzymes whose activities are to be measured at the isoabsorbance wavelengths of the chromogenic substrate A;

d. realizing simultaneous measurement of multiple wavelength absorbances for concomitantly monitoring the reaction processes of multiple kinds of the enzymes to be measured in a single channel through swift alteration of the wavelengths selected in the combination;

e. developing an approach of data processing for eliminating the interference of the overlapped absorbance of chromogens involved in enzyme reactions based on the linear additivity property of absorbances of non-interacting compounds, to obtain an absorbance change curve of the chromogenic product or substrate of each enzyme to be measured after the elimination of the overlapping interference in absorbance spectra; if the action of an enzyme of interest for activity assay is not subject to the interference by the products and substrates of the other enzymes in the reaction system, and the substrate concentration is over three times of a Michaelis constant of the corresponding enzyme, the classical initial rate method is used to analyze the absorbance change curve of the chromogenic product or substrate with no disturbing absorbance to determine the initial rate; if the action of an enzyme to be measured is not disturbed by the products and substrates of the other enzymes in the reaction system, however, the concentration of the used chromogenic substrate is over 5% of a Michaelis constant of the corresponding enzyme but less than three times of the Michaelis constant, the classical initial rate method is integrated with kinetic analysis of reaction process to analyze the reaction curve as the absorbance change of the chromogenic product or substrate thereof with no disturbing absorbance to determine the initial rate; when the action of an enzyme to be measured is disturbed by substrates and/or products of itself and/or other enzymes in the reaction system, a group of the differential rate equations that describe the kinetics of the reaction system is numerically integrated for fitting to the reaction curve as the absorbance change of the chromogenic product or substrate of the enzyme to be measured with no disturbing absorbance of chromogenic products and chromogenic substrates in the reaction system, to estimate the maximum reaction rate thereof, which is used directly as an index of the activity of the enzyme to be measured, or is further converted according to the differential rate equations into an initial rate at the substrate concentration of 93% of the initial one for reflecting the activity of the enzyme to be measured.

In the examples for the practice of the present invention, the difference absorbance peak maximum wavelengths of chromogenic products versus their chromogenic substrates are greater than 300 nm, and the maximal absorbance peak wavelengths of the chromogenic substrates thereof are less than the maximal absorbance peak wavelength of the corresponding chromogenic products, otherwise the rates for the enzymes catalyzing the reversed reaction are determined to reflect the activities of these enzymes; for any two chromogenic substrates whose chromogenic products formed thereof under the actions of the enzymes whose activities are to be measured have the difference absorbance peak maximum wavelengths adjacent to each other in the aforementioned array of the difference absorbance peak maximum wavelengths, when the difference absorbance peak maximum wavelength of the chromogenic product is both closer to the UV end and is equal to or less than 5 nm distance away from the maximal isoabsorbance wavelength of the chromogenic substrate whose chromogenic product has the difference absorbance peak maximum wavelength closer to the infrared end, this two are the preferred combination of chromogenic substrates; in the used combination of all chromogenic substrates, each chromogenic substrate is only converted by the action of one enzyme whose activity is to be measured into the corresponding chromogenic product(s), without being affected or being affected in a negligible way by the any other enzyme in the sample; the expression "without being affected or being effected in a negligible way by the any other enzyme in the sample" herein means when the concentration of the chromogenic substrate corresponding to enzyme I in the sample differ from the Michaelis constant thereof in less than 50%, the specific activity of the any other enzymes in the sample acting on the chromogenic substrate thereof is less than 1% of the specific activity of enzyme I acting on the same chromogenic substrate; in step b, a buffer medium and reaction conditions suitable for the enzyme to be measured to take effect in simultaneously measuring the activities are selected, that is, the buffer medium has a pH from 5.0 to 9.0, and close to the optimum pH for the enzyme to be measured in the sample whose specific activity is the lowest, the used reaction temperature is between 20 and 40° C.

In the examples for the practice of the present invention, said chromogenic substrates comprise natural chromogenic substrates and nonnatural chromogenic substrates; wherein the natural chromogenic substrates comprises nicotinamide adenine dinucleotide and nicotinamide adenine dinucleotide phosphate; nonnatural chromogenic substrates consists of a chromophore and a moiety recognized by enzymes for action, the chromophore comprises, but is not limited to, 4-nitrophenol, 4-nitrobenzenethiol, 4-nitroaniline, 4-nitro-1-naphthol, 4-nitro-1-naphthylthiol, 4-nitro-1-naphthylamine, 2-naphthol, 4-chlorophenol, rosolic acid or the derivatives of these aromatic phenol and/or aromatic amines.

In the examples for the practice of the present invention for simultaneously measuring the activities of two kinds of enzymes in single channel through concomitantly monitoring two wavelength absorbances, in step a, the two enzymes to be measured are named as enzyme A and enzyme B, the required two chromophores are chromophore A and chromophore B, respectively, the corresponding two chromogenic substrates are chromogenic substrate A and chromogenic substrate B, respectively, two chromogenic products producted by the action of the two enzymes to be measured are chromogenic product A and chromogenic product B, respectively, the combination of these chromogenic substrates and chromogenic products is required to meets the following criteria: (1) the difference absorbance peak maximum wavelength X1 of chromogenic product A is closer to the infrared end, the difference absorbance peak maximum wavelength X2 of chromogenic product B is closer to the UV end, the distance between the difference absorbance peak maximum wavelength X2 of chromogenic product B and the difference absorbance peak maximum wavelength X1 of chromogenic product A is greater than 30 nm, and preferably as far as possible; (2) the maximum isoabsorbance wavelength of chromogenic product A is Y1, and is equal to or less than 25 nm distance away from the difference absorbance peak maximum wavelength X2 of chromogenic product B, and the distance is preferably as short as possible;

In steps b, c and d for simultaneously measuring the activities of two kinds of enzymes by the present invention, synchronously initiating the reactions of two kinds of the enzymes from a sample with chromogenic substrate A and chromogenic substrate B in a single reaction channel, to obtain chromogenic product A and chromogenic product B; selecting the difference absorbance peak maximum wavelength X1 of chromogenic product A as λ1 to determine the absorbance of the chromogenic product A, selecting the maximum isoabsorbance wavelength Y1 of chromogenic product A as λ2 to determine the absorbance of chromogenic product B; concomitantly monitoring two wavelength absorbances concurrently records the reaction processes of the two kinds of enzymes to be measured in a single channel by swift alteration of the measuring wavelength;

In step e for simultaneously measuring the activities of two kinds of enzymes by the present invention, an approach for data interpretation to eliminate the interference of the overlapped absorbances of multiple compounds is developed based on the linear additivity of absorbances; taking a wavelength that is less than 25 nm away from the difference absorbance peak maximum wavelength of chromogenic product A as λ1, and determining the absorbance at this wavelength as A1, taking a wavelength that is less than 25 nm away from the maximum isoabsorbance wavelength of chromogenic product A as λ2, and determining the absorbance at this wavelength as A2, the calculation of the interference-free absorbance of chromogenic products or substrates is required to solve the following two linear equations in a group based on the linear additivity of absorbances to eliminate the overlapping absorbance of compounds:

$$A_1 = A_{10} + E31 \times P_1 + E34 \times P_2$$

$$A_2 = A_{20} + E32 \times P_1 \pm E35 \times P_2$$

Which is further converted into the following element linear equation group:

$$A_1 = A_{10} + A_{1a} + R33 \times A_{2b}$$

$$A_2 = A_{20} + A_{2b} + R31 \times A_{1a}$$

Wherein $$R31 = E32/E31$$

$$R33 = E34/E35$$

in the above equations, $P_1$ is the instantaneous concentration of chromogenic product A; $P_2$ is the instantaneous concentration of chromogenic product B; E31 is the difference molar extinction coefficient of chromogenic product A versus chromogenic substrate A at λ1; E32 is the difference molar extinction coefficient of chromogenic product A versus chromogenic substrate A at λ2; E34 is the difference molar extinction coefficient of chromogenic product B versus chromogenic substrate B at λ1; E35 is the difference molar extinction coefficient of chromogenic product B versus chromogenic substrate B at 22; $A_1$ is the total instantaneous absorbance at λ1 before correcting overlapped absorbance interference, $A_2$ is the total instantaneous absorbance at λ2 before correcting overlapped absorbance interference; $A_{1a}$ is the net instantaneous absorbance of chromogenic product A at λ1 after correcting overlapped absorbance interference, which equals to the product of $P_1$ times E31, $A_{2b}$ is the net instantaneous absorbance of chromogenic products B at λ2 after correcting overlapped absorbance interference, which equals to the product of $P_2$ times E35; $A_{10}$ is the absorbance of reaction system at λ1 before generating any chromogenic products, which is the background absorbance of the reaction system, equivalent to the sum of the absorbance at λ1 of the reaction system containing all chromogenic substrates at the same concentrations and the absorbance at λ1 of the reaction system containing a sample at the same concentration; $A_{20}$ is the absorbance of reaction system at λ2 before generating any chromogenic products, which is the backgrounds absorbance of the reaction system, equivalent to the sum of the absorbance at λ2 of the reaction system containing all chromogenic substrates at the same concentrations and the absorbance at λ2 of the reaction system containing a sample at the same concentration;

If a substrate or product of some an enzyme in the reaction channel inhibits or activates another enzyme, then the activity of the enzyme being interfered is measured as follows:

Obtaining the interference-free absorbance change curves of two enzymes, and then calculating the concentration change curves of the compounds that causes the interfering effect; differential rate equations containing the interfering effects are numerically integrated to calculate theoretical reaction plots for fitting to the interference-free absorbance change curves of the disturbed enzyme, the maximum reaction rate $V_m$ for the best fitting is the interference-free activity of the enzyme to be measured; according to the differential rate equations of the enzyme bering interfered, its $V_m$ and 93% of the initial substrate concentration thereof, calculating the initial rate of the enzyme when the reaction is just started and the disturbing compounds do not significantly accumulate yet, to reflect the activity of the enzyme to be measured;

When a chromogenic product of only one enzyme has competitive inhibiting effect on another enzyme, firstly determining the interference-free absorbance change curves $A_{1a}$ and $A_{2b}$ of chromogenic product A and chromogenic product B at λ1 and λ2, respectively; assigning the initial concentration of chromogenic substrate A to C1, and the initial concentration of chromogenic substrate B to C2; for the conversion of $V_{mB}$ into the initial rate, assigning the maximum reaction rate of enzyme B to $V_{mB}$, the presetted concentration of the chromogenic substrate B as 93% that of $C_2$, the Michaelis constant of enzyme B for chromogenic substrate B to $K_{mB}$; if chromogenic product A competitively inhibits enzyme B with a competitive inhibition constant of $K_{ia}$, then the rate equation of enzyme B is:

$$\frac{dA_{2b}}{C_2 \times E_{34}} = \frac{V_{mB} \times dt}{K_{mB} \times (1 + A_{1a}/K_{ia}/E_{31}) + C_2}$$

The above equation is integrated on time from 0 to t to obtain $$\frac{1}{C_2 \times E_{34}} \times \int_0^t dA_{2b} = V_{mB} \times \int_0^t \frac{1}{K_{mB} \times (1 + A_{1a}/K_{ia}/E_{31}) + C_2} \times dt$$

the integration term on the left side is the net absorbance change of chromogenic product B between reaction time t and reaction time 0; the integration term on the right side of the equation is a numerical integration by taking the concentration of chromogenic product A during dt as a constant, that is to calculate $$x = \frac{1}{K_{mB} \times (1 + A_{1a}/K_{ia}/E_{31}) + C_2}$$

take dt as Δt, calculate the x at each recorded timepoint, sum all of the x and then subtract the x at the starting point and the end point to obtain sumx, $V_{mB}$ is calculated according to the following formula, and the noninterfering initial rate s2 is obtained according to the differential kinetic equations thereof;

$$V_{mB} = \int_0^t d A_{2b}/(C_2 \times E_{34} \times \text{sum} x \times \Delta t)$$

$$s_2 = 0.93 \times C_2 \times V_{mB}/(K_{mB} + 0.93 \times C_2)$$

In the above calculating formula, the stoichiometric relationship for converting chromogenic substrate A into chromogenic product A by enzyme A is 1:1, the stoichiometric relationship for converting chromogenic substrate B into chromogenic product B by enzyme B is also 1:1.

When the product(s) of enzyme A exhibit(s) different inhibition types on enzyme B, a different Michaelis-type rate equation of enzyme B is obtained but the numerical integration process is similar, and 93% C2 is still used as the preset substrate level for deriving s2;

In the examples for the practice of the present invention for simultaneously measuring the activities of two kinds of enzymes, the present invention has the following features:

In step a, the combination of chromophore A and chromophore B is selected as follows: the maximum isoabsorbance wavelength Y1 of chromogenic product A equals to or is less than 5 nm away from the difference absorbance peak maximum wavelength X2 of chromogenic product B;

In step c, after selecting the difference absorbance peak maximum wavelength X1 of product A as λ1, selecting the measuring wavelength λ2 as follows: if the difference of the molar extinction coefficients of chromogenic product B versus chromogenic substrate B at the maximum isoabsorbance wavelength Y1 of chromogenic product A is higher than 30% of that at the difference absorbance peak maximum wavelength X2 of chromogenic product B, selecting the maximum isoabsorbance wavelength Y1 of chromogenic product A as λ2, otherwise, taking the difference absorbance peak wavelength of chromogenic product B that is nearest to the maximum isoabsorbance wavelength Y1 of chromogenic product A as λ2, or a wavelength that is near to the difference absorbance peak wavelength of chromogenic product B and gives the differences of the molar extinction coefficients of other chromogenic products versus their corresponding chromogenic substrates less than 20% of the difference of the molar extinction coefficients of chromogenic product B versus chromogenic substrate B as λ2, to measure the absorbance of chromogenic product B;

In step e, it is required to determine R31 as the correcting coefficient of the absorbance interference of chromogenic product A; when determining R31, only the group of all chromogenic substrates that are required for the action of enzyme A is used without the addition of any chromogenic substrates for the actions of other enzymes to be measured, to make the reaction system have no absorbance at the measuring wavelengths λ1 and λ2 brought about by chromogenic substrate B and chromogenic product B, the absorbance of the reaction channel at the two selected measuring wavelengths are measured concomitantly, till the absorbance changing at λ2 is greater than 0.005 or the absorbance changing at λ1 is greater than 0.500; taking the absorbance at λ1 as x-coordinate, the absorbance at λ2 as y-coordinate for regression analysis gives the slope of the obtained regression line as the correcting coefficient R31;

In step e, it is required to determine the R33 as the correcting coefficient of the absorbance interference of chromogenic product B; when determining R33, only the group of all chromogenic substrates that are required for the action of enzyme B is used without the addition of any chromogenic substrates for the actions of other enzymes to be measured, to make the reaction system have no absorbance at the measuring wavelengths λ1 and λ2 brought about by chromogenic substrate A or chromogenic product A, the absorbance changing of the reaction channel at the two selected measuring wavelengths are simultaneously measured, till the absorbance changing at λ2 is greater than 0.500 or the absorbance changing at λ1 is greater than 0.005; taking the absorbance at λ2 as x-coordinate, the absorbance at λ1 as y-coordinate to do regression analysis gives the slope of the obtained regression line as correcting coefficient R33.

In the examples for the practice of the present invention for simultaneously measuring the activities of two kinds of enzymes, the chromogenic substrate corresponding to enzyme A comprises 4-nitrophenyl acetate having the maximum isoabsorbance wavelength between 310 and 330 nm upon hydrolysis, 4-nitrophenylphosphate, 4-nitrophenylsulfate, 4-nitrophenyl-β-D-galactoside and γ-glutamyl-4-nitro aniline having the maximum isoabsorbance wavelengths between 330 and 350 nm upon hydrolysis, 5-mercapto-2-nitrophenylacetic acid and 5-mercapto-2-nitrobenzoic acid having the maximum isoabsorbance wavelengths between 350 and 370 nm upon reduction of their disulfide bonds by corresponding sulfhydryl groups released from chromogenic substrates under the action of enzymes; the chromogenic substrate B of enzyme B corresponding to the chromogenic substrate A of this kind of enzyme A are mainly natural chromogenic substrates, including nicotinamide adenine dinucleotide and nicotinamide adenine dinucleotide phosphate; the enzyme A corresponding to chromogenic substrate A comprises, but is not limited to, arylesterase, phosphatase, sulphatase, γ-glutamyltransferase, amidase corresponding to natural amino acid α-carboxyl and glycosidase; enzyme B corresponding to this kind of enzyme A comprises, but not limited to, lactate dehydrogenase LDH, malate dehydrogenase MDH, LDH coupling alanine aminotransferase and MDH coupling aspartate aminotransferase.

In the examples for the practice of the present invention for simultaneously measuring the activities of three kinds of enzymes, in step a, the three enzymes to be measured are named as enzyme A, enzyme B, and enzyme C, the required chromogenic substrates are chromogenic substrate A, chromogenic substrate B and chromogenic substrate C, respectively, which generate, under the action of the corresponding enzymes, chromogenic products, which are denoted as chromogenic product A, chromogenic product B and chromogenic product C, respectively; the combinations of these chromogenic substrates with chromogenic products meet the following criteria: (1) the difference absorbance peak maximum wavelength of chromogenic product A is X1 and nearest to the infrared end, the difference absorbance peak maximum wavelength of chromogenic product C is X3 and nearest to the UV end, the difference absorbance peak maximum wavelength of chromogenic product B is X2 and locates between X1 and X3, the distances between or among X2 and X1 and X3 are all greater than 30 nm and preferably as far as possible; (2) the maximum isoabsorbance wavelength of chromogenic product A is Y1 and the second maximum isoabsorbance wavelength is Ys; the maximum isoabsorbance wavelength at which chromogenic substrate B generates chromogenic product B is Y2, and preferably as far as possible away from Y1, but as near as possible to Ys; (3) the distance between Y1 and X2 is less than 25 nm, and preferably as shorter as possible; the distances between/among Y2 and Ys and X3 are all less than 25 nm and preferably as short as possible;

In the examples for the practice of the present invention for simultaneously measuring the activities of three kinds of enzymes, in step b, simultaneously initiating the reactions of three kinds of enzymes with chromogenic substrate A, chromogenic substrate B and chromogenic substrate C in a single channel, to obtain the corresponding chromogenic product A, chromogenic product B and chromogenic product C;

In the examples for the practice of the present invention for simultaneously measuring the activities of three kinds of enzymes, in step c, taking the wavelength at the difference absorbance peak maximum wavelength X1 of chromogenic product A or within a distance less than 25 nm to it as $\lambda 1$ to determine the absorbance of chromogenic product A, selecting a wavelength equal to or within a distance less than 25 nm to the maximum isoabsorbance wavelength Y1 of chromogenic product A as $\lambda 2$ to determine the absorbance of chromogenic product B, selecting a wavelength equal to or within a distance less than 25 nm to the maximum isoabsorbance wavelength Y2 of chromogenic product B as $\lambda 3$ to determine the absorbance of chromogenic product C;

In the examples for the practice of the present invention for simultaneously measuring the activities of three kinds of enzymes, in step d, swift alteration of wavelengths realizes the simultaneous measurement of three wavelength absorbances to monitor the reaction processes of the three kinds of enzymes to be measured in a single reaction system or channel;

In the examples for the practice of the present invention for simultaneously measuring the activities of three kinds of enzymes, in step e, the calculation of the interference-free absorbance of chromogenic products or substrates is required to solve the following three-element linear equations in a group based on the linear additivity property of absorbances to eliminate the overlapping absorbance of multiple compounds:

$$A_1 = A_{10} + A_{1a} + R33 \times A_{2b} + R35 \times A_{3c}$$

$$A_2 = A_{20} + A_{2b} + R31 \times A_{1a} + R36 \times A_{3c}$$

$$A_3 = A_{30} + A_{3c} \pm R32 \times A_{1a} + R34 \times A_{2b}$$

wherein, $R31 = E32/E31$ $R32 = E33/E31$ $R33 = E34/E35$ $R34 = E36/E35$ $R35 = E37/E39$ $R36 = E38/E39$ In the above formula, $A_1$ is the instantaneous absorbance at $\lambda 1$ before correcting absorbance interference, $A_2$ is the instantaneous absorbance at $\lambda 2$ before correcting absorbance interference $A_3$ is the instantaneous absorbance at $\lambda 3$ before correcting absorbance interference, $A_{1a}$ is the net instantaneous absorbance of chromogenic product A at $\lambda 1$ after correcting absorbance interference, $A_{2b}$ is the net instantaneous absorbance of chromogenic product B at $\lambda 2$ after correcting absorbance interference, $A_{3c}$ is the net instantaneous absorbance of chromogenic product C at $\lambda 3$ after correcting absorbance interference; $A_{10}$ is the absorbance of reaction system at $\lambda 1$ before generating any chromogenic products, $A_{20}$ is the absorbance of reaction system at $\lambda 2$ before generating any chromogenic products, $A_{30}$ is the absorbance of reaction system at $\lambda 3$ before generating any chromogenic products; E31 is the difference molar extinction coefficient of chromogenic product A versus chromogenic substrate A at $\lambda 1$, E32 is the difference molar extinction coefficient of chromogenic product A versus chromogenic substrate A at $\lambda 2$, E33 is the difference molar extinction coefficient of chromogenic product A versus chromogenic substrate A at $\lambda 3$; E34 is the difference molar extinction coefficient of chromogenic product B versus chromogenic substrate B at $\lambda 1$, E35 is the difference molar extinction coefficient of chromogenic product B versus chromogenic substrate B at $\lambda 2$, E36 is the difference molar extinction coefficient of chromogenic product B versus chromogenic substrate B at $\lambda 3$; E37 is the differential molar extinction coefficient of chromogenic product C versus chromogenic substrate C at the measuring wavelength $\lambda 1$, E38 is the difference molar extinction coefficient of chromogenic product C versus chromogenic substrate C at the measuring wavelength $\lambda 2$, E39 is the difference molar extinction coefficient of chromogenic product C versus chromogenic substrate C at the measuring wavelength $\lambda 3$; in the above formula, the stoichiometric relationship of converting chromogenic substrate A into chromogenic product A is 1:1; the stoichiometric relationship of converting chromogenic substrate B into chromogenic product B is 1:1; the stoichiometric relationship of converting chromogenic substrate C into chromogenic product C is 1:1;

In the examples for the practice of the present invention for simultaneously measuring the activities of three kinds of enzymes, in step e, it is required to determine R31 and R32 as correcting coefficients of the absorbance disturbing of chromogenic product A; when determining, only all chromogenic substrates of enzyme A is used without using any chromogenic substrates for other enzymes to be measured, make the reaction system has no absorbance at the measuring wavelengths $\lambda 1$, $\lambda 2$ and $\lambda 3$ brought about by chromogenic substrate B, chromogenic product B, chromogenic substrate C or chromogenic product C, simultaneously measuring the absorbance changing in the reaction channel at the three measuring wavelengths, till both the absorbance changings at $\lambda 2$ and $\lambda 3$ are greater than 0.005 or the absorbance changing at $\lambda 1$ is greater than 0.500; take the absorbance at $\lambda 1$ as x-coordinate, the absorbance at $\lambda 2$ and $\lambda 3$ as y-coordinate to do regression analysis, the slope of the obtained regression line of the absorbance changing at $\lambda 2$ is correcting coefficient R31, the slope of the obtained regression line of the absorbance changing at $\lambda 3$ is correcting coefficient R32;

In the examples for the practice of the present invention for simultaneously measuring the activities of three kinds of enzymes, in step e, it is required to determine R33 and R34 as correcting coefficients of the absorbance disturbing of chromogenic product B; when determining, only all chromogenic substrates of enzyme B is used without using any chromogenic substrates for other enzymes to be measured, make the reaction system has no absorbance at the measuring wavelengths λ1, λ2 and λ3 brought about by chromogenic substrate A, chromogenic product A, chromogenic substrate C or chromogenic product C, simultaneously measuring the absorbance changing in the reaction channel at the three measuring wavelengths, till both the absorbance changings at λ2 and λ3 are greater than 0.005 or the absorbance changing at λ1 is greater than 0.500; take the absorbance at λ2 as x-coordinate, the absorbance at λ1 and λ3 as y-coordinate to do regression analysis, the slope of the obtained regression line of the absorbance changing at λ1 is correcting coefficient R33, the slope of the obtained regression line of the absorbance changing at λ3 is correcting coefficient R34;

In the examples for the practice of the present invention for simultaneously measuring the activities of three kinds of enzymes, in step e, it is required to determine R35 and R36 as correcting coefficients of the absorbance disturbing of chromogenic product C; when determining, only all chromogenic substrates of enzyme C is used without using any chromogenic substrates for other enzymes to be measured, make the reaction system has no absorbance at the measuring wavelengths λ1, λ2 and λ3 brought about by chromogenic substrate A, chromogenic product A, chromogenic substrate B or chromogenic product B, simultaneously measuring the absorbance changing in the reaction channel at the three measuring wavelengths, till both the absorbance changings at λ2 and λ1 are greater than 0.005 or the absorbance changing at λ3 is greater than 0.500; take the absorbance at λ3 as x-coordinate, the absorbance at λ1 and λ2 as y-coordinate to do regression analysis, the slope of the obtained regression line of the absorbance changing at λ1 is correcting coefficient R35, the slope of the obtained regression line of the absorbance changing at λ2 is correcting coefficient R36;

In the examples for the practice of the present invention for simultaneously measuring the activities of three kinds of enzymes, in step a, the combination of chromogenic substrates is selected according to the following principle: the used chromogenic substrate A, chromogenic substrate B and chromogenic substrate C make the maximum isoabsorbance wavelength Y1 of chromogenic product A equal to or is less than 5 nm away from the difference absorbance peak maximum wavelength X2 of chromogenic product B, the maximum isoabsorbance wavelength Y2 of chromogenic product B and the second maximum isoabsorbance wavelength Ys of chromogenic products A and the difference absorbance peak maximum wavelength X3 of chromogenic product C equal to each other or the distances between or among them are not greater than 5 nm;

In the examples for the practice of the present invention for simultaneously measuring the activities of three kinds of enzymes, in step c, after selecting the difference absorbance peak maximum wavelength X1 of chromogenic product A as λ1, the other two measuring wavelength λ2 and λ3 are selected according to the following principles: when the difference of the molar extinction coefficients of chromogenic product B versus chromogenic substrate B at the maximum isoabsorbance wavelength Y1 of chromogenic product A is higher than 30% of the difference of the molar extinction coefficients of the chromogenic product B versus chromogenic substrate B at the difference absorbance peak maximum wavelength X2, select Y1 as the measuring wavelength λ2, otherwise, selecting the difference absorbance peak wavelength of chromogenic product B nearest to the maximum isoabsorbance wavelength Y1 of chromogenic product A as λ2, or a wavelength that is near to the difference absorbance peak wavelength of chromogenic product B and gives the differences of the molar extinction coefficients of all the other chromogenic products versus their corresponding chromogenic substrates less than 20% of the difference of the molar extinction coefficients of chromogenic product B versus chromogenic substrate B as λ2, to measure the absorbance of chromogenic product B; if the difference of the molar extinction coefficients of chromogenic product C versus chromogenic substrate C at the second maximum isoabsorbance wavelength Ys of chromogenic product A or at the maximum isoabsorbance wavelength Y2 of chromogenic product B and chromogenic substrate B is higher than 30% of the difference of the molar extinction coefficients of chromogenic product C versus chromogenic substrate C at their difference absorbance peak maximum wavelength X3, select Y2 or Ys as λ3 to measure the absorbance of chromogenic product C, otherwise, selecting a wavelength that is nearest to the maximum isoabsorbance wavelength Y2 of chromogenic product B or the second maximum isoabsorbance wavelength Ys of chromogenic product A as λ3, or a wavelength that is near to the difference absorbance peak maximum wavelength of chromogenic product C and gives the differences of the molar extinction coefficients of all of the other chromogenic products versus their corresponding chromogenic substrates less than 20% of the difference of the molar extinction coefficients of chromogenic product C versus chromogenic substrate C as λ3, to measure the absorbance of chromogenic product C;

For the practice of the present invention for simultaneously measuring the activities of three kinds of enzymes, chromogenic substrate A corresponding to enzyme A comprises 4-nitro-1-naphthylphosphate which upon hydrolysis has two isoabsorbance wavelengths that locate at 315 to 335 nm and 395 to 415 nm, respectively, 4-nitro-1-naphthylsulphate which upon hydrolysis has two isoabsorbance wavelengths that locate at 315 to 335 nm and 395 to 415 nm, 4-nitro-1-naphthylacetate which upon hydrolysis has two isoabsorbance wavelengths that locate at 310 to 330 nm and 375 to 395 nm, 4-nitro-1-naphthyl-β-D-galactoside which upon hydrolysis has two isoabsorbance wavelengths that locate at 320 to 345 nm and 390 to 410 nm, 4-nitro-1-(N-lysyl) naphthylamide which upon hydrolysis has the maximum isoabsorbance wavelength at 385 to 410 nm, this chromogenic substrate A generates, under the action of enzyme A, 4-nitro-1-naphthol or 4-nitro-1-naphthylamine or derivatives thereof as chromogenic product A; chromogenic substrates B corresponding to this chromogenic substrate A is mainly 4-nitrophenol or 4-nitroaniline derivatives, which generates, under the action of the corresponding enzyme B, chromogenic product B which are 4-nitrophenol or 4-nitroaniline or 4-nitrophenylthiol; chromogenic substrate C corresponding to this chromogenic substrate A and chromogenic substrate B comprises nicotinamide adenine dinucleotide and nicotinamide adenine dinucleotide phosphate;

For the practice of the present invention for simultaneously measuring the activities of three kinds of enzymes, enzyme A corresponding to chromogenic substrate A comprises, but is not limited to, arylesterase, phosphatase, sulphatase, γ-glutamyltransferase, amidase and glycosidase corresponding to peptidase acting on amides of α-carboxyl group of natural amino acid; enzyme B corresponding to chromogenic substrate B comprises the other hydrolase other than the selected enzyme A but still belonging to hydrolytic enzymes; enzyme C corresponding to chromogenic substrate C comprises, but is not limited to, lactate dehydrogenase LDH, malate dehydrogenase MDH, LDH coupling alanine aminotransferase and MDH coupling aspartate aminotransferase.

The following sections are the detailed experimental data and the examples of practice.

In the examples for the practice of the present invention, chromogenic substrates are prepared via conventional organic syntheses, purified through silica gel chromatography, and confirmed through High-resolution-mass-spectrophotometry and NMR; the methods for the syntheses of such new chromogenic substrates are not the intellectual property of this invention. Common chromogens suitable for the present invention are illustrated in FIG. 2; the isoabsorbance wavelengths of common enzyme reactions are illustrated in FIGS. 3 and 4; the workflow for the use of two enzyme labels for ELISA is illustrated in FIG. 5.

In the examples for the practice of the present invention, absorbance spectra during enzyme reactions are recorded with Shimadzu UV2550 spectrophotometer without calibration of wavelengths. For the assays of enzyme activities, MAPADA UV1600 PC controlled by dedicated software is used, or Biotek ELX 800 microplate reader under the control of the software Gene5.0 is used. Unless otherwise stated, all assays are taken at room temperature or 25° C.

EXAMPLES

Example One: Two Wavelength Absorbance in Single Channel for Simultaneously Measuring LDH and GGT in the Homogenates of Rabbit Kidney In this example, the chromogenic substrates for the assay of lactic acid dehydrogenase (LDH, Shanghai Shangon, NB0642) are pyruvate and reduced form of nicotine adenine nucleotide (NADH), both are domestic reagents of analytical grade; chromogenic substrate for the assay of γ-glutamyltransferase (GGT) is γ-glutamyl-(4-nitro)-aniline (Sigma, 49525), glycylglycine is a domestic reagent of analytical grade; the reaction buffer used is 0.10 mol/sodium phosphate at pH 7.0; the chromogenic substrate of GGT is dissolved in the reaction buffer to yield chromogenic substrate solution A, the chromogenic substrates of LDH are dissolved in the reaction buffer to yield chromogenic substrate solution B; the chromogenic substrate solution containing the mixture of the chromogenic substrates of LDH and GGT is chromogenic substrate solution C; the chromogenic substrate of GGT γ-glutamyl-(4-nitro)-aniline is chromogenic substrate A, the corresponding chromogenic product A is 4-nitroaniline; NADH is the substrate of LDH but is taken as chromogenic product B; the absorbance of reaction solution containing only chromogenic substrate of GGT is used to adjust zero absorbance of the spectrophotometer; GGT is originated from rabbit kidney, prepared via homogenization of the tissues with 0.1% surfactant NP40 in the reaction buffer of 0.10 mol/L sodium phosphate at pH 7.0, and centrifuged at 4° C. and 10000 rpm for 20 min to get the supernatant as the sample rich in GGT, the homogenate prepared without the surfactant contains much lower activity of GGT.

The method for separate assay of GGT activity is described in China patent ZL 200710093081.4 and *J Zhejiang Univ Sci B,* 2011, 12(3):180-188; for data processing, the inhibition constants of the trans-glutamyl products on GGT is preset at 185 μmol/L, Michaelis constant of GGT for γ-glutamyl-(4-nitro)-aniline is preset at 1.00 mmol/L, the software for analyses is that described in *J Zhejiang Univ Sci B,* 2011, 12(3):180-188. In this example, GGT is enzyme A while LDH is enzyme B; chromogenic product A is 4-nitroaniline, chromogenic product B is NADH that is actually substrate B; among the measuring wavelengths, λ1 is 405 nm while λ2 is 344 nm (FIG. 3b).

The representative steps for the practice of the present invention for simultaneously measuring rabbit kidney GGT and rabbit muscle LDH are as follows.

1. preparing buffer: referring to Handbook of Common Data in Biochemistry and Molecular Biology Laboratories (The science publication press, 2000), and making 0.20 mol/L sodium phosphate buffer at pH 7.0 and then diluting into final 0.10 mol/L and pre-incubating at 25° C.;

2. preparing solutions of chromogenic substrates: a total of three solutions of chromogenic substrates are made; the stock solution of chromogenic substrate A contains final 1.5 mmol/L γ-glutamyl-4-nitro-aniline plus 0.70 mmol/L glycylglycine; the stock solution of chromogenic substrate B contains final 1.50 mmol/L NADH and 30.0 mmol/L pyruvate, the stock solution of chromogenic substrate C is the mixture of the stock solution of chromogenic substrate A and that of chromogenic substrate B at equal volume ratio; the total volume of reaction system is 1.0 ml, containing final concentrations of γ-glutamyl-4-nitro-aniline at 0.15 mmol/L and glycylglycine at 70 mmol/L, NADH at 0.15 mmol/and pyruvate at 3.0 mmol/L, and the reaction buffer;

3. preparing samples: homogenizing rabbit kidney in 0.10 mol/L sodium phosphate plus 0.1% NP40 at pH 7.0 in ice-water bath, followed by centrifugation at 4° C., 10000 rmp for 20 min to yield the supernatant as the sample rich in GGT, and the sample is diluted with the reaction buffer; the mixture of LDH and this sample of GGT gives the sample of two enzymes;

4. estimating the correction coefficient for concomitantly monitoring multiple wavelength absorbances: using the stock solution of chromogenic substrate A plus a proper volume of buffer and sample for final glycylglycine at 70 mmol/L and chromogenic substrate A at 0.15 mmol/L, to determine the relationship between the absorbance at λ1 and that ast λ2 (FIG. 6a) in 10.0 min for the increase of absorbance at 405 nm over 0.55; utilizing the stock solution of chromogenic substrate B plus a proper volume of buffer and the sample of LDH alone, to determine the association of the changes of absorbance at λ1 and those at λ2 (FIG. b) in 10.0 min for the decrease of absorbance at 344 nm more than 0.55; In FIGS. 7a and 7b, the response sploes of statistic significance are the interference correction coefficients R31 and R33;

5. simultaneously measuring LDH and GGT in single channel: the stock solution of chromogenic substrate C plus proper volumes of the reaction buffer and the sample to make up 1.0 ml in total for γ-glutamyl-4-nitro-aniline at 0.15 mmol/L and glycylglycine at 70 mmol/L, NADH at 0.15 mmol/L and pyruvate at 3.0 mmol/L; after making solution by vortex mixing to synchronously initiate the reactions of two enzymes, concomitantly monitoring two wavelength absorbances at λ1 and λ2 in 15.0 min to facilitate kinetic analysis of reaction process; NADH has no absorbance at 405 nm, and the absorbance at 405 nm contains the absorbance of the background, chromogenic product 4-nitroaniline, and thus no correction of the absorbance of NADH at 405 nm is required; at different volumes of the sample, the background is determined as the sum of the absorbance of the sample and chromogenic substrate A and the absorbance at 405 nm after the correction of the background is the net absorbance of 4-nitroaniline for the correction of its interfering action on LDH action; the recording intervals are 20 s in a total of 15 min; data for the changes of two wavelength absorbances are processed as described in detail below:

(1) obtaining the interference-free absorbance change curves at two selected wavelengths $A_{10}$ at λ1 and $A_{20}$ at λ2 are determined independently with reaction systems minus the sample; before the correction of the interference of the overlapped absorbencies, the instantaneous absorbance at λ1 is assigned to $A_1$, the instantaneous absorbance at λ2 is assigned to $A_2$; after the correction of the interference of the overlapped absorbencies, the instantaneous absorbance of 4-nitroaniline at λ1 is assigned to $A_{1a}$, the instantaneous absorbance of chromogenic product, NADH, at λ2 is assigned to $A_{2b}$, there are the following equations based on the linear additivity of absorbances of compounds bearing negligible interactions:

$$A_1 = A_{10} + A_{1a} + R33 \times A_{2b}$$

$$A_2 = A_{20} + A_{2b} + R31 \times A_{1a}$$

The solutions to the two-element linear equations give the interference-free absorbance data of two chromogenic products at two selected wavelengths, and the instantaneous concentrations of chromogenic product A and chromogenic product B in reaction channel can be obtained with the difference molar absorption coefficients of chromogenic product A versus chromogenic substrate A at λ1, and chromogenic product B versus chromogenic substrate B at λ2; the processing of the interference-free absorbance data or instantaneous concentrations of two chromogenic products at two selected wavelengths realizes simultaneous measurement of the activities of two enzymes in single channel;

(1) Estimating the Activity of GGT Via Kinetic Analysis of Reaction Curve

Using the method described in china patent ZL 200710093081.4 and *J Zhejiang Univ Sci B,* 2011, 12(3): 180-188 for the integration of kinetic analysis of reaction process with the classical initial rate method for the estimation of initial rate of GGT (this is not the intellectual property claimed in the present invention, but rather, the application of china patent ZL 200710093081.4); for data processing, the inhibition constant of the trans-glutamyl product on GGT is preset at 185 λmol/L, the Michaelis constant of GGT for γ-glutamyl-4-nitro-aniline is present at 1.00 mmol/L, the software is the same as in *J Zhejiang Univ Sci B,* 2011, 12(3):180-188; the preset substrate concentration for the conversion of the maximal reaction rate into initial rate is 0.14 mmol/L; the integration strategy yields a wider linear range for GGT activities, as in FIG. 6c;

(2) Eliminating the Interference of 4-Nitroaniline on LDH Action

The interference-free absorbance at 405 nm after the correction of the contribution of the background, $A_{1a}$ is converted into the concentration of 4-nitroaniline with the molar absorption coefficient of 9.87 L·(mmol·cm)$^{-1}$; the competitive inhibition constant of 4-nitroaniline on LDH is 0.024 mmol/L, the Michaelis constant of LDH for NADH is 0.040 mmol/L; the difference molar absorption coefficient of 4-nitroaniline versus γ-glutamyl-4-nitro-aniline at 405 nm is 9.87 L·(mmol·cm)$^{-1}$, the difference molar absorption coefficient of NADH versus NAD at 344 nm is 6.25 L·(mmol·cm)$^{-1}$, the final concentration of pyruvate is nearly 20 times higher than that of the initial concentration of NADH and the action of LDH on NADH is assumed to follow the kinetics for single chromogenic substrate; the preset concentration of NADH from the conversion of the maximal reaction rate into initial rate is 0.14 mmol/L; the maximal reaction rate of LDH is assigned to VmB; after the correction of the overlapped absorbance of γ-glutamyl-4-nitro-aniline and 4-nitroaniline, the instantaneous absorbance of NADH at 344 nm is assigned to $A_{2b}$, kinetic analyses of the correlated reaction processes of GGT and LDH are performed as follows to estimate $V_{mB}$ of LDH:

$$\int_0^\tau dA_{2b} = 6.25 \times 0.14 \times V_{mB} \times \frac{1}{3} \times \int_0^\tau \frac{1}{0.040 \times (1 + A_{ia}/0.024/9.87) + 0.14}$$

$$x = \frac{1}{0.040 \times (1 + A_{ia}/0.024/9.87) + 0.14}$$

$$\text{sum} x = \int_0^\tau \frac{1}{0.040 \times (1 + A_{ia}/0.024/9.87) + 0.14}$$

$$V_{mB} = \left( \int_0^\tau dA_{2b} \right) / \left[ \left( 6.25 \times 0.14 \times \frac{1}{3} \right) \times \text{sum} x \right]$$

Assuming there is a constant concentration of 4-nitroaniline within the intervals for recording two wavelength absorbance, numerical integration yields its integral as Sumx; there can be $V_{mB}$ of LDH for conversion into initial rate with initial level of NADH at 0.14 mmol/L; the response plot is shown in FIG. 6d; the effects of the correction of the interference of 4-nitroaniline are shown in Table 2; this correction yields a limit of quantification by simultaneously measuring two enzymes comparable to those by separate assays.

6. In the absence of the action of LDH, the limit of quantification of GGT is 0.11 μmol·(L·min)$^{-1}$; when the activity of LDH determined with the solution of chromogenic substrate B is 8.2 μmol·(L·min)$^{-1}$, the limit of quantification of GGT is 0.14 μmol·(L·min)$^{-1}$ by simultaneously measuring two enzymes; when the activity of LDH is 20 μmol·(L·min)$^{-1}$, the limit of quantification of GGT is 0.17 μmol·(L·min)$^{-1}$ (Table 1). In the absence of GGT, the limit of quantification of LDH is 0.7 μmol·(L·min)$^{-1}$; when the activity of GGT is 1.7 μmol·(L·min)$^{-1}$ as determined with chromogenic substrate solution A, the limit of quantification of LDH is 0.6 μmol·(L·min)$^{-1}$, when the activity of GGT is 10.7 μmol·(L·min)$^{-1}$ as LDH determined with chromogenic substrate solution A, the limit of quantification of LDH is 0.5 μmol·(L·min)$^{-1}$; results are shown in Table 3.

Example Two: Multiple Wavelength Absorbances in Single Channel for Simultaneously Measuring Alkaline Phosphatase and Natural β-D-galactosidase In the example, calf intestinal alkaline phosphatase (Sigma P0114, CIAP) is enzyme A, β-D-galactosidase (β-Gal) in lysates of *Escherichia coli* BL21(DE3) cells is passed through Sephadex G25 column to remove small biochemicals to serve as Enzyme B (the column of Sephadex G25 has a column height of 15 cm and an inner diameter of 10 mm in a total of 10 ml, and is equilibrated and washed with 50 mmol/L Tris-HCl buffer at pH 7.5). 4-nitro-1-naphthylphosphate is chromogenic substrate A and synthesized following a procedure that has been reported early (MM Mhala, Puma Nand. Hydrolysis of organic phosphatases. Part IX—hydrolysis of 1-nitro-2-naphthyl- and 4-nitro-1-naphthyl-phosphate moniesters [J]. Indian Journal of Chemistry, 1976, Vol 14A: 344-346) and purified through silica gel column (the column is eluted with 10% chloroform in methanol, and thin-layer-chromatography detects no other components; the quantity of chromogenic substrate A is determined from the quantity of 4-nitronaphthol released upon complete hydrolysis under the action of CIAP by absorbance at 460 nm with authentic 4-nitro-1-naphthol from Alfa-Aesar (no. L19782) as the reference; the preparation of 4-nitro-1-naphthylphosphate has a content of 68%, plus less than 2% free 4-nitro-1-naphthol; there is about 27% sodium chloride based on the quantity of sodium ion), 4-nitrophenyl-β-D-galactoside is from BBI (no. NB2361-1g). Chromogenic product A is 4-nitronaphthol, chromogenic product B is 4-nitrophenol; measuring wavelength $\lambda 1$ is 450 nm (microplate reader), and $\lambda 2$ is 405 nm (FIGS. 4b and 3a).

The microplate reader is Biotek EIX800 under the control by Gene 5.0 software. The buffer pH is 7.5 and contains 5.0 μmol/L citrate in 50 mmol/L Tris-HCl; chromogenic substrate is dissolved in this buffer to yield chromogenic substrate solution A, chromogenic substrate B is dissolved in this buffer to yield chromogenic substrate solution B; the mixture of chromogenic substrates of enzyme A and enzyme B is chromogenic substrate solution C.

For the application of the present invention for simultaneously measuring CIAP and β-Gal, the representative process is as follows:

1. preparing buffer: according to Biochemical Methods and Technology (Higher-Education Press, 1981; $1^{st}$ ed; p 374), preparing 50 mmol/L Tris-HCl buffer at pH 7.5 plus 5 umol/L citrate; the buffer is incubated in 25° C. water bath prior to use;

2. preparing chromogenic substrate solutions: chromogenic substrate solution A contains only final 0.20 mmol/L 4-nitro-1-naphthylphosphate, the stock solution of chromogenic substrate A is prepared with dimethylsulfoxide at 20 mmol/L and diluted with the Tris-HCl buffer to 0.20 mmol/L just prior to use; chromogenic substrate solution B contains 6.0 mmol/L 4-nitrophenyl-β-D-galactoside directly dissolved in Tris-HCl buffer and used one day; chromogenic substrate solution C contains 0.20 mmol/L 4-nitro-1-naphthylphosphate, 6.0 mmol/L 4-nitrophenyl-β-D-galactoside, following that for the preparation of chromogenic substrate solution A and chromogenic substrate solution B, and used in one day;

3. preparing sample: diluting the stock solution of CIAP according to the statement of the provider with the Tris-HCl buffer to about 800 U/L, diluting β-Gal with the Tris-HCl to about 600 U/L; the equal volume mixture of two enzyme solutions yields a mixture sample of two enzymes;

4. Estimating the correction coefficients for concomitantly monitoring multiple wavelength absorbances: using the indicated concentration of 4-nitro-1-naphthylphosphate, continuously and concomitantly monitoring absorbance changes at 450 and 405 nm during the action of CIAP, and there is a linear increase in absorbance at 450 nm till the absorbance of 0.60, analysis of the response of absorbance at 405 nm to those at 450 nm gives a slope as the correction coefficient R31 (FIG. 7a); using the indicated concentration of 4-nitrophenyl-β-D-galactoside, continuously and concomitantly monitoring absorbance changes at 450 and 405 nm during the action of β-Gal, there is a linear increase in absorbance at 405 nm till the absorbance of 1.00, analysis of the response of absorbance at 450 nm to those at 405 nm gives a slope as the correction coefficient R33 (FIG. 7b);

5. Simultaneously measuring CIAP and β-galactosidase: using chromogenic substrate solution C and diluting to the required final levels of two chromogenic substrates to adjust zero absorbance concomitantly at 405 nm 450 nm, withdrawing a total of 1.50 ml chromogenic substrate solution C plus proper volumes of the sample and the buffer to make up 2.0 ml, after mixing via vortex, at 25° C. to concomitantly monitor absorbance changes at 405 nm and 450 nm, at intervals of 20 s in a total of 3.0 min; two wavelength absorbances change linearly in 90 s and the responses of initial rates to quantities of enzymes are calculated simply as follows (FIG. 7c and FIG. 7d);

6. solving the following equations to get the interference-free absorbance change initial rates s1 at 450 nm and s2 at 405 nm (FIG. 7c and FIG. 7d); results show that the response slopes by simultaneously measuring the activities of two enzymes have no significant differences from those by separate assays;

$$V1=s1+R33\times s2$$

$$V2=s2+R31\times s1$$

7. In the absence of β-D-galactosidease, the limit of quantification of CIAP for simultaneously measuring the activities of two enzymes is about 0.06 $\mu mol \cdot (L \cdot min)^{-1}$; when β-D-galactosidase activity is 0.6 $\mu mol \cdot (L \cdot min)^{-1}$, the limit of quantification of CIAP for simultaneously measuring the activities of two enzymes is about 0.06 $\mu mol \cdot (L \cdot min)^{-1}$; when β-D-galactosidase activity is 2.5 $\mu mol \cdot (L \cdot min)^{-1}$, the limit of quantification of CIAP for simultaneously measuring the activities of two enzymes is about 0.08 $\mu mol \cdot (L \cdot min)^{-1}$; in the absence of CIAP, the limit of quantification of β-D-galactosidase is about 0.07 $\mu mol \cdot (L \cdot min)^{-1}$; when CIAP activity is 0.7 $\mu mol \cdot (L \cdot min)^{-1}$ determined with chromogenic substrate solution A, the limit of quantification of β-D-galactosidase for simultaneously measuring the activities of two enzymes is about 0.09 $\mu mol \cdot (L \cdot min)^{-1}$; when CIAP activity is 5.6 $\mu mol \cdot (L \cdot min)^{-1}$, the limit of quantification of β-D-galactosidase for simultaneously measuring the activities of two enzymes is 0.08 $\mu mol \cdot (L \cdot min)^{-1}$. Results are given in Table 4.

Example Three: Simultaneously Measuring Penicillin G and Clenbuterol in Milk Via Enzyme-Linked-Adsorbent-Immunoassay (ELISA)

The present example of practice utilizes β-D-galactosidase (Sigma G4155, β-Gal) as enzyme A and α-D-glucosidase (Sigma G0660, α-Glu) as enzyme B; 4-nitro-1-naphthyl-β-D-galactoside as chromogenic substrate A and synthesized by the procedure of 4-nitrophenyl-β-D-galactoside, and purified via silica gel chromatography (the purity of 4-nitro-1-naphthyl-β-D-galactoside is quantified by the quantity of 4-nitro-1-naphthol released upon complete hydrolysis by β-Gal); 4-nitrophenyl-α-D-glucosidase as chromogenic substrate B; the buffer is 100 mmol/L sodium phosphate at pH 7.4. Chromogenic product A is thus 4-nitro-1-naphthol and chromogenic product B is 4-nitrophenol; measuring wavelength $\lambda 1$ is 450 nm and measuring wavelength $\lambda 2$ is 405 nm (the standard filters equipped on Biotek ELX 800 microplate reader, FIG. 4a). The mixture of enzyme samples in the present example of practice is enzyme A and enzyme B adsorbed on microplate wells after separation through the process of ELSIA.

The microplate pre-coated with goat anti-mouse IgG (Pierce 15134, 7 pmole binding capacity each well) is used in the present example of practice; mouse anti-penicillin G monoclonal antibody is Abcam ab15070, mouse anti-clenbuterol monoclonal antibody is Abcam ab32005; β-Gal is modified with penicillin G while α-Glu is n modified with clenbuterol; the modified enzyme is passed through Sephadex G25 column to remove free hapten. The representative process for simultaneously measuring penicillin G and clenbuterol of milk in single channel by the present invention is described as follows:

1. preparing buffer: according to Handbook of Common Data in Biochemistry and Molecular Biology Laboratories (The science publication press, 2000), preparing 100 mmol/L sodium phosphate at pH 7.4; the buffer is pre-incubated at 25° C. prior to use;

2. preparing chromogenic substrate solution A, chromogenic substrate solution B and chromogenic substrate solution C: chromogenic substrate A is dissolved in dimethylsulfoxide at 20 mmol/L as the stock solution of chromogenic substrate A, which is diluted with the sodium phosphate buffer at pH 7.4 to final 0.20 mmol/L to serve as chromogenic substrate solution A; chromogenic substrate B is dissolved in a mixture of 20% dimethylsulfoxide in the sodium phosphate buffer to 50 mmol/L as the stock solution of chromogenic substrate B, and is diluted with the sodium phosphate buffer to final 2.6 mmol/L to serve as chromogenic substrate solution B; the mixture of the stock solution of chromogenic substrate A and the stock solution of chromogenic substrate B to final chromogenic substrate A of 0.20 mmol/L and chromogenic substrate B of 2.6 mmol/L gives chromogenic substrate solution C;

3. labeling β-D-galactosidase with penicillin G:

a) activating penicillin G: 0.73 g sodium penicillin G is dissolved in 2.0 ml dimethylformamide, to this solution 0.40 g 1-ethyl-(3-dimethylamino)-carbodiimide hydrochloride (EDC) and 0.30 g NHydroxybenzotrizole are added for reaction of 30 min at room temperature to yield a dark yellow solution; the dilution of 4 ul of the aforementioned dark yellow solution by 54 ul of the sodium phosphate buffer yields the activated penicillin G;

b) mixing 50 ul solution of the activated penicillin G with 0.50 ml of 0.44 mg β-D-galactosidase dissolved in the sodium phosphate buffer at pH 7.4, keeping the mixture at 4° C. for reaction for 120 min; the resulting mixture of the labeled β-D-galactosidase is passed through Sephadex G25 column (15 cm height and 10 mm inner diameter with a packed volume of 10 ml, equilibrated with 50 mmol/L Tris-HCl at pH 7.5) and the column is eluted with the same Tris-HCl buffer to monitor the absorbance at 280 nm; the first peak of the elution is the labeled β-D-galactosidase, with a total of 0.22 mg protein in 2.0 ml elution solution;

c) determining the specific activity after labeling: in 50 mmol/L Tris-HCl at pH 7.5, the specific activity of the labeled β-D-galactosidase is about 30 μmol·(L·min·mg)$^{-1}$ on 4-nitrophenyl-β-D-galactoside, indicating the reservation of nearly 100% activity; meanwhile, the specific activity on 4-nitro-1-napthyl-β-D-galactoside in the same buffer, its specific activity is about 100 (L·min·mg)$^{-1}$, but just about 70% of that before modification;

d) estimating the quantity of the labeled β-D-galactosidase for use in analysis: after the optimization of the quantity of the used monoclonal antibody against penicillin for the practice, the quantities of the labeled β-D-galactosidase in microplate wells are continuously increased till there are the saturation binding of the hapten-labeled β-D-galactosidase; with 96-wells, the use of 20 ul of the solution of the used monoclonal antibody against penicillin after dilution by 500 times, there is the saturation binding of the labeled β-D-galactosidase from 20 ul;

4. labeling of α-D-glucosidase with clenbuterol a) clenbuterol 0.80 g is dissolved in 1.0 ml hydrochloride solution at pH 1.0, to the solution 24 ul solution of 1.0 mol/L sodium nitrite is added for reaction at temperature for 30 min; the detection of the solution with iodine-starch paper gives blue and indicates the completion of the activation reaction, yielding the activated clenbuterol;

b) α-D-glucosidase is dissolved in 200 mmol/L sodium phosphate buffer at pH 7.8 (containing 10% glycerol) to final 2.0 g/L; to 100 ul solution of the α-D-glucosidase, 2.0 ul of the solution of the activated clenbuterol is added for reaction at 4° C. for 12 h; after modification reaction, the resulting mixture is passed through Sephadex G25 column (15 cm height and 10 mm inner diameter with a packed volume of 10 ml, equilibrated with 100 mmol/L sodium phosphate at pH 7.4) and the column is eluted with the same sodium phosphate buffer to monitor the absorbance at 280 nm; the first peak of the elution in 2.0 ml yields the solution of the labeled α-D-glucosidase;

c) determining the specific activity after labeling: in 100 mmol/L sodium phosphate buffer at pH 7.4, the specific activity of the labeled α-D-glucosidase is about 90 μmol·(L·min·mg)$^{-1}$ on 2.6 mmol/L 4-nitrophenyl-α-D-glucosidase, indicating the reservation of 100% activity;

d) the solution of the anti-clenbuterol monoclonal antibody is diluted by 5000 fold, the use of 80 ul solution of the diluted antibody and 10 ul solution of the labeled α-D-glucosidase achieves saturation binding;

5. optimizing the ratio of detection monoclonal antibodies ab15070 and ab32005: the solution of the monoclonal antibody against penicillin G is diluted by 1:500 and the solution of the monoclonal antibody against clenbuterol is diluted by 1:5000; the quantity of each monoclonal antibody varies from 20 to 80 ul for mixing and 40 ul solutions of the aforementioned solutions of the labeled β-D-galactosidase and the labeled α-D-glucosidase are used in each well; for the comparable absorbance change rates at 450 nm and 405 nm, there are the needs of 20 ul solution of the antibody against penicillin G and 80 ul solution of the antibody against clenbuterol; in the following sections, the two monoclonal antibodies are mixed at such a ratio and a total of 100 ul solution of the mixed antibodies is used in each well;

6. optimizing the ratio of the two hapten-labeled enzymes: 300 ul of the aforementioned solution of the clenbuterol-labeled α-D-glucosidase and 600 ul of the aforementioned penicillin-labeled β-D-galactosidase are mixed and diluted further with 100 mmol/L sodium phosphate buffer at pH 7.4 to a total of 3.0 ml; each time, 100 ul of the diluted mixture of two labeled enzymes is used; 7. operating as follows with Pierce 96-well microplate pre-coated with goat anti-mouse IgG polyclonal antibodies: (1) 100 ul of the mixture of the two monoclonal antibodies is added to each well for mild vibration at 25° C. for 60 min; (2) each well is repetitively washed for three times, each time with 0.20 ml of 100 mmol/L sodium phosphate buffer at pH 7.4 plus 0.05% Tween-20 for 3.0 min under mild vibration; (3) milk drink is centrifuged at 4° C. for 30 min at 8000 rpm to get the fat-free milk, which is further diluted with an equal volume of 100 mmol/L sodium phosphate buffer followed by the addition of penicillin and clenbuterol to serve as an artificial sample; (4) the diluted mixture of two labeled enzymes is mixed further with a sample at 2:3 ratio, 100 ul of which is applied to each well for competitive binding at room temperature for 30 min; the unbound components are discarded and each well is washed again repetitively for three times, each time with 0.20 ml of 100 mmol/L sodium phosphate buffer at pH 7.4 plus 0.05% Tween-20 for 3.0 min under mild vibration;

8. determining activities of the bound labeled enzymes: applying 200 ul of each of chromogenic substrate solution A, chromogenic substrate solution B, and chromogenic substrate solution C to every well, after mild vibration of microplate for 10 min, absorbances at 405 nm and 450 nm are monitored concomitantly at 3.0 min-interval, in a total of 30 min, with Biotek ELX 800 microplate reader under the control by Gene 5.0 software;

9. determining correcting coefficient: operations follow those described in Example two; using the same concentration of 4-nitro-1-naphthyl-β-D-galactoside as that in chromogenic substrate solution A, plus β-D-galactosidase, to concomitantly monitor absorbances at 405 nm and 450 nm at intervals of 20 s, in a total of 3.0 min, to yield a linear increase of absorbance at 450 nm till the absorbance of 0.80, regression analysis of the response of the absorbance at 405 nm to those at 450 nm gives the slope of linear response as R31 (FIG. 8a); applying the same concentration of 4-nitrophenyl-α-D-glucoside as that in chromogenic substrate solution B, plus α-D-glucosidase, to concomitantly monitor absorbances at 405 nm and 450 nm at intervals of 20 s, in a total of 3.0 min, to yield a linear increase of absorbance at 405 nm till the absorbance of 0.80, and regression analysis of the response of the absorbance at 450 nm to those at 405 nm gives the slope of linear response as R33 (FIG. 8b);

10. comparing simultaneous measurement of two glycosidases against separate assay: chromogenic substrate solution C is diluted for the final levels of two chromogenic substrates to measure enzyme activities, and used for adjusting zero absorbance of spectrophotometer; to 1.50 ml of chromogenic substrate solution C, a proper volume of enzyme sample plus the buffer in a total of 0.50 ml is added; the resulting mixture is make homogenous via vrotx and two wavelength absorbances at 405 nm and 450 nm are monitored concomitantly at 20 s intervals, in a total of 3.0 min; two wavelength absorbances increase linearly in 90 s and apparent initial rates are derived routinely to get the responses of activities to enzyme quantities (FIGS. 8c and 8d);

11. constructing the response plots: according to the correcting coefficients R31 and R33 as determined above, converting the apparent absorbance change rates V1 at 450 nm and V2 at 405 nm into interference-free absorbance change rates s1 and s2, respectively, followed by the correction of spontaneous hydrolysis of each chromogenic substrate; the binding ratio of each hapten-labeled enzyme is assigned to 100% in the absence of any additional hapten in the fat-free milk sample, for the calculation of the binding ratio of each hapten-labeled enzyme under the competitive binding of additional haptens as the references;

12. hapten-labeled enzyme binding ratio: constructing a response plot of binding ratios of each hapten-labeled enzyme to logarithmic concentrations of reference hapten; there are linear responses for binding ratios from 10% to 85% (FIGS. 8e and 8f);

13. data processing and result report: for two glycosidase-labeled simultaneous ELISAs of two haptens, the comparison of the limits of quantification is given in Table 5, the comparison of recovery ratios is given in Table 6.

TABLE 1

Materials and parameters for simultaneously measuring three enzymes through three wavelength absorbances
Spectral parameters and their quantitative relationships for simultaneously measuring the activities of three kinds of enzymes

| enzymes | A | B | C |
|---|---|---|---|
| Measuring wavelength | 1 | 2 | 3 |
| Apparent initial rate | $V_1$ | $V_2$ | $V_3$ |
| Authentical initial rate | $s_1$ | $s_2$ | $s_3$ |
| The relative contribution of enzyme A to each apparent initial rate | 1 | $R_{31}$ | $R_{32}$ |

TABLE 1-continued

Materials and parameters for simultaneously measuring three enzymes through three wavelength absorbances
Spectral parameters and their quantitative relationships for simultaneously measuring the activities of three kinds of enzymes

| enzymes | A | B | C |
|---|---|---|---|
| The relative contribution of enzyme B to each apparent initial rate | $R_{33}$ | 1 | $R_{34}$ |
| The relative contribution of enzyme C to each apparent initial rate | $R_{35}$ | $R_{36}$ | 1 |
| Enzyme A-related apparent initial rate | $V_1 = s_1 + s_2 \times R_{33} + s_3 \times R_{35}$ | | |
| Enzyme B-related apparent initial rate | $V_2 = s_2 + s_1 \times R_{31} + s_3 \times R_{36}$ | | |
| Enzyme C-related apparent initial rate | $V_3 = s_3 + s_1 \times R_{32} + s_2 \times R_{34}$ | | |

TABLE 2

Effects of the correction of the interference of p-nitroaniline (PNA) with LDH (n > 5)

| PNA absorbance | Before correction ΔA/min | After correction ΔA/min | Separate assay ΔA/min | Recovery ratio CV(%) | Averaged recovery ratio CV(%) |
|---|---|---|---|---|---|
| no | 0.006 | 0.007 | 0.005 | 137 | 140 ± 5 |
|  | 0.013 | 0.015 | 0.010 | 141 |  |
|  | 0.020 | 0.021 | 0.016 | 134 |  |
|  | 0.027 | 0.033 | 0.022 | 146 |  |
| yes | 0.006 | 0.005 | 0.005 | 95 |  |
|  | 0.013 | 0.010 | 0.010 | 97 |  |
|  | 0.02 | 0.015 | 0.016 | 97 |  |
|  | 0.027 | 0.024 | 0.022 | 105 |  |
| no | 0.003 | 0.005 | 0.004 | 119 | 112 ± 5 |
|  | 0.009 | 0.014 | 0.013 | 110 |  |
|  | 0.026 | 0.041 | 0.037 | 111 |  |
|  | 0.048 | 0.073 | 0.068 | 108 |  |
| yes | 0.003 | 0.004 | 0.004 | 102 | 98 ± 3 |
|  | 0.009 | 0.012 | 0.013 | 95 |  |
|  | 0.026 | 0.036 | 0.037 | 98 |  |
|  | 0.048 | 0.066 | 0.068 | 97 |  |

TABLE 3

The limits of quantification for simultaneously measuring the activities of GGT and LDH (n > 3)

| Enzyme quantity μmol · (L · min) − 1 | | LOQ μmol · (L · min) − 1 | |
|---|---|---|---|
| GGT | LDH | GGT | LDH |
| 0 | 0 | 0.11 | 0.7 |
| 1.2 | 0 | / | 0.6 |
| 10.7 | 0 | / | 0.5 |
| 0 | 2.2 | 0.14 | / |
| 0 | 20 | 0.17 | / |

TABLE 4

The limits of quantification for simultaneously measuring the activities of CIAP and β-Gal (n > 3)

| Enzyme quantites μmol · (L · min) − 1 | | LOQ μmol · (L · min) − 1 | |
|---|---|---|---|
| CIAP | β-Gal | CIAP | β-Gal |
| 0 | 0 | 0.06 | 0.07 |
| 0.7 | 0 | / | 0.09 |
| 5.6 | 0 | / | 0.08 |
| 0 | 0.6 | 0.06 | / |
| 0 | 2.5 | 0.08 | / |

TABLE 5

The limits of quantification (LOQ) of binding ratios and haptens by the use of β-Gal and α-Glu as label enzymes for simultaneously measuring clenbuterol and penicillin in single channel (n > 5)

| Binding ratio (%) (n = 5) | | mean x | Standard deviation SD | x-5*SD | LOQ ng/well |
|---|---|---|---|---|---|
| Simultaneous measurement | Penicillin G | 100.0 | 2.6 | 87.2 | 20.2 |
| | clenbuterol | 100.0 | 1.9 | 90.6 | 4.0 |
| Separate assay | Penicillin G | 100.0 | 1.3 | 93.6 | 16.0 |
| | clenbuterol | 100.0 | 4.1 | 79.3 | 3.0 |

TABLE 6 recovery ratios for simultaneously measuring clenbuterol and penicillin with β-Gal and α-Glu as labels in single channel (n > 5)

| | | Simultaneous measurement after correction | | | Separate assay | | |
|---|---|---|---|---|---|---|---|
| Penicillin ng/well | Clenbuterol ng/wel | Binding ratio (%) | penicillin ng/well | Recovery ratio CV(%) | Binding ratio (%) | penicillin ng/well | Recovery ratio CV(%) |
| 20 | 4 | 86 | 19 | 93 ± 18 | 86 | 19 | 94 ± 17 |
| 80 | 16 | 46 | 99 | 123 ± 1 | 50 | 87 | 109 ± 3 |
| 320 | 64 | 20 | 296 | 93 ± 4 | 20 | 299 | 94 ± 3 |
| 20 | 64 | 80 | 24 | 122 ± 8 | 80 | 25 | 123 ± 8 |
| 320 | 4 | 26 | 237 | 74 ± 3 | 21 | 290 | 91 ± 1 |
| Recovery ratio for penicillin assay | | / | / | 101 ± 21 | / | / | 102 ± 14 |

| | | Simultaneous measurement after correction | | | Separate assay | | |
|---|---|---|---|---|---|---|---|
| Penicillin ng/well | Clenbuterol ng/wel | Binding ratio (%) | Clenbuterol ng/wel | Recovery ratio CV(%) | Binding ratio (%) | Clenbuterol ng/wel | Recovery ratio CV(%) |
| 20 | 4 | 90 | 4 | 100 ± 6 | 90 | 4 | 98 ± 2 |
| 80 | 16 | 68 | 20 | 124 ± 1 | 66 | 18 | 111 ± 2 |
| 320 | 64 | 53 | 61 | 95 ± 1 | 47 | 64 | 99 ± 1 |
| 20 | 64 | 54 | 54 | 84 ± 6 | 51 | 49 | 76 ± 4 |
| 320 | 4 | 86 | 5 | 128 ± 1 | 89 | 4 | 105 ± 1 |
| Recovery ratio for ckenbuterol assay | | / | / | 106 ± 19 | / | / | 98 ± 13 |

All the aforementioned examples for practice are used to illustrate the technical principles, but not the limitations to such examples; technicians in the pertinent technical field should understand, there can be some modifications or substitution of the technical details of the present invention, which however still follow the same technical principles of the present invention and thus should be included in the claimed fields of the present invention; besides 4-nitro-1-naphthol, 4-nitrophenol, 4-nitroaniline, 4-nitro-1-naphthylamine as chromogens, other chromogens satisfying the requirement of spectral properties still can be used to prepare chromogenic substrates of special enzymes for simultaneously measuring the activities of multiple kinds of enzymes through concomitantly monitoring multiple wavelength absorbances, yielding the limits of quantification, sensitivity and linear ranges comparable to those by separate assay.

The invention claimed is:

1. A method for simultaneously measuring the activities of multiple kinds of enzymes in single channel through concomitantly monitoring multiple wavelength absorbances the method comprising:

a. determining the combination of chromogenic substrates required for simultaneously measuring the activities of multiple kinds of enzymes:

a1. selecting the combination of chromogenic substrates that meets the following criteria according to the specificity of the enzymes to be measured: the selected chromophores can be respectively used to prepare the chromogenic substrates of the enzymes to be measured; in the obtained combination of chromogenic substrates, the difference absorbance peak maximum wavelengths of the chromogenic products formed under the actions of the respective enzymes to be measured with respect to their chromogenic substrates are arranged from large to small to give a one-dimension array, the distance between any two adjacent difference absorbance peak maximum wavelengths of the chromogenic products in the aforementioned array is greater than 30 nm and preferably as far as possible; in the array of the difference absorbance peak maximum wavelengths of the chromogenic products from large to small, except for the chromogenic substrate whose chromogenic product has the difference absorbance peak maximum wavelength nearest to the infrared end, the difference absorbance peak maximum wavelength of each chromogenic product obtained from its chromogenic substrate under the action of the corresponding enzyme is less than 25 nm and preferably as shorter as possible away from the maximum isoabsorbance wavelength of one of the chromogenic substrates in the aforementioned array;

a2. synthesizing corresponding chromogenic substrates of the enzymes to be measured respectively by the chromophores selected in step a1, and using them in combination;

b. in one reaction mixture or enzyme reaction system, that is a single reaction channel, synchronously initiating the specifically-catalyzed reactions of multiple kinds of the enzymes to be measured with their corresponding chromogenic substrates combined for use as a mixture;

c. selecting a combination of wavelengths for measuring absorbance: taking the chromogenic substrate whose chromogenic product thereof has the difference absorbance peak maximum wavelength nearest to the infrared end as chromogenic substrate A, determining the absorbance of the chromogenic product at the difference absorbance peak maximum wavelength of the chromogenic product of chromogenic substrate A; determining the absorbance of the chromogenic products or chromogenic substrates of the other enzymes whose activities are to be measured at the isoabsorbance wavelengths of chromogenic substrate A;

d. realizing simultaneous measurement of multiple wavelength absorbances for concomitantly monitoring the reaction processes of multiple kinds of the enzymes to be measured in a single channel through swift alteration of the wavelengths selected in the combination;

e. developing an approach of data processing for eliminating the interference of the overlapped absorbance of chromogens involved in enzyme reactions based on linear additivity of absorbances of non-interacting compounds, to obtain an absorbance change curve of the chromogenic product or substrate of each enzyme to be measured after the elimination of the overlapping interference in absorbance spectra; if the action of an enzyme to be measured is not subject to the interference by any enzyme products and substrates in the reaction system, and the substrate concentration is over three times of a Michaelis constant of the corresponding enzyme, the classical initial rate method is used to analyze the absorbance change curve of the chromogenic product or substrate with no disturbing absorbance to determine the initial rate; if the action of an enzyme to be measured is not disturbed by any enzyme products and substrates in the reaction system, however, the concentration of the used chromogenic substrate is over 5% of a Michaelis constant of the corresponding enzyme but less than three times of the Michaelis constant, the classical initial rate method is integrated with kinetic analysis of reaction process to analyze the reaction curve as the absorbance change of the chromogenic product or substrate thereof with no disturbing absorbance to determine the initial rate; when the action of an enzyme to be measured is disturbed by substrates and/or products of itself and/or other enzymes in the reaction system, a group of the differential rate equations that describe the kinetics of the reaction system is numerically integrated for fitting to the reaction curve as the absorbance change of the chromogenic product or substrate of the enzyme to be measured with no disturbing absorbance of chromogenic products and chromogenic substrates in the reaction system, to estimate the maximum reaction rate thereof, which is used directly as an index of the activity of the enzyme to be measured, or is further converted according to the differential rate equations into an initial rate at the substrate concentration of 93% of the initial one for reflecting the activity of the enzyme to be measured.

2. The method for simultaneously measuring the activities of multiple kinds of enzymes in single channel through concomitantly monitoring multiple wavelength absorbances according to claim 1, wherein: the difference absorbance peak maximum wavelengths of chromogenic products versus their chromogenic substrates are greater than 300 nm, and the maximal absorbance peak wavelengths of the chromogenic substrates thereof are less than the maximal absorbance peak wavelengths of the corresponding chromogenic products, otherwise the rates for the reversed reaction catalyzed by the enzymes are determined to reflect their activities; for any two chromogenic substrates whose chromogenic products formed thereof under the actions of the enzymes whose activities are to be measured have the difference absorbance peak maximum wavelengths adjacent to each other in the aforementioned array of the difference absorbance peak maximum wavelengths, when the difference absorbance peak maximum wavelength of the chromogenic product is both closer to the UV end and is equal to or less than 5 nm distance away from the maximal isoabsorbance wavelength of the chromogenic substrate whose chromogenic product has the difference absorbance peak maximum wavelength closer to the infrared end, this two are the preferred combination of chromogenic substrates; in the used combination of all chromogenic substrates, each chromogenic substrate is only converted into the corresponding chromogenic product(s) by the action of one enzyme whose activity is to be measured, without being affected or being affected in a negligible way by any other enzymes from the sample; the expression "without being affected or being effected in a negligible way by any other enzymes from the sample" herein means when the concentration of the chromogenic substrate corresponding to enzyme I from the sample differ from the Michaelis constant thereof in less than 50%, the specific activity of any other enzymes from the sample acting on the chromogenic substrate thereof is less than 1% of the specific activity of enzyme I acting on the chromogenic substrate; in step b, a buffer and reaction conditions suitable for the enzyme to be measured to take effect in simultaneously measuring the activities are selected, that is, the buffer has a pH from 5.0 to 9.0, and close to the optimum pH of the enzyme to be measured in the sample whose specific activity is the lowest, the used reaction temperature is between 20 and 40° C.

3. The method for simultaneously measuring the activities of multiple kinds of enzymes in single channel through concomitantly monitoring multiple wavelength absorbances according to claim 2, wherein: said chromogenic substrates comprise natural chromogenic substrates and nonnatural chromogenic substrates; wherein the natural chromogenic substrates comprises nicotinamide adenine dinucleotide and nicotinamide adenine dinucleotide phosphate; nonnatural chromogenic substrates consist of chromophores and moieties recognized by enzymes for action, the chromophores comprise, but are not limited to, 4-nitrophenol, 4-nitrobenzenethiol, 4-nitroaniline, 4-nitro-1-naphthol, 4-nitro-1-naphthylthiol, 4-nitro-1-naphthylamine, 2-naphthol, 4-chloro phenol, rosolic acid or the derivatives of these aromatic phenols and/or aromatic amines.

4. The method for simultaneously measuring the activities of multiple kinds of enzymes in single channel through concomitantly monitoring multiple wavelength absorbances according to claim 1, wherein: for simultaneously measuring the activities of two kinds of enzymes in single channel through concomitantly monitoring two wavelength absorbances:

in step a, the two enzymes to be measured are named as enzyme A and enzyme B, the two required chromophores are chromophore A and chromophore B, respectively, the two corresponding chromogenic substrates are chromogenic substrate A and chromogenic substrate B, respectively, two chromogenic products produced by the action of the two enzymes to be measured are chromogenic product A and chromogenic product B, respectively, the combination of these chromogenic substrates and chromogenic products is required to meets the following criteria: (1) the difference absorbance peak maximum wavelength X1 of chromogenic product A is closer to the infrared end, the difference absorbance peak maximum wavelength X2 of chromogenic product B is closer to the UV end, the distance between the difference absorbance peak maximum wavelength X2 of chromogenic product B and the difference absorbance peak maximum wavelength X1 of chromogenic product A is greater than 30 nm, and preferably as far as possible; (2) the maximum isoabsorbance wavelength of chromogenic product A is Y1, and is equal to or less than 25 nm distance away from the difference absorbance peak maximum wavelength X2 of chromogenic product B, and the distance is preferably as short as possible;

in steps b, c and d, synchronously initiating the reactions of two kinds of the enzymes from a sample with chromogenic substrate A and chromogenic substrate B in a single channel, to obtain chromogenic product A and chromogenic product B; selecting the difference absorbance peak maximum wavelength X1 of chromogenic product A as $\lambda 1$ to determine the absorbance of chromogenic product A, selecting the maximum isoabsorbance wavelength Y1 of chromogenic product A as $\lambda 2$ to determine the absorbance of chromogenic product B; concomitantly monitoring two wavelength absorbances records the reaction processes of the two kinds of enzymes to be measured in a single channel by swift alteration of the measuring wavelength;

in step e, developing an approach of data processing for eliminating the interference of the overlapped absorbances of chromogens involved in enzyme reactions based on linear additivity of absorbances of non-interacting compounds, to obtain an absorbance change curve of the chromogenic product or substrate of each enzyme to be measured after the elimination of the overlapping interference in absorbance spectra; if the action of an enzyme to be measured is not subject to the interference by any enzyme products and substrates in the reaction system, and the substrate concentration is over three times of the Michaelis constant of the corresponding enzyme, the classical initial rate method is used to analyze the absorbance change curve of the chromogenic product or substrate with no disturbing absorbance to determine the initial rate; if the action of an enzyme to be measured is not interfered by any enzyme products and substrates in the reaction system, however, the concentration of the used chromogenic substrate is over 5% of the Michaelis constant of the corresponding enzyme but less than three times of the Michaelis constant, the classical initial rate method is integrated with kinetic analysis of reaction process to analyze the reaction curve as the absorbance change of the chromogenic product or substrate thereof with no disturbing absorbance to determine the initial rate; when the action of an enzyme to be measured is interfered by substrates and/or products of itself and/or other enzymes in the reaction system, a group of the differential rate equations that describe the kinetics of the reaction system is numerically integrated for fitting to the reaction curve as the absorbance change of the chromogenic product or substrate of the enzyme to be measured with no disturbing absorbance of chromogenic products and chromogenic substrates in the reaction system, to estimate the maximum reaction rate thereof, which is used directly as an index of the activity of the enzyme to be measured, or is further converted according to the differential rate equations into an initial rate at the substrate concentration of 93% of the initial one for reflecting the activity of the enzyme to be measured; taking a wavelength that is less than 25 nm away from the difference absorbance peak maximum wavelength of chromogenic product A as $\lambda 1$, and determining the absorbance at this wavelength as A1, taking a wavelength that is less than 25 nm away from the maximum isoabsorbance wavelength of chromogenic product A as $\lambda 2$, and determining the absorbance at this wavelength as A2, the calculation of the interference-free absorbance of chromogenic products or substrates requires the solution of the following two linear equations in a group based on the linear additivity of absorbances to eliminate the overlapping absorbance of compounds:

$$A_1 = A_{10} + E31 \times P_1 + E34 \times P_2$$

$$A_2 = A_{20} + E32 \times P_1 + E35 \times P_2$$

which is further converted into the following group of two-element linear equations:

$$A_1 = A_{10} + A_{1a} + R33 \times A_{2b}$$

$$A_2 = A_{20} + A_{2b} + R31 \times A_{1a}$$

wherein $$R31 = E32/E31$$

$$R33 = E34/E35$$

in the above equations, $P_1$ is the instantaneous concentration of chromogenic product A; $P_2$ is the instantaneous concentration of chromogenic product B; E31 is the difference molar extinction coefficient of chromogenic product A versus chromogenic substrate A at $\lambda 1$; E32 is the difference molar extinction coefficient of chromogenic product A versus chromogenic substrate A at $\lambda 2$; E34 is the difference molar extinction coefficient of chromogenic product B versus chromogenic substrate B at $\lambda 1$; E35 is the difference molar extinction coefficient of chromogenic product B versus chromogenic substrate B at $\lambda 2$; $A_1$ is the total instantaneous absorbance at $\lambda 1$ before correcting overlapped absorbance interference, $A_2$ is the total instantaneous absorbance at $\lambda 2$ before correcting overlapped absorbance interference; $A_{1a}$ is the net instantaneous absorbance of chromogenic product A at $\lambda 1$ after correcting overlapped absorbance interference, which equals to the product of $P_1$ times E31, $A_{2b}$ is the net instantaneous absorbance of chromogenic products B at $\lambda 2$ after correcting overlapped absorbance interference, which equals to the product of $P_2$ times E35; $A_{10}$ is the absorbance of reaction system at $\lambda 1$ before generating any chromogenic products, which is the background absorbance of the reaction system, equivalent to the sum of the absorbance at $\lambda 1$ of the reaction system containing all chromogenic substrates at the same concentrations and the absorbance at $\lambda 1$ of the reaction system containing a sample at the same concentration; $A_{20}$ is the absorbance of reaction system at $\lambda 2$ before generating any chromogenic products, which is the background absorbance of the reaction system, equivalent to the sum of the absorbance at $\lambda 2$ of the reaction system containing all chromogenic substrates at the same concentrations and the absorbance at λ2 of the reaction system containing a sample at the same concentration;

if a substrate or product of some an enzyme in the reaction channel inhibits or activates another enzyme, then the activity of the enzyme being interfered is measured as follows:

obtaining the interference-free absorbance change curves of two enzymes, and then calculating the concentration change curves of the compounds that causes the interfering effect; differential rate equations containing the interfering effects are numerically integrated to calculate theoretical reaction plots for fitting to the interference-free absorbance change curves of the disturbed enzyme, the maximum reaction rate $V_m$ for the best fitting is the interference-free activity of the enzyme to be measured; according to the differential rate equations of the enzyme being interfered, its $V_m$ and 93% of the initial substrate concentration thereof, calculating the initial rate of the enzyme when the reaction is just started and the disturbing compounds do not significantly accumulate yet, to reflect the activity of the enzyme to be measured;

when a chromogenic product of only one enzyme has competitive inhibiting effect on another enzyme, firstly determining the interference-free absorbance change curves $A_{1a}$ and $A_{2b}$ of chromogenic product A and chromogenic product B at λ1 and λ2, respectively; assigning the initial concentration of chromogenic substrate A to $C_1$, and the initial concentration of chromogenic substrate B to $C_2$; for the conversion of $V_m$ into the initial rate, assigning the maximum reaction rate of enzyme B to $V_{mB}$, the preset concentration of the chromogenic substrate B as 93% of that of $C_2$, the Michaelis constant of enzyme B for chromogenic substrate B to $K_{mB}$; if chromogenic product A competitively inhibits enzyme B with a competitive inhibition constant of $K_{ia}$, then the rate equation of enzyme B is:

$$\frac{dA_{2b}}{C_2 \times E_{34}} = \frac{V_{mB} \times dt}{K_{mB} \times (1 + A_{1a}/K_{ia}/E_{31}) + C_2}$$

the above equation is integrated on time from 0 to t to obtain $$\frac{1}{C_2 \times E_{34}} \times \int_0^t dA_{2b} = V_{mB} \times \int_0^t \frac{1}{K_{mB} \times (1 + A_{1a}/K_{ia}/E_{31}) + C_2} \times dt$$

the integration term on the left side is the net change of absorbance of chromogenic product B between reaction time t and reaction time 0; the integration term on the right side of the equation is a numerical integration by taking the concentration of chromogenic product A during dt as a constant, that is to calculate $$x = \frac{1}{K_{mB} \times (1 + A_{1a}/K_{ia}/E_{31}) + C_2}$$

taking dt as Δt, calculating the x at each recorded time point, summing all of the x and then subtracting the x at the starting point and the end point to obtain sumx, $V_{mB}$ is calculated according to the following formula, and the noninterfering initial rate s2 is obtained according to the differential kinetic equations thereof;

$$V_{mB} = \int_0^t dA_{2b}/(C_2 \times E_{34} \times \text{sum}x \times \Delta t)$$

$$s_2 = 0.93 \times C_2 \times V_{mB}/(K_{mB} + 0.93 \times C_2)$$

in the above calculating formula, the stoichiometric relationship for converting chromogenic substrate A into chromogenic product A by enzyme A is 1:1, the stoichiometric relationship for converting chromogenic substrate B into chromogenic product B by enzyme B is also 1:1.

5. The method for simultaneously measuring the activities of multiple kinds of enzymes in single channel through concomitantly monitoring multiple wavelength absorbances according to claim 4, wherein:

in step a, the combination of chromophore A and chromophore B is selected as follows: the maximum isoabsorbance wavelength Y1 of chromogenic product A equals to or is less than 5 nm away from the difference absorbance peak maximum wavelength X2 of chromogenic product B;

in step c, after selecting the difference absorbance peak maximum wavelength X1 of product A as λ1, selecting the measuring wavelength λ2 as follows: if the difference of the molar extinction coefficients of chromogenic product B versus chromogenic substrate B at the maximum isoabsorbance wavelength Y1 of chromogenic product A is higher than 30% of that at the difference absorbance peak maximum wavelength X2 of chromogenic product B, selecting the maximum isoabsorbance wavelength Y1 of chromogenic product A as λ2, otherwise, taking the difference absorbance peak wavelength of chromogenic product B that is nearest to the maximum isoabsorbance wavelength Y1 of chromogenic product A as λ2, or a wavelength that is near to the difference absorbance peak wavelength of chromogenic product B and gives the differences of the molar extinction coefficients of other chromogenic products versus their corresponding chromogenic substrates less than 20% of the difference of the molar extinction coefficients of chromogenic product B versus chromogenic substrate B as λ2, to measure the absorbance of chromogenic product B;

in step e, it is required to determine R31 as the correcting coefficient of the absorbance interference of chromogenic product A; when determining R31, only the group of all chromogenic substrates that are required for the action of enzyme A is used without the addition of any chromogenic substrates for the actions of other enzymes to be measured, to make the reaction system have no absorbance at the measuring wavelengths λ1 and λ2 brought about by chromogenic substrate B and chromogenic product B, the absorbance of the reaction channel at the two selected measuring wavelengths are monitored concomitantly, till the absorbance changing at λ2 is greater than 0.005 or the absorbance changing at λ1 is greater than 0.500; taking the absorbance at λ1 as x-coordinate, the absorbance at λ2 as y-coordinate for regression analysis gives the slope of the obtained regression line as the correcting coefficient R31;

in step e, it is required to determine the R33 as the correcting coefficient of the absorbance interference of chromogenic product B; when determining R33, only the group of all chromogenic substrates that are required for the action of enzyme B is used without the addition of any chromogenic substrates for the actions of other enzymes to be measured, to make the reaction system have no absorbance at the measuring wavelengths λ1 and λ2 brought about by chromogenic substrate A or chromogenic product A, the absorbance changing of the reaction channel at the two selected measuring wavelengths are concomitantly monitored, till the absorbance changing at λ2 is greater than 0.500 or the absorbance changing at λ1 is greater than 0.005; taking the absorbance at λ2 as x-coordinate, the absorbance at λ1 as y-coordinate to do regression analysis gives the slope of the obtained regression line as correcting coefficient R33.

6. The method for simultaneously measuring the activities of multiple kinds of enzymes in single channel through concomitantly monitoring multiple wavelength absorbances according to claim 5, wherein:

the chromogenic substrate corresponding to enzyme A comprises 4-nitrophenyl acetate having the maximum isoabsorbance wavelength between 310 and 330 nm upon hydrolysis, 4-nitrophenylphosphate, 4-nitrophenylsulphate, 4-nitrophenyl-β-D-galactoside and γ-glutamyl-4-nitroaniline having the maximum isoabsorbance wavelengths between 320 and 350 nm upon hydrolysis, 5-mercapto-2-nitrophenylacetic acid and 5-mercapto-2-nitrobenzoic acid having the maximum isoabsorbance wavelengths between 350 and 370 nm upon reduction of their disulfide bonds by corresponding sulfuhydryl groups released from chromogenic substrates under the action of enzymes; chromogenic substrate B of enzyme B corresponding to the chromogenic substrate A of this kind of enzyme A are mainly natural chromogenic substrates, including nicotinamide adenine dinucleotide and nicotinamide adenine dinucleotide phosphate;

enzyme A corresponding to chromogenic substrate A comprises, but is not limited to, arylesterase, phosphatase, sulphatase, γ-glutamyltransferase, amidase corresponding to natural amino acid α-carboxyl and glycosidase; enzyme B corresponding to this kind of enzyme A comprises, but not limited to, lactate dehydrogenase LDH, malate dehydrogenase MDH, LDH coupling alanine aminotransferase and MDH coupling aspartate aminotransferase.

7. The method for simultaneously measuring the activities of multiple kinds of enzymes in single channel through concomitantly monitoring multiple wavelength absorbances according to claim 3, wherein: simultaneously measuring the activities of three kinds of enzymes in single channel through concomitantly monitoring three wavelength absorbances:

in step a, the three enzymes to be measured are named as enzyme A, enzyme B, and enzyme C, the required chromogenic substrates are chromogenic substrate A, chromogenic substrate B and chromogenic substrate C, respectively, which generate, under the action of the corresponding enzymes, chromogenic product A, chromogenic product B and chromogenic product C, respectively; the combinations of these chromogenic substrates with chromogenic products meet the following criteria: (1) the difference absorbance peak maximum wavelength of chromogenic product A is X1 and nearest to the infrared end, the difference absorbance peak maximum wavelength of chromogenic product C is X3 and nearest to the UV end, the difference absorbance peak maximum wavelength of chromogenic product B is X2 and locates between X1 and X3, the distances between any pairs among X2 and X1 and X3 are all greater than 30 nm and preferably as far as possible; (2) the maximum isoabsorbance wavelength of chromogenic product A is Y1 and the second maximum isoabsorbance wavelength is Ys; the maximum isoabsorbance wavelength for the conversion of chromogenic substrate B into chromogenic product B is Y2, and preferably as far as possible away from Y1, but as near as possible to Ys; (3) the distance between Y1 and X2 is less than 25 nm, and preferably as shorter as possible; the distances between any pairs among Y2 and Ys and X3 are all less than 25 nm and preferably as short as possible;

in step b, simultaneously initiating the reactions of three kinds of enzymes with chromogenic substrate A, chromogenic substrate B and chromogenic substrate C in a single channel, to obtain the corresponding chromogenic product A, chromogenic product B and chromogenic product C;

in step c, taking the wavelength at the difference absorbance peak maximum wavelength X1 of chromogenic product A or within a distance less than 25 nm to it as λ1 to determine the absorbance of chromogenic product A, selecting a wavelength equal to or within a distance less than 25 nm to the maximum isoabsorbance wavelength Y1 of chromogenic product A as λ2 to determine the absorbance of chromogenic product B, selecting a wavelength equal to or within a distance less than 25 nm to the maximum isoabsorbance wavelength Y2 of chromogenic product B as λ3 to determine the absorbance of chromogenic product C;

in step d, swift alteration of wavelengths realizes the simultaneous measurement of three wavelength absorbances to monitor the reaction processes of the three kinds of enzymes to be measured in a single reaction system or channel;

in step e, developing an approach of data processing for eliminating the interference of the overlapped absorbance of chromogens involved in enzyme reactions based on the linear additivity property of absorbances of non-interacting compounds, to obtain an absorbance change curve of the chromogenic product or substrate of each enzyme to be measured after the elimination of the overlapping interference in absorbance spectra; if the action of an enzyme of interest for activity assay is not subject to the interference by the products and substrates of the other enzymes in the reaction system, and the substrate concentration is over three times of a Michaelis constant of the corresponding enzyme, the classical initial rate method is used to analyze the absorbance change curve of the chromogenic product or substrate with no disturbing absorbance to determine the initial rate; if the action of an enzyme to be measured is not disturbed by the products and substrates of the other enzymes in the reaction system, however, the concentration of the used chromogenic substrate is over 5% of a Michaelis constant of the corresponding enzyme but less than three times of the Michaelis constant, the classical initial rate method is integrated with kinetic analysis of reaction process to analyze the reaction curve as the absorbance change of the chromogenic product or substrate thereof with no disturbing absorbance to determine the initial rate; when the action of an enzyme to be measured is disturbed by substrates and/or products of itself and/or other enzymes in the reaction system, a group of the differential rate equations that describe the kinetics of the reaction system is numerically integrated for fitting to the reaction curve as the absorbance change of the chromogenic product or substrate of the enzyme to be measured with no disturbing absorbance of chromogenic products and chromogenic substrates in the reaction system, to estimate the maximum reaction rate thereof, which is used directly as an index of the activity of the enzyme to be measured, or is further converted according to the differential rate equations into an initial rate at the substrate concentration of 93% of the initial one for reflecting the activity of the enzyme to be measured; the calculation of the interference-free absorbance of chromogenic products or substrates is required to solve the following three-element linear equations in a group based on linear additivity of absorbances to eliminate the overlapping absorbances of multiple compounds:

$A_1 = A_{10} + A_{1a} + R33 \times A_{2b} + R35 \times A_{3c}$ $A_2 = A_{20} + A_{2b} + R31 \times A_{1a} + R36 \times A_{3c}$ $A_3 = A_{30} + A_{3c} + R32 \times A_{1a} + R34 \times A_{2b}$ wherein $R31 = E32/E31$ $R32 = E33/E31$ $R33 = E34/E35$ $R34 = E36/E35$ $R35 = E37/E39$ $R36 = E38/E39$ in the above formula, $A_1$ is the instantaneous absorbance at $\lambda 1$ before correcting absorbance interference, $A_2$ is the instantaneous absorbance at $\lambda 2$ before correcting absorbance interference, $A_3$ is the instantaneous absorbance at $\lambda 3$ before correcting absorbance interference; $A_{1a}$ is the net instantaneous absorbance of chromogenic product A at $\lambda 1$ after correcting absorbance interference, $A_{2b}$ is the net instantaneous absorbance of chromogenic product B at $\lambda 2$ after correcting absorbance interference, $A_{3c}$ is the net instantaneous absorbance of chromogenic product C at $\lambda 3$ after correcting absorbance interference; $A_{10}$ is the absorbance of reaction system at $\lambda 1$ before generating any chromogenic products, $A_{20}$ is the absorbance of reaction system at $\lambda 2$ before generating any chromogenic products, $A_{30}$ is the absorbance of reaction system at $\lambda 3$ before generating any chromogenic products; E31 is the difference molar extinction coefficient of chromogenic product A versus chromogenic substrate A at $\lambda 1$, E32 is the difference molar extinction coefficient of chromogenic product A versus chromogenic substrate A at $\lambda 2$, E33 is the difference molar extinction coefficient of chromogenic product A versus chromogenic substrate A at $\lambda 3$; E34 is the difference molar extinction coefficient of chromogenic product B versus chromogenic substrate B at $\lambda 1$, E35 is the difference molar extinction coefficient of chromogenic product B versus chromogenic substrate B at $\lambda 2$, E36 is the difference molar extinction coefficient of chromogenic product B versus chromogenic substrate B at $\lambda 3$; E37 is the differential molar extinction coefficient of chromogenic product C versus chromogenic substrate C at the measuring wavelength $\lambda 1$, E38 is the difference molar extinction coefficient of chromogenic product C versus chromogenic substrate C at the measuring wavelength $\lambda 2$, E39 is the difference molar extinction coefficient of chromogenic product C versus chromogenic substrate C at the measuring wavelength $\lambda 3$; in the above formula, the stoichiometric relationship of converting chromogenic substrate A into chromogenic product A is 1:1; the stoichiometric relationship of converting chromogenic substrate B into chromogenic product B is 1:1; the stoichiometric relationship of converting chromogenic substrate C into chromogenic product C is 1:1;

if a substrate or product of some an enzyme in the reaction channel inhibits or activates another enzyme, then the activity of the disturbed enzyme is measured as follows:

obtaining the interference-free absorbance change curves, based on which the concentration changing curves of the compounds that causes the interfering effect is calculated; differential rate equations containing the interfering effect are numerically integrated to calculate theoretical reaction curves for fitting to the interference-free absorbance change curve of the disturbed enzyme, the maximum reaction rate $V_m$ for the best fitting is the activity of the enzyme to be measured; according to the differential rate equations of the enzyme, $V_m$ and 93% of the initial substrate concentration thereof, calculating the initial rate of the enzyme when the reaction is just initiated and the interfering compounds do not significantly accumulate yet, to reflect the activity of the enzyme to be measured.

8. The method for simultaneously measuring the activities of multiple kinds of enzymes in single channel through concomitantly monitoring multiple wavelength absorbances according to claim 7, wherein: simultaneously measuring the activities of three kinds of enzymes in single channel through concomitantly monitoring three wavelength absorbances:

in step a, the combination of chromogenic substrates is selected according to the following principle: the used chromogenic substrate A, chromogenic substrate B and chromogenic substrate C make the maximum isoabsorbance wavelength Y1 of chromogenic product A equal to or is less than 5 nm away from the difference absorbance peak maximum wavelength X2 of chromogenic product B, the maximum isoabsorbance wavelength Y2 of chromogenic product B and the second maximum isoabsorbance wavelength Ys of chromogenic products A and the difference absorbance peak maximum wavelength X3 of chromogenic product C equal to each other or the distances between any pairs among them are not greater than 5 nm;

in step c, after selecting the difference absorbance peak maximum wavelength X1 of chromogenic product A as $\lambda 1$, the other two measuring wavelength $\lambda 2$ and $\lambda 3$ are selected according to the following principles: when the difference of the molar extinction coefficients of chromogenic product B versus chromogenic substrate B at the maximum isoabsorbance wavelength Y1 of chromogenic product A is higher than 30% of the difference of the molar extinction coefficients of chromogenic product B versus chromogenic substrate B at the difference absorbance peak maximum wavelength X2, select Y1 as the measuring wavelength $\lambda 2$, otherwise, selecting the difference absorbance peak wavelength of chromogenic product B nearest to the maximum isoabsorbance wavelength Y1 of chromogenic product A as $\lambda 2$, or a wavelength that is near to the difference absorbance peak wavelength of chromogenic product B and gives the differences of the molar extinction coefficients of all the other chromogenic products versus their corresponding chromogenic substrates less than 20% of the difference of the molar extinction coefficients of chromogenic product B versus chromogenic substrate B as $\lambda 2$, to measure the absorbance of chromogenic product B; if the difference of the molar extinction coefficients of chromogenic product C versus chromogenic substrate C at the second maximum isoabsorbance wavelength Ys of chromogenic product A or at the maximum isoabsorbance wavelength Y2 of chromogenic product B and chromogenic substrate B is higher than 30% of the difference of the molar extinction coefficients of chromogenic product C versus chromogenic substrate C at their difference absorbance peak maximum wavelength X3, select Y2 or Ys as $\lambda 3$ to measure the absorbance of chromogenic product C, otherwise, selecting a wavelength that is nearest to the maximum isoabsorbance wavelength Y2 of chromogenic product B or the second maximum isoabsorbance wavelength Ys of chromogenic product A as $\lambda 3$, or a wavelength that is near to the difference absorbance peak maximum wavelength of chromogenic product C and gives the differences of the molar extinction coefficients of all of the other chromogenic products versus their corresponding chromogenic substrates less than 20% of the difference of the molar extinction coefficients of chromogenic product C versus chromogenic substrate C as $\lambda 3$, to measure the absorbance of chromogenic product C;

in step e, it is required to determine R31 and R32 as correcting coefficients of the absorbance disturbing of chromogenic product A; when determining, only all chromogenic substrates of enzyme A is used without using any chromogenic substrates for other enzymes to be measured, make the reaction system has no absorbance at the measuring wavelengths $\lambda 1$, $\lambda 2$ and $\lambda 3$ brought about by chromogenic substrate B, chromogenic product B, chromogenic substrate C or chromogenic product C, simultaneously measuring the absorbance changing in the reaction channel at the three measuring wavelengths, till both the absorbance changings at $\lambda 2$ and $\lambda 3$ are greater than 0.005 or the absorbance changing at $\lambda 1$ is greater than 0.500; take the absorbance at $\lambda 1$ as x-coordinate, the absorbance at $\lambda 2$ and $\lambda 3$ as y-coordinate to do regression analysis, the slope of the obtained regression line of the absorbance changing at $\lambda 2$ is correcting coefficient R31, the slope of the obtained regression line of the absorbance changing at $\lambda 3$ is correcting coefficient R32;

in step e, it is required to determine R33 and R34 as correcting coefficients of the absorbance disturbing of chromogenic product B; when determining, only all chromogenic substrates of enzyme B is used without using any chromogenic substrates for other enzymes to be measured, make the reaction system has no absorbance at the measuring wavelengths $\lambda 1$, $\lambda 2$ and $\lambda 3$ brought about by chromogenic substrate A, chromogenic product A, chromogenic substrate C or chromogenic product C, simultaneously measuring the absorbance changing in the reaction channel at the three measuring wavelengths, till both the absorbance changings at $\lambda 2$ and $\lambda 3$ are greater than 0.005 or the absorbance changing at $\lambda 1$ is greater than 0.500; take the absorbance at $\lambda 2$ as x-coordinate, the absorbance at $\lambda 1$ and $\lambda 3$ as y-coordinate to do regression analysis, the slope of the obtained regression line of the absorbance changing at $\lambda 1$ is correcting coefficient R33, the slope of the obtained regression line of the absorbance changing at $\lambda 3$ is correcting coefficient R34;

in step e, it is required to determine R35 and R36 as correcting coefficients of the absorbance disturbing of chromogenic product C; when determining, only all chromogenic substrates of enzyme C is used without using any chromogenic substrates for other enzymes to be measured, make the reaction system has no absorbance at the measuring wavelengths $\lambda 1$, $\lambda 2$ and $\lambda 3$ brought about by chromogenic substrate A, chromogenic product A, chromogenic substrate B or chromogenic product B, simultaneously measuring the absorbance changing in the reaction channel at the three measuring wavelengths, till both the absorbance changings at $\lambda 2$ and $\lambda 1$ are greater than 0.005 or the absorbance changing at $\lambda 3$ is greater than 0.500; take the absorbance at $\lambda 3$ as x-coordinate, the absorbance at $\lambda 1$ and $\lambda 2$ as y-coordinate to do regression analysis, the slope of the obtained regression line of the absorbance changing at $\lambda 1$ is correcting coefficient R35, the slope of the obtained regression line of the absorbance changing at $\lambda 2$ is correcting coefficient R36.

9. The method for simultaneously measuring the activities of multiple kinds of enzymes in single channel through concomitantly monitoring multiple wavelength absorbances according to claim 8, wherein:

in step a, chromogenic substrate A corresponding to enzyme A comprises 4-nitro-1-naphthylphosphate which upon hydrolysis has two isoabsorbance wavelengths that locate at 315 to 335 nm and 395 to 415 nm, respectively, 4-nitro-1-naphthylsulphate which upon hydrolysis has two isoabsorbance wavelengths that locate at 315 to 335 nm and 395 to 415 nm, 4-nitro-1-naphthylacetate which upon hydrolysis has two isoabsorbance wavelengths that locate at 310 to 330 nm and 375 to 395 nm, 4-nitro-1-naphthyl-β-D-galactoside which upon hydrolysis has two isoabsorbance wavelengths that locate at 320 to 345 nm and 390 to 410 nm, 4-nitro-1-(N-lysyl) naphthylamide which upon hydrolysis has the maximum isoabsorbance wavelength at 385 to 410 nm, this chromogenic substrate A generates, under the action of enzyme A, 4-nitro-1-naphthol or 4-nitro-1-naphthylamine or derivatives thereof as chromogenic product A; chromogenic substrates B corresponding to this chromogenic substrate A is mainly 4-nitrophenol or 4-nitroaniline derivatives, which generates, under the action of the corresponding enzyme B, chromogenic product B which are 4-nitrophenol, 4-nitroaniline or 4-nitrophenylthiol; chromogenic substrate C corresponding to chromogenic substrate A and chromogenic substrate B comprises nicotinamide adenine dinucleotide and nicotinamide adenine dinucleotide phosphate;

enzyme A corresponding to chromogenic substrate A comprises, but is not limited to, arylesterase, phosphatase, sulphatase, γ-glutamyltransferase, amidase and glycosidase corresponding to peptidase acting on amides of α-carboxyl group of natural amino acid; enzyme B corresponding to chromogenic substrate B comprises the other hydrolase other than the selected enzyme A but still belonging to hydrolytic enzymes; enzyme C corresponding to chromogenic substrate C comprises, but is not limited to, lactate dehydrogenase LDH, malate dehydrogenase MDH, LDH coupling alanine aminotransferase and MDH coupling aspartate aminotransferase.

* * * * *